(12) United States Patent
Dolganov

(10) Patent No.: US 6,555,666 B1
(45) Date of Patent: Apr. 29, 2003

(54) TRANSCRIPTS ENCODING IMMUNOMODULATORY POLYPEPTIDES

(76) Inventor: Gregory Dolganov, 896 Middle Ave., Menlo Park, CA (US) 94025

( * ) Notice: Subject to any disclaimer, the term of this patent is extended or adjusted under 35 U.S.C. 154(b) by 0 days.

(21) Appl. No.: 09/168,595

(22) Filed: Oct. 8, 1998

Related U.S. Application Data

(62) Division of application No. 08/592,126, filed on Jan. 26, 1996, now Pat. No. 5,821,091.

(51) Int. Cl.[7] .......................... C07H 21/02; C07H 21/04
(52) U.S. Cl. .................. 536/23.1; 536/23.5; 536/24.31
(58) Field of Search .............................. 536/23.1, 23.5, 536/24.31, 24.33

(56) References Cited

PUBLICATIONS

Longtine et al. Curr. Opin Cell Biol. 8(1): 106–119 (1996.*
Sakai et al, Journal of Neuro–Oncol. vol. 57, pp 169–177, 2002.*
Chant, John; Cell, vol. 84, pp 187–190, 1996.*

\* cited by examiner

*Primary Examiner*—W. Gary Jones
*Assistant Examiner*—Jehanne Souaya
(74) *Attorney, Agent, or Firm*—Larry W. Thrower; Peter J. Dehlinger; Perkins Coie LLP

(57) ABSTRACT

Substantially-isolated polynucleotides encoding human polypeptides having immunomodulatory activity; human homologs of yeast RAD50, Drosophila Septin-2 and rat Acyl-CoA Synthetase compositions and methods; method for detecting the presence of activated T-cells.

3 Claims, 2 Drawing Sheets

GCCACTCACACAGCATCTCCAAGATCAGGGACCAGTACTTCCTGAGCTTGACAGAGAATGA
ATGTGTCAGACTGACCTCTGCCCATTTTGTAGTTTTCTCATCATTTTCTCACTCAGTCTTC
CCTTTTCAAGGGCCCACACTCTTCCCGAGGGCTGGGCCTAGTGAGCGGGGTCACAGTACAT
ATGGTTTCTGGGACTGAGAAGGTGGAAGATGTGTCCATAGAGCTTTTGTTTCCTAAGCAAC
GTATTACTGCCATGATTCCATTCCCTAGATGATGCTGGTGATGCAAGCTGGCTTCTCTTGG
CCAGCCTACCCTACTGCTGGGTAGTGTTTATGCCCCATGGCCAGACACTGAAGAGGGAGAC
AGGAAAAGCACATATCCACACCTTCCACCCTCAGACATTCCTGTAACTTGAGCTTATCTAA
GGGGGCATTGTCATATGTCAGGGGTTCCCAAACTACGGTCTTCAGAAACACTGTTTACCCT
CCATAGAGGTTGTGTGCATCAGCCCAGGCAGAATCCTGCTTCATGAAGGTGTTTTCCTAAT
GCATGTGTGCATGGACCTGTCTCATGCTACACTGCAGGGCTGGTATTCAGCACCAATAGTT
ATTGTTGGCTGCTAAAATAGCAAACTAGCCAAAATGGCAG

TRANSCRIPTS ENCODING IMMUNOMODULATORY POLYPEPTIDES

This application is a divisional of co-owned U.S. patent application Ser. No. 08/592,126, filed Jan. 26, 1996, now U.S. application Ser. No. 5,821,091, which is incorporated herein by reference.

FIELD OF THE INVENTION

The present invention relates to immunomodulatory compositions and methods.

REFERENCES

Alani, E., et al., *Genetics* 122:47–57 (1989).
Ausubel, F. M., et al., in *Current Protocols in Molecular Biology*, John Wiley and Sons, Inc., Media, Pa. (1988).
Balasubramanian, M. K., et al., *J. Cell. Biol.* 125:1289 (1994).
Beames, et al., *Biotechniques* 11:378 (1991).
Bellanne-Chantelot, C., et al., *Cell* 70:1059–1068 (1992).
Boyum, A., *Scan J. Lab Invest* 21:77 (1968).
Burke, D. T., et al., *Science* 236:806–812 (1987).
Chenchik, A., et al., *Clontechniques* X(1):5–8 (1995).
Chomczynski, P., and Sacchi, N., *Anal. Biochem.* 162:156 (1987).
Chumakov, I., et al., *Nature* 359:380–387 (1992).
Fujino, T. and Yamamoto, T., *J. Biochem.* 111:197–203 (1992).
Glisin, V., et al., *Biochemistry* 13:2633 (1974).
Georgopoulos, K., et al. *EMBO J.* 9:109–115 (1990).
Harlow, E., et al., in *Antibodies: A Laboratory Manual*, Cold Spring Harbor Laboratory Press (1988).
Innis, M. A., et al., in *PCR Protocols*, Academic Press (1990).
Jakobsen, K. S., et al., *Nucleic Acids Res.* 18:3669 (1990).
Jakobsen, K. S., et al., "Direct mRNA Isolation Using Magnetic Oligo(dT) Beads: A Protocol for All Types of Cell Cultures, Animal and Plant Tissues" in *Advances in Biomagnetic Separation*, M. Uhlen, et al., Eds., Eaton Publishing (1994).
Lewis, D. B., et al., *Proc. Natl. Acad. Sci. USA* 85:9743 (1988).
Longmire, J. L., et al., *GATA* 10:69–76 (1993).
Morgan, J. G., et al., *Nucleic Acids Res.* 20:5173–5179 (1992).
Mullis, K. B., U.S. Pat. No. 4,683,202, issued Jul. 28, 1987.
Mullis, K. B., et al., U.S. Pat. No. 4,683,195, issued Jul. 28, 1987.
Piatak, M., et al., *AIDS* 7 (supp 2):S65–71 (1993).
Raymond, W. E. and Kleckner, N., *Mol. Gen. Genet.* 238:390–400 (1993).
Reilly, P. R., et al., *Baculovirus Expression Vectors: A Laboratory Manual*, 1992.
Sambrook, J., et al., in *Molecular Cloning: A Laboratory Manual,* Second Edition, Cold Spring Harbor Laboratory, Cold Spring Harbor, N.Y. (1989).
Siebert, P. D., et al., *Nuc. Acids Res.* 23(6):1087–1088 (1995).
Thorpe, R., et al., *Blood Rev.* 6:133–148 (1992).
Vandevyver, C., et al., *Genome Res.* 5:195–201 (1995).
Wadhwa, M., et al., in *Cytokines: A Practical Approach*, Balkwill, F. R., Ed., IRL Press, Oxford, 309–330 (1992).
Warrington, J. A., et al., *Genomics* 13:803–808 (1992).

BACKGROUND OF THE INVENTION

Cytokines and related immunomodulatory compounds play an important role in the regulation and function of the immune system, making them suitable targets for therapeutic intervention in diseases involving immune system dysfunction. It would therefore be desirable to identify heretofore undiscovered genes encoding cytokines and other immunomodulatory compounds, which may be useful as a basis for treatment of diseases affecting or influenced by the immune system. Present methods for the identification of such genes have met with limited success. These methods include (i) screening for DNAse I hypersensitive sites and HTF islands as potential markers for transcription units, (ii) cross-species hybridization analysis of genomic sequences, (iii) hybridization of radiolabelled cDNAs to arrayed genomic clones, (iv) screening of cDNA libraries with complex genomic probes, (v) exon trapping, (vi) random sequencing and assignment of tissue-specific cDNAs, (vii) "software trapping" of the genes in extensive genomic sequencing projects, and (viii) cDNA normalization, subtraction or/and hybridization selection using extensive genomic fragments.

Most of the above approaches have proven either unreliable, or have required a substantial effort to find the genes of interest. For instance, a conventional "functional" gene cloning route includes purifying the protein factor with a particular biological activity, microsequencing the protein to design a redundant oligoprobe, raising antibodies to the protein, expression cloning of the candidate gene or conventional screening of cDNA libraries with the redundant probe.

En masse cDNA sequencing efforts have contributed substantially to novel gene discovery by identifying a large number of novel sequences and tissue expression "profiles". However, because these efforts typically had no defined targets and depended on screening conventional cDNA libraries, they resulted in the preferential identification of common, abundant cDNAs, and were thus biased against the identification of novel cytokine genes, which tend to be selectively expressed at relatively low levels.

Exon trapping can be efficiently used to screen complex genomic DNA. This method is widely-used due to its independence of the gene expression in any particular cell line or tissue, but it requires substantial further efforts for isolation and identification of the genes in question.

Many of the difficulties in cytokine gene identification mentioned above have been overcome by employing methods detailed in the present specification. These methods were used to isolate a number of human cDNA fragments which may encode immunomodulatory molecules.

SUMMARY OF THE INVENTION

In one aspect, the present invention includes a substantially-isolated polynucleotide having a sequence encoding a human polypeptide having immunomodulatory activity. In one embodiment, the polynucleotide has the sequence represented as SEQ ID NO:65. In another embodiment, the polynucleotide has the sequence represented as SEQ ID NO:66. In another embodiment, the polynucleotide has the sequence represented as SEQ ID NO:67. In another embodiment, the polynucleotide has the sequence represented as SEQ ID NO:68. In another embodiment, the polynucleotide has the sequence represented as SEQ ID NO:70. In another embodiment, the polynucleotide has the sequence represented as SEQ ID NO:71. In another embodiment, the polynucleotide has the sequence represented as SEQ ID NO:72. In another embodiment, the polynucleotide has the sequence represented as SEQ ID NO:73. In another embodiment, the polynucleotide has the sequence represented as SEQ ID NO:74. In another embodiment, the polynucleotide has the sequence represented as SEQ ID NO:76. In another embodiment, the polynucleotide has the sequence represented as SEQ ID NO:78. In another embodiment, the polynucleotide has the sequence represented as SEQ ID NO:79. In another embodiment, the polynucleotide has the sequence represented as SEQ ID NO:82. In another embodiment, the polynucleotide has the sequence represented as SEQ ID NO:83. In another embodiment, the polynucleotide has the sequence represented as SEQ ID NO:85. In another embodiment, the polynucleotide has the sequence represented as SEQ ID NO:86. In another embodiment, the polynucleotide has the sequence represented as SEQ ID NO:88. In another embodiment, the polynucleotide has the sequence represented as SEQ ID NO:92. In another embodiment, the polynucleotide has the sequence represented as SEQ ID NO:95. In another embodiment, the polynucleotide has the sequence represented as SEQ ID NO:98. In another embodiment, the polynucleotide has the sequence represented as SEQ ID NO:99. In another embodiment, the polynucleotide has the sequence represented as SEQ ID NO:100. In another embodiment, the polynucleotide has the sequence represented as SEQ ID NO:104. In another embodiment, the polynucleotide has the sequence represented as SEQ ID NO:105. In another embodiment, the polynucleotide has the sequence represented as SEQ ID NO:106. In another embodiment, the polynucleotide has the sequence represented as SEQ ID NO:107. In another embodiment, the polynucleotide has the sequence represented as SEQ ID NO:108. In another embodiment, the polynucleotide has the sequence represented as SEQ ID NO:109. In another embodiment, the polynucleotide has the sequence represented as SEQ ID NO:112. In another embodiment, the polynucleotide has the sequence represented as SEQ ID NO:113. In another embodiment, the polynucleotide has the sequence represented as SEQ ID NO:114. In another embodiment, the polynucleotide has the sequence represented as SEQ ID NO:115. In another embodiment, the polynucleotide has the sequence represented as SEQ ID NO:124. In another embodiment, the polynucleotide has the sequence represented as SEQ ID NO:130. In another embodiment, the polynucleotide has the sequence represented as SEQ ID NO:132. In another embodiment, the polynucleotide has the sequence represented as SEQ ID NO:133. In another embodiment, the polynucleotide has the sequence represented as SEQ ID NO:134. In another embodiment, the polynucleotide has the sequence represented as SEQ ID NO:135. In another embodiment, the polynucleotide has the sequence represented as SEQ ID NO:136. In another embodiment, the polynucleotide has the sequence represented as SEQ ID NO:137. In yet another embodiment, the polynucleotide has the sequence represented as SEQ ID NO:138.

In a preferred embodiment, the polynucleotide contains a sequence selected from the group represented by SEQ ID NO:65, SEQ ID NO:66, SEQ ID NO:67, SEQ ID NO:68, SEQ ID NO:70, SEQ ID NO:71, SEQ ID NO:72, SEQ ID NO:73, SEQ ID NO:74, SEQ ID NO:76, SEQ ID NO:85, SEQ ID NO:86, SEQ ID NO:92, SEQ ID NO:95, SEQ ID NO:99, SEQ ID NO:105, SEQ ID NO:106, SEQ ID NO:107, SEQ ID NO:124, SEQ ID NO:130, SEQ ID NO:135, SEQ ID NO:136, SEQ ID NO:137 and SEQ ID NO:138. In another preferred embodiment, the polynucleotide contains a sequence selected from the group represented by SEQ ID NO:65, SEQ ID NO:66, SEQ ID NO:67, SEQ ID NO:70, SEQ ID NO:71, SEQ ID NO:72, SEQ ID NO:73, SEQ ID NO:74, SEQ ID NO:75, SEQ ID NO:76, SEQ ID NO:78 and SEQ ID NO:79.

In another aspect, the present invention includes a substantially isolated human polypeptide having immunomodulatory activity, where the polypeptide has a sequence encoded by a polynucleotide having a sequence represented by SEQ ID NO:65. In another embodiment, the polypeptide has a sequence encoded by a polynucleotide having a sequence represented by SEQ ID NO:66. In another embodiment, the polypeptide has a sequence encoded by a polynucleotide having a sequence represented by SEQ ID NO:67. In another embodiment, the polypeptide has a sequence encoded by a polynucleotide having a sequence represented by SEQ ID NO:68. In another embodiment, the polypeptide has a sequence encoded by a polynucleotide having a sequence represented by SEQ ID NO:70. In another embodiment, the polypeptide has a sequence encoded by a polynucleotide having a sequence represented by SEQ ID NO:71. In another embodiment, the polypeptide has a sequence encoded by a polynucleotide having a sequence represented by SEQ ID NO:72. In another embodiment, the polypeptide has a sequence encoded by a polynucleotide having a sequence represented by SEQ ID NO:73. In another embodiment, the polypeptide has a sequence encoded by a polynucleotide having a sequence represented by SEQ ID NO:74. In another embodiment, the polypeptide has a sequence encoded by a polynucleotide having a sequence represented by SEQ ID NO:76. In another embodiment, the polypeptide has a sequence encoded by a polynucleotide having a sequence represented by SEQ ID NO:78. In another embodiment, the polypeptide has a sequence encoded by a polynucleotide having a sequence represented by SEQ ID NO:79. In another embodiment, the polypeptide has a sequence encoded by a polynucleotide having a sequence represented by SEQ ID NO:82. In another embodiment, the polypeptide has a sequence encoded by a polynucleotide having a sequence represented by SEQ ID NO:83. In another embodiment, the polypeptide has a sequence encoded by a polynucleotide having a sequence represented by SEQ ID NO:85. In another embodiment, the polypeptide has a sequence encoded by a polynucleotide having a sequence represented by SEQ ID NO:86. In another embodiment, the polypeptide has a sequence encoded by a polynucleotide having a sequence represented by SEQ ID NO:88. In another embodiment, the polypeptide has a sequence encoded by a polynucleotide having a sequence represented by SEQ ID NO:92. In another embodiment, the polypeptide has a sequence encoded by a polynucleotide having a sequence represented by SEQ ID NO:95. In another embodiment, the polypeptide has a sequence encoded by a polynucleotide having a sequence represented by SEQ ID NO:98. In another embodiment, the polypeptide has a sequence encoded by a polynucleotide having a sequence represented by SEQ ID NO:99. In another embodiment, the polypeptide has a sequence encoded by a polynucleotide having a sequence represented by SEQ ID NO:100. In another embodiment, the polypeptide has a sequence encoded by a polynucleotide having a sequence represented by SEQ ID NO:104. In another embodiment, the polypeptide has a sequence encoded by a polynucleotide having a sequence represented by SEQ ID NO:105. In another embodiment, the polypeptide has a sequence encoded by a polynucleotide having a sequence represented by SEQ ID NO:106. In another embodiment, the polypeptide has a sequence encoded by a polynucleotide having a sequence represented by SEQ ID NO:107. In another embodiment, the polypeptide has a sequence encoded by a polynucleotide having a sequence represented by SEQ ID NO:108. In another embodiment, the polypeptide has a sequence encoded by a polynucleotide having a sequence represented by SEQ ID NO:109. In another embodiment, the polypeptide has a sequence encoded by a polynucleotide having a sequence represented by SEQ ID NO:112. In another embodiment, the polypeptide has a sequence encoded by a polynucleotide having a sequence represented by SEQ ID NO:113. In another embodiment, the polypeptide has a sequence encoded by a polynucleotide having a sequence represented by SEQ ID NO:114. In another embodiment, the polypeptide has a sequence encoded by a polynucleotide having a sequence represented by SEQ ID NO:115. In another embodiment, the polypeptide has a sequence encoded by a polynucleotide having a sequence represented by SEQ ID NO:124. In another embodiment, the polypeptide has a sequence encoded by a polynucleotide having a sequence represented by SEQ ID NO:130. In another embodiment, the polypeptide has a sequence encoded by a polynucleotide having a sequence represented by SEQ ID NO:132. In another embodiment, the polypeptide has a sequence encoded by a polynucleotide having a sequence represented by SEQ ID NO:133. In another embodiment, the polypeptide has a sequence encoded by a polynucleotide having a sequence represented by SEQ ID NO:134. In another embodiment, the polypeptide has a sequence encoded by a polynucleotide having a sequence represented by SEQ ID NO:135. In another embodiment, the polypeptide has a sequence encoded by a polynucleotide having a sequence represented by SEQ ID NO:136. In another embodiment, the polypeptide has a sequence encoded by a polynucleotide having a sequence represented by SEQ ID NO:137. In yet another embodiment, the polypeptide has a sequence encoded by a polynucleotide having a sequence represented by SEQ ID NO:138.

In a preferred embodiment, the polypeptide has a sequence encoded by a polynucleotide selected from the group consisting of SEQ ID NO:65, SEQ ID NO:66, SEQ ID NO:67, SEQ ID NO:68, SEQ ID NO:70, SEQ ID NO:71, SEQ ID NO:72, SEQ ID NO:73, SEQ ID NO:74, SEQ ID NO:76, SEQ ID NO:85, SEQ ID NO:86, SEQ ID NO:92, SEQ ID NO:95, SEQ ID NO:99, SEQ ID NO:105, SEQ ID NO:106, SEQ ID NO:107, SEQ ID NO:124, SEQ ID NO:130, SEQ ID NO:135, SEQ ID NO:136, SEQ ID NO:137 and SEQ ID NO:138. In another preferred embodiment, the polypeptide has a sequence encoded by a polynucleotide selected from the group consisting of SEQ ID NO:65, SEQ ID NO:66, SEQ ID NO:67, SEQ ID NO:70, SEQ ID NO:71, SEQ ID NO:72, SEQ ID NO:73, SEQ ID NO:74, SEQ ID NO:75, SEQ ID NO:76, SEQ ID NO:78 and SEQ ID NO:79.

In another aspect, the present invention includes a substantially-isolated polynucleotide having a sequence encoding a human homologue of yeast RAD50. In one embodiment, the polypeptide contains a polypeptide sequence encoded by a polynucleotide sequence selected from the group consisting of SEQ ID NO:54 and SEQ ID NO:55.

In a related aspect, the invention includes a substantially isolated human homolog of yeast RAD50 polypeptide. In one embodiment, the homolog polypeptide contains a polypeptide sequence encoded by a polynucleotide sequence selected from the group consisting of SEQ ID NO:54and SEQ ID NO:55.

Yet another aspect of the present invention includes a substantially-isolated polynucleotide having a sequence encoding a human homologue of Drosophila melanogaster Septin-2. In one embodiment, the polypeptide contains a polypeptide sequence encoded by the polynucleotide sequence represented by SEQ ID NO:97.

In a related aspect, the invention includes a substantially-isolated human Septin-2 homolog polypeptide. In one embodiment, the homolog polypeptide contains a polypeptide sequence encoded by the polynucleotide sequence represented by SEQ ID NO:97.

Still another aspect of the present invention includes a method of identifying the presence of activated T-cells in a sample containing a plurality of different cell types. The method includes performing a polymerase chain reaction amplification, where an aliquot of the sample (or homogenate/fraction thereof) serves as an amplification target and where the amplification is done using an oligonucleotide primer pair capable of selective amplification of a polynucleotide fragment having the sequence represented as SEQ ID NO:151. The amplification reaction generates an amplification product having a specific size, and the size of the amplification product is determined. The presence of amplification product of an expected size is indicative of the presence of activated T cells in the sample. In one embodiment, the oligonucleotide primer pair consists of primers having sequences represented as SEQ ID NO:149 and SEQ ID NO:150. In another embodiment, the sample is derived from adult tissue.

The invention also encompasses a method of identifying sequences encoding polypeptides having immunomodulatory activity. The method includes (i) selecting, by direct selection using sequences specific for region 5q23-31 of human chromosome 5, cDNA fragments isolated from tissues or cells expressing cytokines, (ii) grouping the fragments into "bins", where each bin represents cDNA fragments corresponding to a single gene or genetic locus, the grouping performed by sequencing the fragments and/or mapping the fragments to longer sequences derived from region 5q23-31 of human chromosome 5, and (iii) analyzing the tissue specificity of expression of transcripts corresponding to the fragments (transcripts from the gene or locus which the fragments represent). In one embodiment, the first step (step (i)) is performed using cDNAs obtained from cell lines and/or tissues expressing cytokines, such as activated T-cells. In another embodiment, the first step is performed using cDNAs obtained from a chromosome 5-specific activated T-cell cDNA library in lambda gt10; which was constructed using a kit from Life Technologies, Inc. and is deposited at Genelabs Technologies, Inc., Redwood City. In another general embodiment, the analyzing of tissue-specific expression is carried out using sequence-specific primers in a polymerase chain reaction amplification reaction containing target nucleic acids derived from tissues or cell lines of interest. Examples of tissues which may be used in determining the tissue specificity of expression include total embryo, fetal liver, fetal brain, fetal muscle, placenta, adult heart, adult muscle, adult liver, adult brain, adult pancreas, adult kidney, adult aorta, adult spleen, adult testis, adult bone marrow, resting T-cells and activated T-cells.

The present invention also includes a method of obtaining full-length sequences of genes or loci identified as having immunomodulatory activity. The method includes selecting a desired sequence identified in Table 1 and using the sequence to isolate overlapping clones. In one embodiment, such overlapping clones are isolated using rapid amplification of cDNA ends (RACE) PCR with cDNA obtained from tissues or cell lines of interest or from a cDNA or genomic DNA library. In another embodiment, the overlapping clones are isolated by direct hybridization screening of a cDNA or genomic DNA library made from, for example, T-cells, a lymphoma or a leukemia.

Also included in the invention is a method of identifying proteins having immunomodulatory activity. The method includes obtaining a full-length coding sequence of a gene represented by a sequence presented in Table 1 (e.g., as described above) and cloning the sequence into a recombinant expression vector. The resulting vector is then used to express recombinant polypeptides in selected host cells, such as E. coli.

The invention also includes a method of identifying small molecules that affect alter and/or modulate the activity of immunomodulatory proteins such as described above. The method includes assaying the effects of a polypeptide having immunomodulatory activity in the presence and absence of a test small molecule compound, and identifying the test compound as effective if the test compound is effective to significantly alter the effects of the polypeptide. In one embodiment, the small molecule compound is one of a plurality of such compounds present in a combinatorial library, such as one of a plurality of small molecules in a small molecule combinatorial library, or one of a plurality of peptides in a peptide combinatorial library.

These and other objects and features of the invention will be more fully appreciated when the following detailed description of the invention is read in conjunction with the accompanying drawings.

BRIEF DESCRIPTION OF THE FIGURES

FIG. 1 shows the location of primers SEQ ID NO:149 and SEQ ID NO:150 relative to sequence SEQ ID NO:151.

DETAILED DESCRIPTION OF THE INVENTION

I. Definitions

Figure 2:
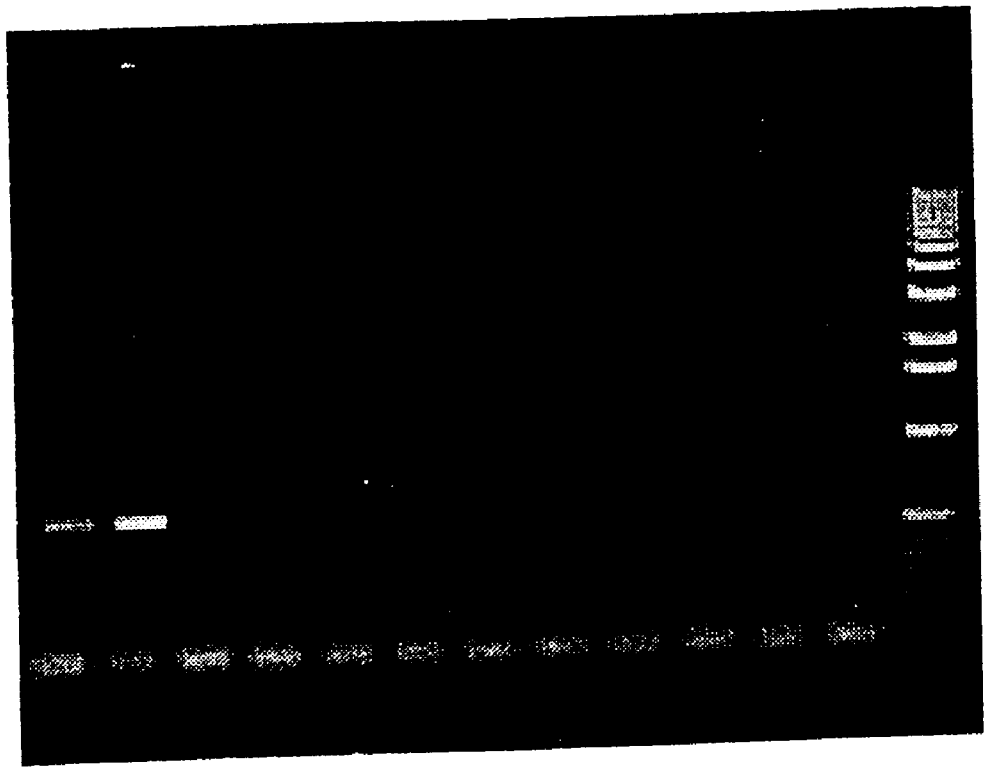
FIG. 2 is an image of an ethidium bromide-stained agarose gel, showing the expression pattern of SEQ ID NO:151.

"Substantially isolated" when used with respect to polynucleotide or polypeptides refers to the at least partial purification of such polynucleotides or polypeptides away from unrelated or contaminating components ((e.g., cellular components other than the specified polynucleotide or polypeptide, and polypeptides or polynucleotides having a sequence different from that of the selected polypeptide or polynucleotide. Methods and procedures for the isolation or purification of compounds or components of interest are described below (e.g., recombinant production of polypeptides having immunomodulatory activity).

Compounds or polypeptides having "immunomodulatory activity" are compounds or polypeptides that affect the regulation or function of the immune system. Examples of compounds or polypeptides having immunomodulatory activity include but are not limited to cytokines, which include growth factors, colony-stimulating factors, interleukins, lymphokines, monokines, interferons, chemokines and the like. Such polypeptides are typically secretory regulatory proteins that control the survival, growth, differentiation and effector function of tissues or cells. Polypeptides having immunomodulatory activity also include receptors for immunomodulatory compounds or polypeptides, including but not limited to, cytokine receptors, which include interleukin receptors, growth factor receptors, interferon receptors and receptors for other factors. Other examples of immunomodulatory compounds or polypeptides include transcription regulatory factors and signal transduction transmitters, such as NF-kB, interleukin regulatory factor 1 (IRF1), interleukin regulatory factor 2 (IRF2), G-proteins, signal transducers and activators of transcription (STATs), cell division control proteins, proteins involved in DNA repair and recombination, etc. that are expressed in human stromal or immune cells or tissues.

"Adult tissue" refers to tissue isolated from individuals older than about 1 year of age.

II. Cytokine Gene Cluster on Chromosome 5

Gene families tend to evolve by a process of tandemization, divergence, and in some cases, transposition. Linked families of genes are usually assumed to be together because they evolved from a common ancestor rather than being locked into a functional unit within a chromosomal region. There are numerous examples of linked genes that show strong homology to each other (e.g. HLA) but their are also many examples of genes that are strongly homologous but are scattered throughout the genome (e.g. tubulin genes).

Cytokine genes differ from these cases because they typically do not show strong homology at the nucleic acid sequence level, and should not necessarily be clustered in chromosomal regions. It is has been recognized herein, however, that there exist at least nine cytokine genes and at least ten receptor genes on the long arm of human chromosome 5 (e.g., Warrington, et al., 1992), suggesting that functionally-related molecules having little or no sequence homology may be situated together in a defined region of a chromosome.

III. Direct Selection and Analysis of Chromosome 5—Specific cDNA Sequences

Experiments performed in support of the present invention detail the generation of cDNA samples enriched for sequences from the 5q23-31 region of human chromosome 5. This region has been identified as containing a cluster of cytokine genes, including IL13, IL4, IL5, IRF1, IL3 and GM-CSF. Such immunomodulatory molecules may be involved in the development of certain cancers and immunodeficiencies, making them suitable targets for anti-cancer and immunotherapeutic drug candidates. The cDNA samples were derived from a variety of tissues, including human fetal brain and liver, adult bone marrow, leukemias, lymphomas, activated lymphocytes and cytokine-producing clones, as detailed in Example 1A. The samples were assayed for the presence of known cytokines as detailed in Example 1B using primers shown in Table 2. Results of these assays are shown in Table 3. Those samples showing increased expression of cytokines were combined to create "cDNA pools". The composition of the different pools is detailed in Example 1.

A similar approach may be employed to obtain cDNA samples enriched for various other selected sequences. For example, cDNA sequences upregulated during periods of increased synaptic transmission may be isolated from hippocampal slices following electrical stimulation of the slices. Such cDNA samples may be assayed for, e.g., cDNAs encoding other classes of selected molecules, such as protein kinases, phosphatases, neurotransmitters, hormones, and the like.

Pools containing relatively high levels of cDNAs encoding different cytokines (see Example 1, Table 3) were further processed using genomic "direct selection", as detailed in Examples 2 and 3. Here, yeast artificial chromosome (YAC) clones containing the 5q23-31 region of chromosome 5 were used to select cDNA that hybridized to sequences in that region. Analysis of approximately 3,000 cDNAs selected with the genomic region spanning 1.3 Mb of 5q23-31 revealed several hundred cDNA clones ranging from about 500. to about 800 bp in length. The sequences were further analyzed by mapping them to YAC clones containing fragments of the 5q23-31 region. About 79% of these clones were mapped to human chromosome 5 and starting YACs either by RT-PCR or Southern blot hybridization.

The data obtained from the physical mapping of the cDNAs to the starting YACs and chromosome 5-specific cosmids were used to group the cDNAs according to their location and partial overlap with one another, resulting in over 50 groups, or "bins", of cDNAs comprised of overlapping clones. Some of the selected cDNAs were also sequenced as described in Example 4 to facilitate placement into the bins. The results of these analyses are presented in Table 1, below.

TABLE 1

| Bin # | Consensus sequence | SEQ NO. | Type | Sequence length | Best BlastX homology score | Expression profile |
|---|---|---|---|---|---|---|
| 1 | Rad50.seq | 54 | con1 | ~5.7 kb | ~35% overall homology to *S. cerevisiae* Rad50: Score = 390, P = 3.8e-89 | Activated T-cells, testis, fetal liver, heart |
|  | 18.seq | 55 | con2 |  |  |  |
| 2 | Tc1.seq | 56 | alt | multiple isoforms: ~2.5–0.6 kb | ~90% overall homology to the Rat Brain Long Chain Acyl-CoA Synthetase | Activated T-cells, testis, fetal liver |
|  | Tc2.seq | 57 | alt |  |  |  |
|  | Tc3.seq | 58 | alt |  |  |  |
|  | TcA.seq | 59 | alt |  |  |  |
|  | TcB.seq | 60 | alt |  |  |  |
|  | TS.seq | 61 | alt |  |  |  |
|  | TS2.seq | 62 | alt |  |  |  |
|  | FL.seq | 63 | alt |  |  |  |
|  | FL2.seq | 64 | alt |  |  |  |
| 3 | G205a.seq | 65 | con1 | ~1.0 kb | homology to 1-PI 3-kinase: Score = 66, P = 0.024, (14/29). | Activated T-cells*, fetal liver |
|  | G205b.seq | 66 | con2 |  |  |  |
|  | G205c.seq | 67 | con3 |  |  |  |
| 4 | G221.seq | 68 | con | ~1.70 kb | homology to *S. cerevisiae* ZMS1 gene: Score = 75, P = 0.038, (19/44); homology to FGF: Score = 62, P = 0.74, (14/52) | Activated T-cells*, testis, fetal thymus |
| 5 | G238con.seq | 69 | con | ~1.4 kb | homology to drosophila Notch 2 gene: Score = 56, P = 0.00058, (12/29) | Activated T-cells, testis, fetal thymus |
| 6 | G229con.seq | 70 | con | ~2.76 kb | NSM | Activated T-cells** |
| 7 | G248.seq | 71 | con1 |  | NSM | Activated T-cells |
|  | G248a.seq | 72 | con2 |  |  |  |
|  | G248b.seq | 73 | con3 |  |  |  |
|  | G248c.seq | 74 | con4 |  |  |  |
|  | G220a.seq | 75 | con5 |  |  |  |
|  | G255.seq | 76 | con6 |  |  |  |
| 8 | G306.seq | 77 | con | ~0.65 kb | homology to *M. musculus* Modifier 3: Score = 67, P = 0.21 (12/17) |  |
| 9 | G256.seq | 78 | con | ~0.90 kb | homology to mouse formin 4 gene: Score = 71, P = 1.8e-09 | Activated T-cells** |
| 10 | G181.seq | 79 | con | ~1.40 kb | homology to *P. Aeroginosa* hypothetical 62.8 K protein: Score = 73, P = 0.33 (13/26) | Activated T-cells** |
| 11 | G257.seq | 80 | con | ~0.70 kb | homology to *M. Sativa* NADH-glutamate synthase: Score = 69, P = 0.33 (13/26) | Lung, activated T-cells, brain, liver and heart |
| 12 | E2.seq | 81 | con1 | ~0.7 kb; | NSM | E2: kidney, activated T-cells, fetal liver and muscle, bone marrow; E9: activated T-cells, fetal liver, |
|  | E9f.seq | 82 | con2 | E9: |  |  |
|  | E9r.seq | 83 | con3 | ~1.0 kb; |  |  |
|  | G123con.seq | 84 | con4 | ~0.32 kb |  |  |

TABLE 1-continued

| Bin # | Consensus sequence | SEQ NO. | Type | Sequence length | Best BlastX homology score | Expression profile |
|---|---|---|---|---|---|---|
| | | | | | | testis, brain, kidney, small intestine |
| 13 | A116con.seq | 85 | con | ~3.1 kb | NSM | Activated T-cells, placenta, fetal liver and muscle, kidney, heart, bone marrow |
| 14 | A25con.seq | 86 | con | ~1.9 kb | NSM | Activated T-cells, fetal liver and muscle, placenta, kidney, bone marrow |
| 15 | A46.seq | 87 | con | ~0.85 kb | NSM | fetal liver, kidney and muscle, placenta, activated T-cells, heart, bone marrow |
| 16 | A66.seq | 88 | con | ~0.68 kb | NSM | activated T-cells, fetal liver, placenta, heart, bone marrow |
| 17 | A42.seq | 89 | con | ~0.57 kb | homology to rabbit T-cell receptor, beta chain: Score = 59, P = 7.9–0.6 (21/60) | Activated T-cells, fetal muscle, placenta, heart, kidney |
| 18 | A76con.seq | 90 | con | ~1.044 bp | homology to ATP synthase: Score = 67, P = 5.4–0.6 (21/60) and ubiquinone: Score = 63, P = 8.8–0.6 (11/28) | Activated T-cells, placenta, heart |
| 19 | E105con.seq | 91 | con | ~1.7 kb | homology to 3 ESTs | |
| 20 | G180con.seq | 92 | con | ~0.93 kb | | |
| 21 | G310con.seq G326con.seq G164con.seq | 93 94 95 | con1 con2 con3 | ~2.10 kb ~1.38 kb ~1.10 kb | NSM | G310: lung, liver, brain, small intestine, testis, activated T-cells; G326: lung, liver, brain, thymus, activated T-cells; G164: lung, liver, brain, thymus, ovary, activated T-cells; |
| 22 | G65.seq | 96 | con | ~2.1 kb | ~60% aa homology to human and chick propyl 4-hydroxylase, procollagen-proline dioxygenase, gamma-butyrobetaine, 2-oxoglutarate dioxygenase: Score = 797, P = 5.1e-164 | |
| 23 | CDC3.seq | 97 | con | ~1.2 kb (partial sequence) | homology to Drosophila Septin-2; ~50% aa homology | |

TABLE 1-continued

| Bin # | Consensus sequence | SEQ NO. | Type | Sequence length | Best BlastX homology score | Expression profile |
|---|---|---|---|---|---|---|
| | | | | | to human and yeast cell division control proteins, such as CDC3 and CDC10: Score = 196, P = 2.9e-63 | |
| 24 | G42con.seq | 98 | con | ~0.5 kb | NSM | |
| 25 | G105con.seq | 99 | con | ~0.64 kb | NSM | Activated T-cells, fetal liver, kidney, lung, small intestine, heart, brain, spleen and testis |
| 26 | G98con.seq | 100 | con | ~0.41 kb | NSM | |
| 27 | G73con.seq | 101 | con | ~0.4 kb | ~76% homology to human ubiquinol cytochrome C reductase: Score = 338, P = 6.3e-45 | Ubiquitous |
| 28 | G89con.seq | 102 | con | ~2.2 kb (partial sequence) | homology to *X. laevis* apical plasma membrane protein: Score = 149, P = 2.7e-35 | Prostate, brain, kidney, liver, small intestine, placenta |
| 29 | G102.seq | 103 | con | ~0.4 kb | homology to human ataxin-1 gene: Score = 67, P = 0.2 (13/24) | |
| 30 | G57.seq | 104 | con | ~0.4 kb | NSM | |
| 31 | G108.seq | 105 | con | ~0.25 kb | NSM | Activated T-cells, small intestine |
| 32 | G127.seq | 106 | con | ~0.42 kb | NSM | Activated T-cells, fetal liver, heart, kidney, brain, spleen, placenta, testis, small intestine |
| 33 | G86.seq | 107 | con | ~0.28 kb | NSM | Activated T-cells, brain |
| 34 | G78.seq H993.seq | 108 109 | con1 con2 | ~0.5 kb | NSM | |
| 35 | G38a.seq | 110 | con | ~0.5 kb | NSM | |
| 36 | H90.seq | 111 | con | | NSM | |
| 37 | G66.seq H973.seq | 112 113 | con1 con2 | | NSM | |
| 38 | H505.seq H989.seq | 114 115 | con1 con2 | | NSM | |
| 39 | E118con.seq | 116 | con | ~0.82 kb | ~95% homology to several ESTs in Genbank | Activated T-cells, fetal muscle and liver, heart, kidney, brain, muscle, aorta, placenta |
| 40 | E69f.seq E69r.seq | 117 118 | con1 con2 | ~0.9 kb | 100% homology to human eF-1 alpha gene | |
| 41 | E36.seq | 119 | con | | NSM | |
| 42 | A104f.seq A104r.seq | 120 121 | con1 con2 | ~0.8 kb | 100% homology to human serine protease B gene | |
| 43 | H622.seq | 122 | con | ~0.59 kb | homology to human gamma-G globin gene: Score 348, P = 7.2–45, (67/70) | |

TABLE 1-continued

| Bin # | Consensus sequence | SEQ NO. | Type | Sequence length | Best BlastX homology score | Expression profile |
|---|---|---|---|---|---|---|
| 44 | G61con.seq | 123 | con | ~0.7 kb | NSM | |
| 45 | G45.seq | 124 | con | ~0.29 kb | | Lung, kidney, brain, thymus, fetal liver and brain, activated T-cells |
| 46 | G3con.seq | 125 | con | ~1.26 kb | NSM | |
| 1a | G30.seq | 126 | con | ~0.32 kb | NSM | Lung, brain, kidney, heart, muscle, liver, placenta, small intestine, activated T-cells |
| 2a | G32.seq | 127 | con | ~0.38 kb | NSM | Ubiquitous |
| 3a | G37.seq | 128 | con | ~0.4 kb | NSM | |
| 4a | G39.seq | 129 | con | ~0.43 kb | NSM | Kidney, fetal liver, activated T-cells |
| 5a | G75.seq | 130 | con | ~0.4 kb | NSM | Kidney, fetal liver, small intestine, activated T-cells |
| 6a | H100.seq | 131 | con | ~0.37 kb | 100% to known human H19 gene | |
| 7a | H414f.seq | 132 | con | ~0.8 kb | NSM | |
| 8a | H631.seq | 133 | con | ~0.5 kb | NSM | |
| 9a | G93.seq | 134 | con | ~0.4 kb | NSM | |
| 10a | G115a G115b G115c.seq | 135 136 137 | con1 con2 con3 | ~2.0 kb (partial sequence) | homology to drosophila homeotic Cad gene: Score = 69, P = 0.12 (12/19) | Kidney, lung, liver, brain, heart, placenta, spleen, small intestine, testis, muscle, activated T-cells, fetal liver |
| 11a | G122.seq | 138 | con | 0.25 kb | homology to human heparin-binding growth factor: Score = 57, P = 0.26, (11/26) | Activated T-cells, spleen, fetal liver |
| 12a | G329f.seq | 139 | con | ~1.00 kb | 100% homology to human HSP70 gene | |
| 13a | E67.seq | 140 | con | ~2.57 kb | ~90% homology to the human ubiquitin gene: Score = 460, P = 1.8e-119 | |
| 14a | E94.seq | 141 | con | 0.63 kb | homology to lilium longiformium HSP70 gene: Score = 62, P = 0.48 (12/28) | |

*expression in tissue at least 10x stronger that other tissues listed
**expression profile tested using only samples containing activated T-cells (no other tissues tested)

The bin number, name, type, SEQ ID NO: and approximate size of each sequence are provided in the first set of columns. The "type" of sequence is either (i) a single contiguous consensus sequence derived from the overlapping cDNA clones that comprise that bin ("con"), (ii) two or more non-overlapping consensus sequences within a bin (e.g., "con1", "con2", . . . ), representing consensus sequences covering, e.g., a 3' and a 5' portion of a region that has not been completely sequenced, or (iii) alternatively-spliced variants ("alt") derived from the same "parent" sequence.

All sequences identified in Table 1 were analyzed by subjecting them to a "BLASTX" homology search against a protein sequence database (PIR+SWISS-PROT). The results of these analyses are also presented in Table 1. In cases where the BLASTX search did not yield a significant match, the cell in the Table is labeled "NSM" (no significant matches).

The last column of Table 1 presents a summary of experiments performed to address the expression patterns of the various cDNAs. Most of these experiments were performed using RT-PCR with primers specific for the consensus sequence representing each bin. The details of the experimental methods are presented in Example 6B. Primers specific for the sequences to be amplified were constructed using standard methods. The primers were selected such that the expected amplification products were typically between 200 and 1000 bp in length. The following tissues were used for the RT-PCR reactions: total embryo (6, 8, 12 weeks of gestation), fetal liver, fetal brain, fetal muscle, placenta, adult heart, adult muscle, adult liver, adult brain, adult pancreas, adult kidney, adult aorta, adult spleen, adult testis, adult bone marrow, JY B-cell line, resting T-cells and activated T-cells. The RT-PCR expression analyses revealed that many of the novel, previously uncharacterized cDNAs, were expressed in activated T-cells, suggesting that they may encode novel immunomodulatory molecules.

Many of the consensus sequences presented above were arrived at by analysis of a number of overlapping clones. In some cases, the clones overlapped only near their ends and the sequence between the overlaps was derived from a single cDNA. In such cases and some others, the consensus sequence may contain alternatively-spliced sequences from the same gene, even though different alternatively-spliced transcripts derived from the same region of the gene were not detected. Such alternatively-spliced sequences in the consensus sequences may have different tissue specificities, and thus give rise to different patterns of expression, depending on which portion of the cDNA is being amplified. In cases where different patterns of expression for cDNAs that were part of the same consensus sequence were detected, the "expression profile" in Table 1 above lists all the tissues in which expression of any of the cDNAs constituting the bin or consensus sequence was detected, unless indicated otherwise.

One such difference in expression profiles was observed with the cDNAs comprising bin 13 (A116con.seq; SEQ ID NO:85). A series of experiments designed to detect expression profiles of various cDNAs which comprised SEQ ID NO:85 yielded the results shown in Table 1. However, as described in Example 9 and illustrated in FIG. 2, experiments using primers SEQ ID NO:149 and SEQ ID NO:150, designed to amplify the indicated portion of the sequence shown in FIG. 1 (SEQ ID NO:151), consistently detected this transcript only in activated T-cells. Accordingly, amplification of this DNA fragment may be used as a sensitive method to detect the presence of activated T-cells.

The cDNAs identified as described above may also be used to identify the chromosome region from which they are derived, using standard mapping techniques, as detailed, for instance, in Example 5. Such mapping information may be used, for example, to identify clones which map to regions implicated in genetic diseases or disorders.

Physical mapping of selected cDNAs can be done by a variety of meats. A particularly rapid method is PCR mapping to the YAC clones and natural or radiation hybrid panels that carry whole human chromosomes 5 or its portions. Such experiments preferably include appropriate controls, such as no genomic DNA, total genomic DNA, rodent genomic DNA that is present in radiation hybrids, etc. Another approach employs Southern blot hybridization of the YAC clones or genomic DNA, and isolation of chromosome 5-specific cosmids or any other genomic clones, such as bacteriophage 1. (P1) or bacterial artificial chromosomes (BACs), with cDNA as a probe.

Some of the nucleotide sequences presented in Table 1 do not include the entire coding region of the gene to which they correspond. In such cases, the remaining sequences may be obtained by one of skill in the art using the sequence information and teachings contained in the present specification combined with standard molecular techniques. For example, the cDNA clones described herein, or fragments thereof, may be used to screen a cDNA library constructed from, e.g., human T-cells using standard methods (e.g., Ausubel, et al., 1988). Such libraries are commercially available, for example, from Clontech (Palo Alto, Calif.). Full length clones may also be obtained by similar screening of cDNA pools generated as described herein.

Using the sequence information disclosed herein, one of skill in the art employing standard techniques may derive near full length cDNAs, express and purify protein products of such cDNAs, and confirm function using, e.g., gene knock-out experiments. This information may then be used to develop specific assay systems to test for biological activities and to screen for therapeutic compounds that modulate those activities.

IV. Characterization of Exemplary cDNA Sequences

Expression of specific sequences was assessed using Northern blot analyses, as detailed in Example 6A. The Northern analyses were performed with cDNA fragments representing bins 1, 2, 3, 13, 16, 18, 22, 23, and 28, on blots generated essentially as described in Example 6A or obtained commercially, typically from Clontech (Palo Alto, Calif.).

A. Human Acyl-CoA Synthetase

Fragments derived from the Human Acyl-CoA synthetase gene (SEQ ID NO:59) were used to assess the expression pattern of this gene using Northern blot in the following adult human tissues: spleen, thymus, prostate, testis, ovary, small intestine, colon and leukocytes. The experiments were also performed using fetal brain, fetal lung, fetal liver and fetal kidney. A prominent band was seen in all tissues at approximately 1.8 kb. In addition, a 2.8 kB form was detected in testis, prostate, fetal liver and activated T-cells.

The expression pattern of human Acyl-CoA synthetase is different from that of the rat brain Acyl-CoA synthetase, where two predominant transcripts of 2.9 and 6.3 kb are observed predominantly in brain and heart, and to some extent, in adrenal tissue (Fujino and Yamamoto, 1992). Based on these data, it is suggested that the human Long-chain acyl-CoA synthetase (LACS) gene described herein may be transcribed from two different promoters and that it's alternative processing represents a ubiquitous mechanism for generation of multiple protein isoforms or tissue-specific regulation. LACS from different species have been isolated and shown to play a critical role in fatty acid metabolism, acylation of many membrane proteins, and signal transduction.

The above results suggest that sequences derived from the human Acyl-CoA Synthetase gene may be used as a marker for testis tissue. Further, the promoters from the human LACS gene, which may be isolated using standard methods (e.g., Ausubel, et al., 1988), may be used to target expression of heterologous genes in testis tissue. Such expression may desirable, for example, in gene therapy approaches to testicular cancer.

B. Human RAD50 Homolog

Northern experiments were also performed using probes derived from sequences (SEQ ID NO:54 and SEQ ID NO:55) from the human homologue of yeast Rad50. A non-coding 3'-flanking fragment of the gene corresponding to nucleotides 4333–5567 of SEQ ID NO:54 was used to probe a Northern Blot containing RNA derived from the same set of adult tissues as described above. mRNA species of 1.9 and 0.85 kb were detected in all tissues tested, with the strongest expression in testis, ovary and small intestine. Uniformity of RNA loading was confirmed using a beta-actin probe.

Similar experiments employing a probe corresponding to nucleotides 417–4353 of SEQ ID NO:54 revealed two mRNA species. A stronger signal was observed at about 5.8 kb and much lower signal was detected at about 6.5 kb in all tissues, with strongest expression in testis. The results of RT-PCR and Northern blot analyses taken together confirmed expression of the human gene in activated T-cells, B-cells, placenta and multiple fetal tissues, including fetal liver. Genomic equivalent of this gene is about 100 kb.

In yeast, Rad50 encodes major and minor transcripts of 4.2 and 4.6 kb in length, respectively (Raymond and Kleckner, 1993). Steady-state levels of both transcripts increase during meiosis, reaching maximal levels midway during meiotic prophase. Yeast RAD50 appears to be involved in DNA repair. It is required during vegetative growth for recombinational repair of double strand breaks and for efficient mating type switching, a direct recombination event promoted by a site-specific double strand break. Most *S. cerevisiae* mutants of rad50 are deficient in repair of damage induced by X rays and in meiotic recombination.

The polypeptide predicted for *S. cerevisiae* Rad50 protein is 153 kDa (1312 aa) (Alani, et al., 1989). The protein contains an amino-terminal ATP-binding domain. Inactivation of this site by point mutations results in a null phenotype, and primary defects in meiosis. The remainder of the protein includes two long segments of heptad repeat sequence diagnostic of regions capable of forming alpha-helical coiled coils, one of which is similar to the S-2 domain of the myosin heavy chain. Since some mutations in the protein affect meiotic recombination but not the repair, it is likely that the protein has domains with different roles.

It is contemplated that the human homologue of Rad50 described herein (e.g, as represented by SEQ ID NO:144) plays a role in human DNA repair and may be a target for cancer related therapeutics. For example, since attenuating the function of Rad50 gene products may sensitize cells to DNA damage, they may be targets for therapeutic interventions that rely on DNA damage to differentially inhibit tumor survival.

C. Human Septin-2 Homolog

A fragment corresponding to nucleotides 203–1464 of SEQ ID NO:97 was used to probe a Northern blot containing RNA from the same adult tissues listed above. The probe identified a faint band at 4.6 kb in lymph node, thymus, appendix, bone marrow and fetal liver. A near full-length cDNA containing ~4.6 kb of the human gene was isolated using Marathon RACE using primer designed based on sequence SEQ ID NO:97. The cDNA encodes a protein that has higher homology to Septin-2 than to CDC3 and that is 40 aa longer than Drosophila Septin-2.

In yeast, mutants of cell division cycle (cdc) gene 3 (cdc3) are incapable of forming an F-actin contractile ring. It is now believed that cdc3 encodes a profilin that plays essential in cytokinesis, by catalyzing the formation of the F-actin contractile ring (Balasubramanian, et al., 1994)

In Drosophila, Septint-2 is present at the bud neck during cell division, and is required for cytokinesis: in pnut mutants, imaginal tissues fail to proliferate and instead develop clusters of large, multinucleate cells. Pnut interacts with a gene required for neuronal fate determination in the compound eye.

Computer analysis of the human septin protein described herein has identified several important motifs, such as NTP-binding site (ATP/GTP-binding loop) at N-terminus, a coiled-coil region and a bipartite nuclear targeting site at C-terminus. These data suggest that its role in signal transduction to the nucleus may be associated with cell division. The coiled-coil region may be involved in the formation of protein complexes and in chromosome condensation and disjunction in the cell cycle.

In view of septin-2's involvement in cell proliferation, it is contemplated that the human Septin-2 homolog, peptide represented by SEQ ID NO:143, may be a target for anti-cancer therapies and methods. Further, monitoring septin-2 expression by quantitative RT-PCR can be used as a diagnostic tool for measuring proliferative potential of selected cell types.

D. Other Genes and Methods

It will be understood that human cDNA, sequences isolated as described herein may be characterized using any of a number of assays known to those of skill in the art, in addition to the expression assays detailed above. For example, functional assays particularly advantageous for the characterization of immunomodulatory molecules (i.e., assays which may be used to further characterize the immunomodulatory activity of polypeptide compositions detailed herein) include proliferation assays (e.g., as described in Example 8), as well as assays based on the stimulation of expression of specific proteins in cell lines responsive to the immunomodulatory molecules (e.g., cytokines) under study (e.g., Thorpe, et al., 1992; Wadhwa, et al., 1992). Specifically, compounds or polypeptides which inhibit, e.g., T-cell proliferation, may be characterized as immunosuppressants, whereas compounds or polypeptides which stimulate, e.g., T-cell proliferation, may be identified as immunostimulants.

In the case of polypeptides comprising receptors for, e.g., other immunomodulatory compounds, such as cytokines, standard methods may be employed to express the receptors in a suitable host cell suitable for additional experiments, such as binding assays or physiological experiments.

Other methods of assaying expression may also be employed in the characterization of novel cDNA sequences isolated as described herein. For example, in situ hybridization may be used to perform cellular localization in tissues having comprised of distinct cell types. The cDNA sequences presented herein may also be used to produce proteins (e.g., by cloning the sequences into an expression vector; Ausubel, et al., 1988). Such proteins may in turn may be employed to generate antibodies using standard methods (e.g., Harlow, et al., 1988) to localize the gene products at the cellular and sub-cellular levels.

V. Utility

Methods and compositions of the present invention are useful in a number of applications. For example, they may be employed in cell typing applications. In this aspect, the invention includes a method of identifying the presence of activated T-cells in a sample containing a plurality of different cell types. Experiments performed in support of the present invention. The method includes performing a polymerase chain reaction amplification which employs an aliquot of the sample or an extract thereof as the amplification target. The reaction is conducted using standards PCR conditions (Mullis, 1987; Mullis, et al., 1987) with oligonucleotide primers capable of selective amplification of a polynucleotide fragment having the sequence SEQ ID NO:151, to generate an amplification product having a specific size.

The selection of regions of a sequence suitable for serving as templates for PCR primer design is well known in the art (e.g., Innis, et al., 1990). In fact computer programs designed specifically for this purpose are commercially-available (e.g., "OLIGO" primer analysis software, NCBI, Inc., Plymouth, Minn.). An exemplary primer pair for such an amplification consists of primers having sequences SEQ ID NO:149 and SEQ ID NO:150.

The size of the amplification is then determined using, for example, agarose or polyacrylamide gel electrophoresis (see, e.g., Ausubel, et al., 1988), and the observed size is compared with the expected size. The detection of amplification product corresponds to the existence of activated T-cells in the sample. The amount of amplification product may be correlated with the number of activated. T-cells using a quantitative PCR approach (e.g., Piatak, et al., 1993; Vandevyver, et al., 1995).

The identification of activated T-cells in a sample is useful in, e.g., the diagnosis of diseases affecting activated T-cells or T-cell activation, such as AIDS, rheumatoid arthritis, asthma, Cystic fibrosis, atherosclerosis, ulcerative colitis, asthma and severe allergies.

Another utility enabled by the present disclosure is a method of identifying sequences encoding polypeptides having immunomodulatory activity. The method includes (i) selecting, by direct selection using sequences specific for region 5q23-31 of human chromosome 5, cDNA fragments isolated from tissues or cells expressing cytokines, (ii) grouping the fragments into bins, where each bin represents cDNA fragments corresponding to a single gene or genetic locus, the grouping performed by sequencing the fragments and/or mapping the fragments to longer sequences derived from region 5q23-31 of human chromosome 5, and (iii) analyzing the tissue specificity of expression of transcripts corresponding to the fragments (transcripts from the gene or locus which the fragments represent). In one embodiment, the first step is performed using cDNAs obtained from cell lines and/or tissues expressing cytokines, such as activated T-cells. In another embodiment, the first step is performed using cDNAs obtained from a chromosome 5-specific activated T-cell cDNA library in lambda gt10, which was constructed using a kit from Life Technologies, Inc. and is deposited at Genelabs Technologies, Inc., Redwood City. In another embodiment, the analyzing of tissue-specific expression is carried out using sequence-specific primers in a polymerase chain reaction amplification reaction containing target nucleic acids derived from tissues or cell lines of interest. Tissues which may be used in determining the tissue specificity of expression include total embryo, fetal liver, fetal brain, fetal muscle, placenta, adult heart, adult muscle, adult liver, adult brain, adult pancreas, adult kidney, adult aorta, adult spleen, adult testis, adult bone marrow, resting T-cells and activated T-cells.

The teachings of the present disclosure may also be employed in a method of obtaining full-length sequences of genes or loci identified as having immunomodulatory activity. The method includes selecting a desired sequence identified in Table 1 and using the sequence to isolate overlapping clones. In one embodiment, such overlapping clones are isolated using rapid amplification of cDNA ends (RACE) PCR with cDNA obtained from tissues or cell lines of interest or from a cDNA or genomic DNA library. In another embodiment, the overlapping clones are isolated by direct hybridization screening of a cDNA or genomic DNA library made from, for example, T-cells, a lymphoma or a leukemia.

As another example of a utility, the present invention includes a method of identifying proteins having immunomodulatory activity. The method includes obtaining a full-length coding sequence of a gene represented by a sequence presented in Table 1 (e.g., as described above) and cloning the sequence into a recombinant expression vector. The resulting vector is then used to express recombinant polypeptides in selected host cell's, such as E. coli. Expression vectors such as described above typically contain control sequences, such as sequences containing promoter regions, enhancer elements, and the like, which are compatible with the selected host cell. These control sequences are operably linked to the insert sequence such that the insert sequence can be expressed in the selected host cell.

One example of an expression vector for recombinant production of latency-associated polypeptides is the plasmid pGEX (Smith, et al., 1985, 1988) and its derivatives ((e.g., the pGEX series from Pharmacia Biotech, Piscataway, N.J.). These vectors express the polypeptide sequences of a cloned insert fused in-frame with glutathione-S-transferase. Recombinant pGEX plasmids can be transformed into appropriate strains of E. coli and fusion protein production can be induced by the addition of IPTG (isopropyl-thio galactopyranoside). Solubilized recombinant fusion protein can then be purified from cell lysates of the induced cultures using glutathione agarose affinity chromatography according to standard methods (Ausubel, et al., 1988).

Alternatively, affinity chromatography may also be employed for isolating β-galactosidase fusion proteins, such as those produced by cloning latency-associated polypeptide sequences in lambda gt11. The fused protein is isolated by passing cell lysis material over a solid support having surface-bound, anti-β-galactosidase antibody.

Other suitable expression systems include a number of bacterial expression vectors, such as lambda gt11 (Promega, Madison Wis.), pGEX (Smith, et al. ), and pBS (Stratagene, La Jolla Calif.) vectors; yeast expression systems, such as the Pichia expression kit from Invitrogen (San Diego, Calif.); baculovirus expression systems (Reilly, et al.; Beames, et al.; Clontech, Palo Alto Calif.); and mammalian cell expression systems (Clontech, Palo Alto Calif.; Gibco-BRL, Gaithersburg Md.).

A number of features can be engineered into the expression vectors, such as leader sequences which promote the secretion of the expressed sequences into culture medium. The recombinantly produced polypeptides are typically isolated from lysed cells or culture media.

Isolated recombinant polypeptides produced as described above may be purified by standard protein purification procedures, including differential precipitation, molecular sieve chromatography, ion-exchange chromatography, isoelectric focusing, gel electrophoresis and affinity chromatography. Protein preparations can also be concentrated by, for example, filtration (Amicon, Danvers, Mass.).

In addition to recombinant methods, latency-associated proteins or polypeptides may be chemically synthesized using methods known to those skilled in the art.

Polypeptides obtained as described above may be further evaluated by methods known in the art of cytokines and interleukins. For example, the polypeptides may be tested in functional assays, such as cell proliferation assays and assays designed to monitor the activation of gene expression in response to cytokine stimulation as described above.

It is further contemplated that polypeptides identified as having immunomodulatory activity may be employed in therapeutic applications to augment, affect and/or correct the functioning of the immune system in a subject in need of such treatment.

In another example of the utility of the present invention, the teachings herein may applied in a method of identifying small molecules that affect alter and/or modulate the activity of immunomodulatory proteins such as described above. The method includes assaying the effects of a polypeptide having immunomodulatory activity in the presence and absence of a test small molecule compound, and identifying the test compound as effective if the test compound is effective to significantly alter the effects of the polypeptide. In one embodiment, the small molecule compound is one of a plurality of such compounds present in a combinatorial library, such as one of a plurality of small molecules in a small molecule combinatorial library, or one of a plurality of peptides in a peptide combinatorial library. Small molecule compounds include, but are not limited to, peptides, macromolecules, small molecules, chemical and/or biological mixtures, and fungal, bacterial, or algal extracts. Such compounds, or molecules, may be either biological, synthetic organic or even inorganic compounds, and maybe obtained from a number of sources, including pharmaceutical companies and specialty suppliers of libraries (e.g., combinatorial libraries) of compounds.

The following examples illustrate but in no way are intended to limit the present invention.

Materials and Methods

Unless otherwise indicated, restriction-enzymes and DNA modifying enzymes were obtained from New England Biolabs (Beverly, Mass.) or Boehringer Mannheim (Indianapolis, Ind.). Nitrocellulose paper was obtained from Schleicher and Schuell (Keene, N.H.). Materials for SDS-polyacrylamide gel electrophoresis (SDS-PAGE) were obtained from Bio-Rad Laboratories (Hercules, Calif.). Other chemicals were purchased from Sigma (St. Louis, Mo.) or United States Biochemical (Cleveland, Ohio).

A. Buffers and Media

Phosphate-buffered saline (PBS)
  10×stock solution, 1 liter:
    80 g NaCl
    2 g KCl
    11.5 g $Na_2HPO4-7H_2O$
    2 g $KH_2PO_4$
  Working solution, pH 7.3:
    137 mM NaCl
    2.7 mM KCl
    4.3 mM $Na_2HPO_4-7H_2O$
    1.4 mM $KH_2PO_4$
SSC (sodium chloride/sodium citrate), 20×
    3 M NaCl (175 g/liter)
    0.3 M $Na_3Citrate-2H_2O$ (88 g/liter)
    Adjust pH to 7.0 with 1 M HCl
SSPE (sodium chloride/sodium phosphate/edta), 20×
    3.0 M NaCl
    0.20 M $NaH_2PO_4$
    20 mM EDTA, pH 7.4
Tris/EDTA Buffer (TE)
    10 mM Tris-Cl, pH as indicated
    1 mM EDTA, pH 8.0
AHC Medium and Plates (ura$^-$, trp$^-$)
    1.7 g yeast nitrogen base without amino acids and without ammonium sulfate (Difco Laboratories, Detroit, Mich.).
    5 g ammonium sulfate.
    10 g casein hydrolysate-acid, salt-free and vitamin-free (United States Biochemical, Cat. #12852; Cleveland, Ohio).
    50 ml (for medium) or 10 ml (for plates) of 2 mg/ml adenine hemisulfate (Sigma Chemical, Cat. #A-9126, St. Louis, Mo.).
    Dissolve in a final volume of 900 ml $H_2O$, adjust pH to 5.8.
    Autoclave 30 min, then add 100 ml sterile 20% (w/v) glucose. For AHC plates, add 20 g agar prior to autoclaving. Store at 4° C. for $\leq 6$ weeks.
Denhardt solution, 100×
    10 g Ficoll 400
    10 g polyvinylpyrrolidone
    10 g bovine serum albumin (Pentex Fraction V, Miles Laboratories, Kankakee, Ill.)
    $H_2O$ to 500 ml.
    Filter sterilize and store at −20° C. in 25-ml aliquots

EXAMPLE 1

Construction of cDNA Pools for Use in Direct Selection

Complementary DNA (cDNA) was prepared using standard methods from tissues and cell lines that expressed or were likely to express sufficient amounts of messenger RNA (mRNA) encoding proteins of interest. cDNA samples, from several sources were sometimes grouped into "cDNA pools". For example, ionomycin-stimulated T cells, T cell clones, and T lineage lymphomas were found be the best mRNA source for construction of a polymerase chain reaction (PCR)-amplifiable cDNA pool for direct selection due to high levels of corresponding cytokines expressed (first eight samples in Table 3, below). Similarly, a hybrid cDNA pool, termed pool #1, was constructed using mRNA isolated from a mixture of several activated T-cell clones and lymphomas (obtained from David Lewis, University of Washington, Seattle; Lewis, et al., 1988).

A complex primary cDNA pool, termed pool #2, was constructed from human fetal and adult tissues, including fetal brain and liver, adult bone marrow, and activated lymphocytes, as well as the following cytokine-producing cell lines, which, unless otherwise indicated, were obtained form the American Type Culture Collection (ATCC), Rockville Md.: A-10 cells (T cell clone), Jurkat cells. (ATCC TIB-152), CEM cells (ATCC CCL-119), HUT-78 cells (ATCC TIB-161), JM cells. (ATCC CRL-8294), Molt-4 cells (ATCC accession number CRL1582) and NG-1 cells.

Prior to isolating mRNA from "activated" T-cell samples, the cells were grown at $5 \times 10^6$ cells/ml in RPMI medium (GIBCO/BRL Life Technologies) supplemented with 5% human AB serum as previously described (Georgopoulos, et al., 1990) and activated using 50 ng/ml phorbol myristate acetate (PMA, Sigma, St. Louis, Mo.) in combination with either 25 $\mu$g/ml concanavalin A (Con A) (Pharmacia, Piscataway, N.J.) or 0.5 $\mu$M ionomycin (Calbiochem-Behring, San Diego, Calif.).

A. Cell Isolation and Synthesis of cDNA

1. Isolation of Primary T Cells and Thymocytes. Circulating adult T cells and thymocytes were isolated as previously described (Georgopoulos, et al., 1990) by Ficoll-Hypaque density gradient centrifugation and treated with CD4 Lymphokwik (One Lambda, Los Angeles, Calif.), a mixture of complement and monoclonal antibodies (mAb) directed against non-T-lineage markers and the CD8 surface antigen, following the manufacturer's instructions. The final purity of each T-lineage cell population was consistently >95% based on flow cytometric analysis after staining with appropriate mAbs.

2. Cell Activation. Cells were activated at 5×10⁶/ml in RPMI medium supplemented with 5% human AB serum as previously described (Georgopoulos, et al., 1990) using 50 ng/ml phorbol myristate acetate (PMA; Sigma, St. Louis, Mo.) in combination with either 25 $\mu$g/ml concanavalin A (ConA) (Pharmacia, Piscataway, N.J.), 0.5 $\mu$M ionomycin (Calbiochem-Behring, San Diego, Calif.), or 2.5 $\mu$g/ml PHA (Sigma, St. Louis, Mo.).

3. RNA Isolation. Cell or tissue homogenates were prepared using a Polytron homogenizer as described (Chomczynski and Sacchi, 1987). Total RNA was isolated by the guanidinium isothiocyanate/CsCl method (Glizin, et al., 1974) or by the acid guanidinium isothiocyanate-phenol-chloroform extraction method (Chomczynski and Sacchi, 1987) using a commercial kit ("TRIZOL", Life Technologies, Inc., Gaithersburg, Md.). mRNA was isolated from the total RNA using oligo(dT)$_{25}$ "DYNABEADS" (Dynal, Inc., Lake Success, N.Y.) following manufacturer's instructions ("mRNA Isolation Using "DYNABEADS" OLIGO(dT)$_{25}$", pp 35–60 in *Biomagnetic Techniques in Molecular Biology—Technical Handbook*, Second Edition, Dynal; A. S. (Oslo, Norway) (1995). Briefly, Poly-A⁺ mRNA was selected using "MAGNETIC DYNABEADS OLIGO (dT)$_{25}$¹" (Dyndal A. S., Oslo, Norway) according to protocol 2.3.1 (Jakobsen, et al., 1990, 1994) as recommended by the manufacturer.

4. cDNA Synthesis. Cell or tissue Double-stranded (ds) cDNA was synthesized using the "SUPERSCRIPT" "CHOICE SYSTEM" kit for cDNA synthesis (GIBCO/BRL Life Technologies, Gaithersburg, Md.) according to the manufacturer's instructions, except that custom adapters (Adapter #3 and adapter #5, described below) were used in place of the EcoR1 adapters supplied with the kit. Approximately 5 $\mu$g of poly(A⁺) mRNA were used with oligo dT15 or random hexamers to synthesize ds cDNA. The cDNA was purified from the primers and the low molecular weight products (<250 bp) on "WIZARD" PCR Preps DNA Purification System columns (Promega, Madison, Wis.) according to the manufacturer's protocol, and ligated to dephosphorylated adapters #3 (SEQ ID NO:1, SEQ ID NO:2) or #5 (SEQ ID NO:3, SEQ ID NO:4) using standard methods (Sambrook, et al., 1989). Typically, cDNA pools designed for direct selection contained, adapter #3 at their ends to allow single primer PCR amplification (e.g., using primer #A3-2 (SEQ ID NO:5) or primer #AD3-CUA (SEQ ID NO:6; see below).

The adapters were made by combining oligonucleotides #4665 (SEQ ID NO:1) and #4666 (SEQ ID NO:2) (Adapter #3), or oligonucleotide's #A5-1. (SEQ ID NO:3) and #A5-2 (SEQ ID NO:4) (Adapter #5), heating the mixtures to 95° C. for 5 minutes, and allowing the mixtures to gradually cool to room temperature over about 30 minutes. This caused the oligonucleotides in the mixtures to hybridize and form double stranded adapters with 3' overhangs as illustrated below. The adapters were then dephosphorylated with calf intestine phosphatase (CIP) using a standard protocol (Ausubel, et al., 1988), and the phosphatase inactivated by incubating 70° C. for 10 min.

5'-biotinylated primer #A5-2b. (SEQ ID NO:7) was designed to synthesize biotinylated subtraction probes (e.g., ribosomal, mitochondrial, Alu-, etc.) from cDNA fragments containing Adapter #5 using PCR. Primer #A3-2 (SEQ ID NO:5) was designed to synthesize similar probes from cDNA fragments containing Adapter #3. CUA-containing primer #AD3-CUA (SEQ ID NO:6) was designed to PCR amplify cDNAs that subcloned into the pAMP10 vector. (GIBCO/BRL Life Technologies, Inc).

B. Screening of cDNA Samples with Cytokine PCR Primers

The presence of specific cytokine cDNAs in the different cDNA samples/pools was determined using PCR to provide an estimate of the degree to which such cytokine transcripts were present, i.e., to "validate" the cDNA samples/pools as sources for cytokine cDNAs. The PCR reactions were carried out using standard methods (Mullis, 1987; Mullis, et al., 1987) with the primer pairs presented in Table 2, below.

TABLE 2

| Primers | SEQ ID NO: | $T_{ann}$ | Sequence | Product Size |
|---|---|---|---|---|
| GM-CSF-2 | 8 | 60° C. | CCTTGACCATGATGGCCAGCC | 187 bp |
| GM-CSF-1 | 9 | | CCCGGCTTGGCCAGCCTCATC | |
| IL3-1 | 10 | 55° C. | CTCTGTGGTGAGAAGGCCCA | 287 bp |
| IL3-2 | 11 | | CTTCGAAGGCCAAACCTGGA | |
| IL4-3 | 12 | 55° C. | GGTTTCCTTCTCAGTTGTGTT | 210 bp |
| IL4-4 | 13 | | CTCACCTCCCAACTGCTTCCC | |
| IL5-1 | 14 | 55° C. | CACCAACTGTGCACTGAAGAAATC | 213 bp |
| IL4-2 | 15 | | CCACTCGGTGTTCATTACACC | |
| IL9-1 | 16 | 60° C. | AGCTTCTGGCCATGGTCCTTAC | 360 bp |
| IL9-6 | 17 | | TCAGCGCGTTGCCTGCCGTGGT | |
| IL13-1 | 18 | 55° C. | ATGGCGCTTTTGTTGACCAC | 1013 bp |
| IL13-5 | 19 | | CCTGCCTCGGATGAGGCTCC | |
| IRF1-7 | 20 | 55° C. | GAAGGCCAACTTTCGCTGTG | 367 bp |
| IRF1-8 | 21 | | CACTGGGATGTGCCAGTCGG | |
| TCF7-3 | 22 | 55° C. | CCGTTCCTTCCGATGACAGTGCT | 898 bp |
| TCF7-4 | 23 | | GACATCAGCCAGAAGCAAGT | |
| EGRI1-6 | 24 | 60° C. | CCACCTCCTCTCTCTCTTCCTA | 750 bp |
| EGRI1-7 | 25 | | TCCATGGCACAGATGCTGTAC | |
| CD14-5 | 26 | 65° C. | CCGCTGGTGCACGTCTCTGCGACC | 1022 bp |
| CD14-6 | 27 | | CACGCCGGAGTTCATTGAGCC | |
| CDC25-3 | 28 | 65° C. | GAGAGGAAGGAAGCTCTGGCTC | 282 bp |
| CDC25-5 | 29 | | GTCCTGAAGAATCCAGGTGACC | |

All cDNA samples and cDNA pools #1 and #2 were screened using PCR with the above primers, and the relative amount of specific amplification product determined. Prior to amplification, the samples were diluted such that the concentration of cDNA was the same in each sample (about 200 $\mu$g/ml). The results for individual cDNA samples are presented in the Table 3, below. Three pluses (+++) indicate a relatively high level of expression, (++) an intermediate level, (+) a relatively low level, (±) a very low but consistent level, (∓) a very low and inconsistent level, and (−) no detectable expression.

treatment and lysis, YACs were separated in 1% LMT agarose pulsed field gels in 0.5×TBE at 14° C. as described below.

All the separations were carried out, in "CHEF-DR III" pulsed-field electrophoresis system (Bio-Rad) with follow-

TABLE 3

| cDNA | IL13 | IL14 | IRF1 | IL5 | IL3 | GM-CSF | TCF7 | IL9 | EGR1 | CD14 | CDC25 |
|---|---|---|---|---|---|---|---|---|---|---|---|
| T-cells | ++ | +++ | +++ | +++ | +++ | ++++ | +++ | +++ | − | ± | − |
| A-10 | +++ | ++++ | +++ | ++++ | +++ | ++++ | ± | +++ | ++ | ± | ∓ |
| Jurkat | + | + | +++ | − | +++ | +++ | +++ | − | − | ± | + |
| CEM | ++ | ++ | +++ | ∓ | +++ | +++ | +++ | − | ++ | ± | ++ |
| HUT78 | ++ | ++ | +++ | + | +++ | ++++ | +++ | − | +++ | ± | ++ |
| JM | + | − | +++ | ∓ | +++ | ++++ | +++ | − | − | ± | +++ |
| Molt4 | + | ++ | +++ | − | − | − | +++ | − | − | ± | ++ |
| HNG-1 | ++ | − | ++= | − | − | ++++ | +++ | − | +++ | ± | ++ |
| Daudi | − | − | + | − | − | − | ± | − | − | ∓ | + |
| 816 | − | +++ | +++ | ± | − | − | ± | +++ | − | − | ∓ |
| Mono | − | − | +++ | − | +++ | − | − | − | − | +++ | − |

Daudi B-lineage cell lymphoma (Daudi); Monocytes stimulated with LPS for 6 hrs (Mono); Adult T cells stimulated with Con A and PMA for 6 hrs (T-cells); EBV-transformed B-cell line 816 (816); HNG-1 T-cell lineage lymphoma (HNG-1); Molt-4 T-cell lineage lymphoma (Molt4); JM T-cell lineage lymphoma (JM); HUT-78 T-cell lineage lymphoma (HUT78); CEM T-cell lineage lymphoma stimulated with ionomycin and PMA for 6 hrs (CEM); Jurkat T-cell lineage lymphoma (Jurkat); and Clone A-10 of T-cell origin, producing high levels of IL4 and IL5 and stimulated with Con A for 6 hrs (A-10)

The data in Table 3, above, suggest that a cDNA pool formed of cDNA samples in the first 6 rows of the table, along with the monocyte cDNA, may be particularly effective as a source of cytokine cDNAs. Accordingly, cDNA pool #3 was formed by combining equal fractions of these seven cDNA samples. cDNA pool #4 was formed by combining equal fractions of all eleven cDNA samples listed in Table 3, above, along with cDNA from adult bone marrow.

Eight additional cDNA pools, termed cDNA pools #5–12, were constructed by combining, at a 1:1 vol/vol ratio, cDNA pool #3 with cDNA samples of similar concentrations isolated from human tissues, including total embryo (6, 8, 12 weeks of gestation; pools #5, 6 and 7, respectively), fetal liver (pool #8), fetal brain (pool #9), adult bone marrow (pool #10), adult thymus (pool #11), and adult spleen (pool #12).

EXAMPLE 2

Preparation of Genomic DNA for Direct Selection

A. Mapping of Genomic Clones used for Direct Selection

Yeast artificial chromosome (YAC) clones containing sequences from the cytokine gene cluster area of chromosome 5 (5q23-31) were isolated and physically mapped to provide a template for the direct selection of the cDNA samples and pools described in Example 1. YAC clone A94G6 (~425 kb) was obtained from the YAC Washington University library (St. Louis, Mo.) (Burke, et al., 1987; Morgan, et al., 1992). Clones 259E7 (~490 kb) and 854G6 (~1.3 mb) were isolated from CEPH regular and mega YAC libraries (Bellanne-Chantelot, et al., 1992).

To construct a physical map of the YAC clones, the clones were digested with NotI and run on a clamped homogeneous electrical fields (CHEF) mapper system ("CHEF-DR III" Variable Angle Pulsed Field Electrophoresis System, Bio-Rad Laboratories, Hercules, Calif.). The yeast clones were grown in liquid AHC medium (Bellanne-Chantelot, et al., 1992) for, 48 hrs at 30° C. Cells were harvested, washed and embedded in 0.5% low melting temperature agarose (LMT) as described (Chumakov, et al., 1992). After the zymolase ing parameters: 1) small YACs (400–500 kb)—power 06 V/cm; run time 24 hrs 4 min; initial switch time 21.41; final.switch time 39.48; 2) mega YACs (1–1.5 mb)—power 0.6V/cm; run time$^1$ 22 hrs 30 min; switch time$^1$ 60.00; run time$^2$ 12 hrs 30 min; switch time$^2$ 90.00.

The CHEF gels were blotted and hybridized by standard Southern hybridization (Sambrook, et al., 1989) to probes for IL13, IL4, IL5, IRF1, IL3, GM-CSF, all of which are located in 5q23-31. The hybridization conditions, unless specified, were: 5×SSPE, 0.1%SDS, 5×Denhardt's, $^{32}$P-labelled probe, 65° C. overnight. The blots were washed first with 1×SSC+0.1 SDS at room temperature, and then with 0.1×SSC+0.1 SDS at 65° C. several times, 15 min each.

The results from the hybridizations were used to construct a physical map of the 1.3 megabase (Mb) region encompassed by YACs A94G6, 259E7 and 854G6, which is presented in FIG. 1. This map was confirmed and further refined by physically mapping a panel of chromosome 5-specific cosmids, as described in Example 5, below.

B. Direct Selection Protocol

DNA from the genomic clones was isolated as described in part C, below. The isolated DNA was labeled with biotin either by PCR using biotinylated primers SEQ ID NO:34 and SEQ ID NO:35, or by conventional labelling technique. For PCR labelling 5'-biotinylated primers were used that had been synthesized at Genosys Biotechnologies, Inc. (Woodlands, Tex.). For conventional labelling either photoactivatable biotin (PAB) or Biotin-21-dUTP nick translation labelling kits from Clontech (Palo Alto, Calif.) were used.

Biotinylated genomic DNA was hybridized in solution with complex representative cDNA pools #4–12. In selection with YACs A94G6 and, 259E7, cDNA pool #4 was used. In selection with the mega YAC 854G6, a mixture of equal amounts of cDNA pools #4–12 was used. Hybridization was done at 65° C. in 20 µl of 5×SSPE, 1×Denhardt, 0.1% SDS to Cot=500. cDNAs that was close to saturation was efficiently-captured under these conditions. Specifically-bound cDNAs were captured with Dynal streptavidin beads and washed with 400 µl of 2×SSC. 0.5% SDS twice at RT, 10 min each and 4 times with 400 µl of 0.2×SSC+0.1% SDS at 65° C., 5 min each time.

Biotinylated genomic DNA-cDNA hybrids and free YAC DNA fragments were captured with streptavidin coated magnetic beads (Dynal A. S., Oslo, Norway) for 30 min at RT with occasional tapping. Two hundred μg of the beads (40 μl, 5 μg/μl) were added per each 5 pMoles of biotinylated PCR product (up to 4 kb in length). About 4 μg of the biotinylated PCR products within the range of 1–4 kb could be captured by this amount of beads. Dynabeads were washed twice with buffer containing 1M NaCl in preblocking buffer (TE pH 7.5+200 μg/ml Herring sperm DNA+ 0.1% BSA) and resuspended to 5 μg/μl in the same buffer without DNA or RNA. The suspension was incubated at room temperature (RT) for 30 min, and the beads were captured and isolated with the aid of a magnet. The isolated beads were then washed with 400 μl of 2μSSC, 0.5% SDS twice at RT, 10 min each and 4 times with 400 μl of 0.2×SSC+0.1% SDS at 65° C., 5 min each time.

After washing, specifically bound cDNAs were eluted from the hybrids of the biotinylated DNA-cDNA either by incubating the beads with 40 μl of 2.5 mM EDTA at 80° C. or with 100 mM NaOH at RT. The latter was followed by neutralization with 20 μl of 0.2 M HCl and 10 μl of 1M Tris-HCl pH 8.0.

Eluted cDNAs were PCR amplified by single primer amplification (SISPA) using either primer #AD3-2 (SEQ ID NO:5) or #AD3-CUA. (SEQ ID NO:6); Primer #AD3-CUA was used when PCR products were to be cloned in pAMP10. This cloning system substantially reduced the background of "0"-insert and chimeric clones.

A second round of direct selection was usually performed following completion of the first round. The first round typically resulted in a several hundred to a thousand fold enrichment. The second round of selection enabled enrichment up to about a hundred-thousand-fold (Morgan, et al., 1992).

To determine whether a second round of selection was necessary, cDNA aliquots were SISPA-propagated the #AD3-2 primer (SEQ ID NO:5), cleaned up by "WIZARD" PCR column chromatography, quantitated, and run a on 1% agarose gel (about 1 μg/lane) both before and after selection. The gels were visualized, blotted, and hybridized with the probes known to reside within given genomic DNA. Alternatively, PCR was used to assess the enrichment by direct selection (Morgan, et al., 1992). If the degree of enrichment was less than about ten thousand-fold, a second round was performed.

C. Preparation of YAC DNA for Direct Selection

YAC clones A94G6, 259E7 and 854G6 were grown overnight in AHC medium at 30° C. Agarose blocks were prepared according to the protocol of LePaslier (Chumakov, et al., 1992). Briefly, yeast cells harboring the YACs were harvested, washed, counted and embedded in 0.5% Sea-Plaque GTG agarose (FMC, Rockland, Me.) as described in CHEF-DR$^R$III instruction manual and application guide. YAC DNAs or their restriction fragments were separated in 1% LMT agarose, (FMC) pulsed field gels in 0.5×TBE at 14° C. according to the Bib-Rad protocols. For smaller YACs (400–500 kb), the following parameters were applied: power 0.6 V/cm; run time 24 hrs 4 min; initial switch time 21.41; final switch time 39.48. For mega YACs (1–1.5 mb), the following parameters were applied: power 0.6V/cm; run time$^1$ 22 hrs 30 min; switch>time$^1$ 60.00; run time$^2$ 12 hrs 30 min; switch time$^2$ 90.00.

YAC DNA-containing bands (containing 250 ng DNA) were excised, placed into tubes with 2 vol of 1×Sau3AI buffer (New England Biolabs (NEB), Beverly, Mass.), and treated with 12 U of Sau3AI (NEB) at 37° C. for 5 hrs.

The agarose containing the digested YAC DNA was then melted in 1 volume of TE at 68° C., and the DNA isolated using the "WIZARD". PCR Preps DNA Purification System (Promega, Madison, Wis.) at 37° C. following the manufacturer's instructions. DNA was eluted with TE (pH 8.0).

Due to steric hindrance of the incorporated biotin, one of the following adapters was ligated to the eluted YAC DNA to allow more efficient SISPA amplification and PCR controlled labelling, with biotin: (i) Sau3A1 semiadapter #1, made of primers having sequences. SEQ ID NO:52 and SEQ ID NO:53, (ii) Sau3A1 semiadapter #2, made of primers having sequences SEQ ID NO:30 and SEQ ID NO:31, or (iii) Sau3A1 adapter #S-1/S-2, made of primers having sequences SEQ ID NO:32 and SEQ ID NO:33. Sau3A1 semiadapter #2 provided better yields and specificity in ligations and subsequent PCRs.

Ligation of the linkers was typically carried overnight at +14° C. in 20 μl of the reaction mix, containing 100 ng of Sau3AI-digested YAC DNA, 100 pmoles of adapter, and 6 U of T4 DNA Ligase (New England Biolabs).

EXAMPLE 3

Direct Selection with the Genomic DNA Fragments Encompassing Cytokine Gene Cluster in 5q23-31

YAC clone DNA was PCR-amplified for 30 cycles using biotinylated primers SEQ ID NO:34 and SEQ ID NO:35. The amplified YAC DNA was, then preblocked with Cot1 DNA (GIBCO/BRL Life Technologies, Inc.) and used for direct selection with cDNA samples as follows.

One hundred ng of the amplified biotinylated YAC DNA were mixed with 5 μg Cot1 DNA and 5 μg yeast host strain AB1380 in 8 μl of water and denatured for 15 min under mineral oil at 98° C. in a heating block. The mixture was then supplemented with 2 μl of 25×SSPE+5×Denhardt+ 0.5% SDS to a final concentration of 5×SSPE, 1×Denhardt solution and 0.1% sodium dodecyl sulfate (SDS) in 10 μl, and hybridized for 2.0 hrs at 60° C. to Cot=20. In parallel, 10 μg of cDNAs were denatured in 8 μl of water for 15 min under mineral oil and treated as described above.

Ten μg of cDNAs from selected samples were denatured in 8 μl of water for 15 min under mineral oil as described above and supplemented to a final concentration of 5×SSPE, 1×Denhardt and 0.1% SDS. Direct selection was initiated by mixing 10 μl of the amplified cDNAs with 10 μl of the amplified and preblocked biotinylated YAC DNA (100 ng), and hybridization was conducted to a Cot=500 (about 40 hrs) at 65° C. under mineral oil. A Cot value of 1 is equivalent to 83 μg/ml of DNA×1 hour at 60° C. in 5×SSPE.

A. Isolation of cDNA/DNA Hybrids with Magnetic Beads

The hybridization mixture was then incubated with streptavidin coated magnetic beads (Dynal, Inc., Lake Success, N.Y.) in a buffer containing. 1M NaCl in TE pH 7.5+0.1% BSA for 30 min at room temperature with occasional tapping to immobilize the biotinylated genomic DNA fragments, some of which contained hybridized cDNA species. Two hundred μg of the beads (40 μl, 5 μg/μl), effective to capture about 4 μg of the biotinylated PCR products (1–4 kb), were added per each 5 pmoles of biotinylated YAC DNA PCR product.

Following the incubation, the "DYNABEADS" were collected using a magnetic stand (Dynal, Inc.). The beads were then washed with 400 μl of 2×SSC, 0.5% SDS twice at RT, 10 min each, and 4 times with 400 μl of 0.2×SSC+ 0.1% SDS at 65° C., 5 min each. Specifically bound biotinylated DNA-cDNAs were incubated either with 40 μl of 2.5 mM EDTA at 80° C., or with 100 mM NaOH at RT with occasional tapping of the tube, eluted and neutralized with 20 µl of 0.2 M HCl and 10 µl of M Tris-HCl pH 8.0.

Specifically bound biotinylated DNA-cDNAs were eluted either with 40 µl of 2.5 mM EDTA at 80° C. or with 100 mM NaOH at RT with occasional tapping of the tube. In cases where NaOH was used, the eluted beads were neutralized with 20 µl of 0.2 M HCl and 10 µl of 1M Tris-HCl pH 8.0.

B. Subcloning of Selected cDNAs

The eluted material (2 µl) was PCR-amplified for approximately 30 cycles in 100 µl tubes using approximately 50 pmoles each of primers SEQ ID NO:5 and SEQ ID NO:6, typically for 30 cycles using 2 µl of the eluate per 100 µl reaction. Primer SEQ ID NO:6 was used only when the PCR products were to be subcloned into the pAM10 vector. The PCR cycle parameters were as follows: 30 sec at 94° C., 30 sec at $T_{ann}$–5° C., and 2 min at 72° C. After the last cycle, the reactions were incubated for 7 min at 72° C., and then kept at 4° C. until further processing.

The PCR-amplified material was typically used for a second round of direct selection as described above, selected, products were PCR amplified with primer SEQ ID NO:6, and ~1–5 µg of the selected cDNAs were subcloned into the pAMP10 vector ("CLONEAMP" directional PCR cloning system, GIBCO/BRL Life Technologies, Inc), which is adapted for uracil DNA glycosilase (UDG) cloning. This approach does not require restriction endonuclease digestion, end-polishing, purification or ligation. With this system, PCR products should contain specified 12-base 5' sequence that contains dUMP residues instead of dTMP.

Treatment with UDG renders dUMP residues abasic, disrupting base-pairing which results in 3'-protruding termini. pAMP10 plasmid contains a modified multiple cloning site and 3' ends that are complementary to the 3' protruding termini of the UDG-treated PCR amplification products obtained with the primer SEQ ID NO:6. Linear vector and UDG both go to the selected amplified cDNAs, without ligase, and are complete in less than 30 min, producing recombinant molecules ready for transformation.

1 µl of 20 µl UDG-reaction mixture was typically used to electroporate 50 µl of electrocompetent JS5 *E. coli* cells (Bio-Rad) according to manufacture's protocol in a "GENE PULSER" apparatus (Bio-Rad), in 0.1 cm electrode gap cuvettes. After 1 hr incubation of electroporated cells in 1 ml of Luria Broth (LB), 100 µl of the culture was plated onto LB plates containing 100 µg/ml Ampicillin.

The quality of a direct selection was monitored by Southern blot hybridization using a probe known to reside on the YAC, when similar quantities of the PCR amplified cDNA were loaded on the gel before and after the selection. Usually up to 100,000-fold enrichment was observed in two rounds of selection. Before and after the selection cDNA aliquots were SISPA-propagated with the primer SEQ. ID NO:5, cleaned up by Wizard PCR column chromatography, quantitated, and run in 1% agarose-gel (about 1 µg/lane). The gels were visualized, blotted, and hybridized with the probes known to reside within given genomic DNA. Alternatively, quantitative PCR was used to assess the enrichment by direct selection. The enrichment ratios of direct selection were also monitored by plating cDNA aliquots before and after the selection, and counting the ratio of several marker clones to overall colonies. For example, if there was one IL3 positive clone in $10^6$ colonies beforehand one in 10 after the selection, the enrichment was considered to be around $10^5$ fold on this step. The selection process was controlled such that there was at least a 10 thousand-fold enrichment for at least one marker. Alternatively, negative selection was controlled for the markers known not to be on the YACs. In this case, the data were examined for a decrease in the ratio of this gene during selection.

EXAMPLE 4

Hybridization and Sequence Analysis of the Arrayed Region-Specific cDNAs

A. Analysis and Subcloning of the PCR Products

Individual colonies of PCR pAMP10 clones generated as described above were used to inoculate wells containing LB broth in 96-well plates. The cultures were incubated overnight at 37° C. and an aliquot from each well was transferred to an Immobilon-N membrane (Millipore, Bedford, Mass.), forming a grid corresponding to the locations of the samples in the plate.

The DNA was immobilized on the membranes using UV-crosslinking, and the membranes were then screened with $^{32}$P-labelled YAC, Cot1, mitochondrial, ribosomal and single copy probes known to reside on a starting genomic clone, in order to eliminate nonspecific or already known cDNAs from further analysis, as follows.

Membranes with the arrayed cDNAs were hybridized with different $^{32}$P-labelled probes: highly repetitive, high molecular weight human COT1 DNA (Life Technologies, Inc.), human mitochondrial and ribosomal probes, starting YAC probe, single copy marker genes, known to reside within the genomic region in question. Because starting total cellular RNA contained certain amount of heteronuclear, ribosomal and mitochondrial species, final cDNA pools still contained these species, and it was much easier to prescreen the arrayed libraries for them rather than to introduce additional steps into the selection protocol.

About 55% of the clones in arrayed selected cDNA libraries were eliminated in such a prescreening procedure. Single copy known genes from the genomic region in question were monitored as well, and were used to evaluate the quality of the selected material and the depth of the libraries. These statistics also aided in determining how many novel cDNAs might be expected. For instance, 18% of the clones in the A94G6 YAC selection library belonged to IRF1, IL13, IL3 and IL5.

Negative clones were subject to sequencing. Sequencing data confirmed that there were at least 7 novel gene candidates, one of which was assembled into a full-length clone of a human homolog of *S. cerevisiae* RAD50. After computer analysis of the sequencing data, PCR primers were designed for prospective novel gene cDNAs and were used, both to evaluate the tissue-specificity of expression of the gene candidates and for physical mapping of cDNAs to human chromosome 5 and the starting YAC, as described below.

B. Sequence Analysis

Unique and presumably novel cDNA clones were sequenced and screened for similarity of their nucleotide and amino acid sequences using Fasta, BlastN, BlastX, tBlastN programs in known protein and nucleic acid databases. For efficient and quick identification of non-overlapping cDNAs, redundant cDNAs were eliminated by subsequent hybridization of the arrayed libraries with already identified individual cDNAs as probes and unique sequences were further analyzed as described below.

After two rounds of selection, ~66% of all clones mapped back to the starting genomic region, i.e., YAC or any other genomic DNA used to select these particular cDNAs. Each cDNA species comprised >1% of the selected material. The complexity of the selected cDNAs (i.e., the number of distinct species of DNAs) was dependent on the gene density in the region with respect to which the cDNAs were selected, and on the complexity of the starting cDNA sources.

EXAMPLE 5

Mapping Selected Clones to Chromosome 5: Physical Mapping of cDNAs to Cosmids A human chromosome 5-specific cosmid library was obtained from L. Deaven (Los Alamos National laboratories, N.Mex.) as arrayed individual clones in 96 well-plates that represented 8×genome equivalents subcloned in the sCos1 vector (Longmire, et al., 1993). The *E. coli* DH5 clones contained about 81% human inserts, 8% rodent inserts and 3% nonrecombinants. About 25,000 individual cosmid clones were microgridded onto "HYBOND-N" nylon membrane (Amersham Life Sciences, UK) using a "BIOMEK 1" (Beckman, Palo Alto, Calif.) robotic station. The filters with spotted clones were grown overnight on 96-well plate lids (Cat. #76-205-05, ICN Flow, Costa Mesa, Calif.) filled with 1.5% LB SeaKem GTG agarose (FMC Bioproducts, Rockland, Me.) supplemented with 20 $\mu$g/ml kanamycin (Sigma).

After treating the filters on Whatman 3 mm paper saturated with 2×SSC/0.5% SDS for 2 min, the filters were microwaved for 2.5 min at ~750 W until dry. Then they were submerged in a buffer containing 50 mM Tris-HCl pH 8.0, 50 mM EDTA, 100 mM NaCl, 1% Na-lauryl-sarcosine, and 250 mg/ml Proteinase K (Boehringer). After incubation for 20 min at 37° C. the filters were UV-crosslinked on. Fotodyne crosslinker for 35 sec. After washing, the microgrids were hybridized with different $^{32}$P-oligolabelled YAC, cDNA or terminal cosmid walking probes as described below. Many cDNAs selected with the above specified YACs were mapped to the clones on the microgrids. Other libraries may be similarly used for mapping purposes, including YAC, BAC, and P1 genomic libraries.

EXAMPLE 6

Determining-Tissue Specific Expression

Tissue specificity of expression was performed using Northern blot analyses and PCR detection.

A. Northern Blot Analyses

Total RNA was isolated by the guanidinium isothiocyanate/CsCl method (Glisin, et al., 1974) or by the acid guanidinium isothiocyanate-phenol-chloroform extraction method using a commercial kit (Tri-reagent, Molecular Research Center, Cincinnati, Ohio), and was resolved on formaldehyde gels using standard methods (Sambrook, et al., 1989). The gels were blotted onto "HYBOND N" membranes. (Amersham Life Sciences, UK), fixed by UV-crosslinking, and the membranes probed with radiolabeled probes corresponding to the clones Conditions: Hybridization buffer, containing 5x-SSPE, 2×Denhardt, 100 $\mu$g/ml sonicated salmon sperm DNA, 0.5% SDS; Hybridization temperature=65° C.

All probes consisted of DNA labeled by the random hexamer priming method using a commercial kit (Pharmacia, Piscataway, N.J.), with the exception of the IL4 probe, for which a single-stranded RNA probe was employed.

B. RT-PCR Analysis

About 1 $\mu$g of total RNA from different sources was reverse transcribed (RT) by random priming with "SUPERSCRIPT II" (GIBCO/BRL Life Technologies, Gaithersburg, Md.) in 20 $\mu$l of reaction mix as specified by the manufacturer. After heat inactivation, 1 $\mu$l of the RT-reaction was used in a 30 $\mu$l PCR of 30 cycles of conventional PCR with the primers and $T_{ann}$ specified below. Each PCR reaction contained 20 mM Tris-HCl pH 8.9 (at 25° C.), 16.7 mM $(NH_4)_2SO_4$, 1.5 mM $MgCl_2$, 200 $\mu$M dNTPs, 1 $\mu$M primers, and 0.8 U AmpliTaq (Cetus).

PCR-based detection of tissue-specific expression was performed using the following PCR-amplifiable primary cDNA pools: Total Embryo (6, 8, 12 weeks of gestation), Fetal Liver, Fetal Brain, Fetal Muscle, Placenta, Adult Heart, Adult Muscle, Adult Liver, Adult Brain, Adult Pancreas, Adult Kidney, Adult Aorta, Adult Spleen, Adult Testis, Adult Bone Marrow, JY B-cell line, Resting T-cells and Activated T-cells.

These cDNAs were either used directly as targets or PCR amplified for 30 cycles using primer SEQ ID NO:5. Amplified cDNAs were purified on a "WIZARD-PCR" column (Promega, Madison, Wis.), quantitated, and used in PCR reactions with different specifically-designed primers. The primer used were as indicated in Table 1.

Each PCR reaction contained 50 ng of one cDNA sample or pool (amplified or unamplified) as the target. After cycles of PCR the products were separated on agarose gels and the intensity of the signals recorded and represented in Table 1, above.

EXAMPLE 7

Identification of Gene Function by Homology and Motif Identification

A. Identification of the Human Homolog of the Yeast Gene RAD50

Three cDNA clones A106, G157, G170, selected with the YACs A94G6 and 854G6 as described in Example 3, were mapped to chromosome 5-specific cosmid 256E1 about 10 kb upstream of the IL13 gene. Clone A106, when used as a probe, detected a predominant and ubiquitous mRNA species of 1.9 kb on a Northern blot of various mRNA species, including T-cells, B-cells, testis, small intestine, and brain. The primers A106-1 and A106-2 (SEQ ID NO:36 and SEQ ID NO:37, respectively) were used in RT PCR to evaluate the tissue distribution and to extend the cDNA to its full length.

RT PCR analysis confirmed that this message was expressed in activated adult T-cells, total embryo, fetal muscle, fetal liver, placenta, adult heart, and adult bone marrow. The extension of the A106 cDNA clone confirmed that it is a human homolog of the yeast gene RAD50. Northern blot hybridizations with the C-terminal coding portion of the gene used as a probe revealed two mRNA species: a strong signal of about 5.8 kb and a weaker signal at 6.5 kb.

A near full-length cDNA, termed G10 (also referred to as "rad50.seq"; SEQ ID NO:54), was obtained using marathon RACE (rapid amplification of cDNA ends; Chenchik, et al., 1995) techniques with activated T-cell and testis cDNA marathon pools. A marathon cDNA pool in contrast to a regular cDNA pool has a special adapter at the ends of cDNAs. Such cDNAs can not be SISPA amplified, because the adapter design suppresses PCR with a single adapter-specific primer (Siebert, et al., 1995). Exponential PCR will be observed only if a gene-specific primer is employed along with the adapter-specific primer. Such cDNA pools allow both 5'- and 3'-RACE amplifications, and finally isolation of intact genes via combination PCR (Chenchik, et al., 1995).

cDNA clone G10 is about 5,800 bp long and encodes a protein of 1312, aa with two highly-conserved domains with respect yeast RAD50: an N-terminal ATP-binding domain and a conserved C-terminal domain. A non-coding 3'-flanking portion of the gene when used as a probe, detected mRNA species of 1.9 and 0.85 kb in multiple tissues. This may indicate either unusual alternative splicing of the RAD50 gene or an overlap with another gene. RT-PCR and Northern blot analyses have confirmed that G10 is expressed in activated T-cells, B-cells, placenta and multiple fetal tissues, including fetal liver.

Clones G18 and H230, have a 31 bp stretch at their 31-end homologous to RAD50. RT-PCR analysis on different cDNA pools and genomic DNA with primers G18-1/2 (SEQ ID NO:50 and SEQ ID NO:51), respectively suggested alternative splicing of the RAD50. The RAD50 had been first mapped by PCR using the primers A106 1/2 (SEQ ID NO:36 and SEQ ID NO:37) and then by YAC Southern blot hybridization. Several chromosome 5-specific cosmids had been isolated that span the RAD50 gene. The genomic equivalent of G10 was found to be between about 80 and 150 kb in length. RAD50 appears to be a large gene with at least six exons. The C-terminal 2b fragment (~6 kb) of RAD50 was sequenced, enabling the positioning of four C-terminal exons.

C. Isolation and Mapping of cdc3 Human Homolog

Seventeen cDNAs encoding a novel cell division control gene were identified using direct selection with YAC clone 854G6. These cDNAs represent bin 23 in Table 1. The consensus sequence of these cDNAs was extended using the marathon RACE technique and is presented herein as SEQ ID NO:97.

EXAMPLE 8

Assays to Evaluate Immunomodulatory Activity of Compounds or Polypeptides

A. Peripheral Blood Lymphocyte (PBL) Proliferation Assay

Human peripheral blood lymphocytes are prepared using an established method (e.g., Boyum, 1968). Human blood buffy coat samples are resuspended in a calcium and magnesium-free Hank's balanced salt solution (HBSS, Gibco/BRL Life Technologies) at ~24° C. Approximately 25 ml of the cell suspension is then layered onto ~15 ml of Ficoll-Paque (Pharmacia LKB Biotechnology, Inc.), and is centrifuged at ~400×g for ~30 minutes at 15° C.

Following centrifugation, the PBL suspension at the interface is transferred to new centrifuge tubes, resuspended in a total volume of ~45 ml HBSS and centrifuged at ~350×g for ~10 minutes at 15° C. The supernatants are discarded and the PBL's are resuspended in 10 ml HBSS, combined, and centrifuged at ~260×g for ~10 minutes at 15° C. The cell pellets are suspended in 10 ml of X-Vivo tissue culture medium (Bio Whittaker, Walkersville, Md.) and counted using a hemocytometer. Tissue culture medium is then added to achieve a final cell concentration of ~1×10$^6$ cells/ml.

Proliferation assays are carried out in 96 well sterile tissue culture plates (e.g., Costar 3790 or Costar 3595). A volume of 100 µl PBL suspension is added to each well and the plates are incubated under an atmosphere of 93% air/7% $CO_2$ in a tissue culture incubator at 37° C. Compounds or polypeptides whose immunomodulatory activity is to be evaluated are then added to the wells. Different wells may have different compounds or polypeptides, or they may have different concentrations of the same compound or polypeptide. The plates may also have several wells with the same immunomodulatory compound or polypeptide at the same concentration, with other types of immunomodulatory compounds (e.g., small molecules) present in some wells.

After a selected period of time (e.g., 48 hours), ~50 µl of X-Vivo tissue culture medium containing ~8 µCi/ml [$^3$H] Thymidine (Amersham, ~50 Ci/mmol) are added to each tissue culture well. Following four hours additional incubation at 37° C., the cells are removed from the tissue culture wells and applied to filter paper using, e.g., a cell harvester. The filter paper is dried and cut into small (e.g., 1 cm) discs, which are placed in a scintillation vial containing ~2 ml of scintillation fluid (Biosafe, Research Products International Corp.). Samples are then counted in a scintillation counter (e.g., the Beckman LS 6000SC).

B. Spleen Cell Proliferation Assay

C3H mice are sacrificed by $CO_2$ inhalation and the spleens removed and cleaned of any fat or connective tissue. A nick is made in the tip of each spleen, and cells are collected by gentle aspiration through the tissue with Hank's balanced salt solution (HBSS) using a syringe and 18-gauge needle. The resultant spleen cell solution is filtered through Nytex sterile nylon mesh (Tetco), centrifuged at 200×g for 10 minutes, resuspended in HBSS, and centrifuged as above.

The pelleted cells are resuspended in a small amount of HBSS, counted using a hemocytometer and then resuspended in RPMI 1640 medium (Gibco/BRL Life Technologies, catalog 430-1800GL), containing 2-mercaptoethanol (50 µM), glutamine (2 mM), penicillin (100 U/ml), streptomycin (100 mg/ml and 5% (v/v) fetal calf serum (Hyclone or Sigma) to a concentration of 2.5×10$^6$ cells/ml.

A 100 µl volume of spleen cell solution is added to each well of a 96-well plate. Compounds or polypeptides having immunomodulatory activity or medium alone are added in a volume of 50 µl. The cultures are incubated for 2 days (37° C., 5% $CO_2$), and tritiated thymidine incorporation is assayed as described above.

EXAMPLE 9

PCR-Based Detection of Activated T-Cells

Polymerase chain reaction amplifications were performed as described above using cDNA derived from the following sources. Unless otherwise indicated, the tissues samples were obtained from adult individuals. (1) cDNA pool #3, (2) activated T-cells (3) bone marrow, (4) fetal liver, (5) testis, (6) thymus, (7) peripheral leukocytes, (8) lymph node, (9) brain, (10) fetal thymus, (11) fetal brain, (12) spleen, (13) placenta, (14) muscle, (15) kidney and (16) heart.

Each 100 µl PCR reaction contained 50 ng of cDNA target, 50 pmols each of primers A116-1 (SEQ ID NO:150) and A116-2 (SEQ ID NO:149), 200 µM dNTPs, 2 mM MgCl2, 1×magnesium-free amplification buffer (Perkin-Elmer) and 2.5 U Taq DNA Polymerase. The primers were designed based on the sequence shown in FIG. 1 (SEQ ID NO:151), which is a portion of the A116 sequence (SEQ ID NO:85). The locations of the primers relative to the sequence are underlined.

The samples were cycled using a Perkin Elmer DNA Thermal Cycler 480 (Norwalk, Conn.) thermal cycler for 30 times through the following steps: 30 s at 94° C., 30 s at 55° C. and 2 minutes at 72° C. The amplification products were then separated on agarose gels, stained with ethidium bromide, and visualized to determine their size. An exemplary image of such a gel is shown in FIG. 2. The lanes in the gel correspond to cDNA from tissues (1) through (12), above. Amplification products of the appropriate size were consistently detected only in samples containing activated. T-cells (1 and 2). Such amplification products were not detected in any of the other samples (3–16), with the exception of fetal liver (4), where a much fainter signal was occasionally observed.

These results indicate that PCR-based amplification of a DNA fragment having the sequence SEQ ID NO:151 may be used as a sensitive diagnostic for the presence of activated T-cells in a sample of cells. An exemplary primer pair suitable for use with such an amplification reaction consists of primers having sequences SEQ ID NO:149 and SEQ ID NO:150.

While the invention has been described with reference to specific methods and embodiments, it is appreciated that various modifications and changes may be made without departing from the invention.

What is claimed is:

1. An isolated human Septin-2 polynucleotide containing a sequence represented by SEQ ID NO:97.

2. The isolated human Septin-2 polynucleotide of claim 1, containing an open reading frame that encodes a Septin-2 polypeptide.

3. The isolated human Septin-2 polynucleotide of claim 2 encoding a polypeptide having the sequence identified by SEQ ID NO:143.

* * * * *

SEQUENCE LISTING (1) GENERAL INFORMATION:

(iii) NUMBER OF SEQUENCES: 151

(2) INFORMATION FOR SEQ ID NO:1:

(i) SEQUENCE CHARACTERISTICS:
      (A) LENGTH: 22 base pairs
      (B) TYPE: nucleic acid
      (C) STRANDEDNESS: single
      (D) TOPOLOGY: linear (ii) MOLECULE TYPE: DNA (iii) HYPOTHETICAL: NO (iv) ANTI-SENSE: NO (vi) ORIGINAL SOURCE:
      (C) INDIVIDUAL ISOLATE: oligonucleotide #4665 for adapter #3

(xi) SEQUENCE DESCRIPTION: SEQ ID NO:1:

GAGGATCCAG AATTCTCGAG TT                    22

(2) INFORMATION FOR SEQ ID NO:2:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: DNA (iii) HYPOTHETICAL: NO (iv) ANTI-SENSE: NO (vi) ORIGINAL SOURCE:
      (C) INDIVIDUAL ISOLATE: oligonucleotide #4666 for adapter #3

(xi) SEQUENCE DESCRIPTION: SEQ ID NO:2:

CTCCTAGGTC TTAAGAGCTC                        20

(2) INFORMATION FOR SEQ ID NO:3:

(i) SEQUENCE CHARACTERISTICS:
      (A) LENGTH: 23 base pairs
      (B) TYPE: nucleic acid
      (C) STRANDEDNESS: single
      (D) TOPOLOGY: linear (ii) MOLECULE TYPE: DNA (iii) HYPOTHETICAL: NO (iv) ANTI-SENSE: NO (vi) ORIGINAL SOURCE:
             (C) INDIVIDUAL ISOLATE: oligonucleotide #A5-1 for adapter #5

(xi) SEQUENCE DESCRIPTION: SEQ ID NO:3:

TGGATCCTCT AGAGAGTGTG GTT                                              23

(2) INFORMATION FOR SEQ ID NO:4:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (ii) MOLECULE TYPE: DNA (iii) HYPOTHETICAL: NO (iv) ANTI-SENSE: NO (vi) ORIGINAL SOURCE:
             (C) INDIVIDUAL ISOLATE: oligonucleotide #A5-2 for adapter #5

(xi) SEQUENCE DESCRIPTION: SEQ ID NO:4:

ACCTAGGAGA TCTCTCACAC C                                                21

(2) INFORMATION FOR SEQ ID NO:5:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (ii) MOLECULE TYPE: DNA (iii) HYPOTHETICAL: NO (iv) ANTI-SENSE: NO (vi) ORIGINAL SOURCE:
             (C) INDIVIDUAL ISOLATE: oligo #AD3-2 for PCR amp of cDNAs (xi) SEQUENCE DESCRIPTION: SEQ ID NO:5:

ACTCGAGAAT TCTGGATCCT C                                                21

(2) INFORMATION FOR SEQ ID NO:6:

(i) SEQUENCE CHARACTERISTICS:
             (A) LENGTH: 33 base pairs
             (B) TYPE: nucleic acid
             (C) STRANDEDNESS: single
             (D) TOPOLOGY: linear (ii) MOLECULE TYPE: DNA (iii) HYPOTHETICAL: NO (iv) ANTI-SENSE: NO (vi) ORIGINAL SOURCE:
             (C) INDIVIDUAL ISOLATE: oligo #AD3-CUA for PCR amp of cDNAs (xi) SEQUENCE DESCRIPTION: SEQ ID NO:6:

CUACUACUAC UAACTCGAGA ATTCTGGATC CTC                                   33

(2) INFORMATION FOR SEQ ID NO:7:

```
    (i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: oligo #A5-2b for PCR amp of cDNAs (xi) SEQUENCE DESCRIPTION: SEQ ID NO:7:

CCACACTCTC TAGAGGATCC A                                              21

(2) INFORMATION FOR SEQ ID NO:8:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: Primer GM-CSF-2

(xi) SEQUENCE DESCRIPTION: SEQ ID NO:8:

CCTTGACCAT GATGGCCAGC C                                              21

(2) INFORMATION FOR SEQ ID NO:9:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: Primer GM-CSF-1

(xi) SEQUENCE DESCRIPTION: SEQ ID NO:9:

CCCGGCTTGG CCAGCCTCAT C                                              21

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
```

(C) INDIVIDUAL ISOLATE: Primer IL3-1

(xi) SEQUENCE DESCRIPTION: SEQ ID NO:10:

CTCTGTGGTG AGAAGGCCCA                                                    20

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: Primer IL3-2

(xi) SEQUENCE DESCRIPTION: SEQ ID NO:11:

CTTCGAAGGC CAAACCTGGA                                                    20

(2) INFORMATION FOR SEQ ID NO:12:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: Primer IL4-3

(xi) SEQUENCE DESCRIPTION: SEQ ID NO:12:

GGTTTCCTTC TCAGTTGTGT TCT                                                23

(2) INFORMATION FOR SEQ ID NO:13:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: Primer IL4-4

(xi) SEQUENCE DESCRIPTION: SEQ ID NO:13:

CTCACCTCCC AACTGCTTCC C                                                  21

(2) INFORMATION FOR SEQ ID NO:14:

(i) SEQUENCE CHARACTERISTICS:
        (A) LENGTH: 24 base pairs
        (B) TYPE: nucleic acid
        (C) STRANDEDNESS: single (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: Primer IL5-1

(xi) SEQUENCE DESCRIPTION: SEQ ID NO:14:

CACCAACTGT GCACTGAAGA AATC                                          24

(2) INFORMATION FOR SEQ ID NO:15:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: Primer IL4-2

(xi) SEQUENCE DESCRIPTION: SEQ ID NO:15:

CCACTCGGTG TTCATTACAC C                                             21

(2) INFORMATION FOR SEQ ID NO:16:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: Primer IL9-1

(xi) SEQUENCE DESCRIPTION: SEQ ID NO:16:

AGCTTCTGGC CATGGTCCTT AC                                            22

(2) INFORMATION FOR SEQ ID NO:17:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: Primer IL9-6

(xi) SEQUENCE DESCRIPTION: SEQ ID NO:17:

```
TCAGCGCGTT GCCTGCCGTG GT                                               22

(2) INFORMATION FOR SEQ ID NO:18:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: DNA (iii) HYPOTHETICAL: NO (iv) ANTI-SENSE: NO (vi) ORIGINAL SOURCE:
         (C) INDIVIDUAL ISOLATE: Primer IL13-1

(xi) SEQUENCE DESCRIPTION: SEQ ID NO:18:

ATGGCGCTTT TGTTGACCAC                                                  20

(2) INFORMATION FOR SEQ ID NO:19:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: DNA (iii) HYPOTHETICAL: NO (iv) ANTI-SENSE: NO (vi) ORIGINAL SOURCE:
         (C) INDIVIDUAL ISOLATE: Primer IL13-5

(xi) SEQUENCE DESCRIPTION: SEQ ID NO:19:

CCTGCCTCGG ATGAGGCTCC                                                  20

(2) INFORMATION FOR SEQ ID NO:20:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: DNA (iii) HYPOTHETICAL: NO (iv) ANTI-SENSE: NO (vi) ORIGINAL SOURCE:
         (C) INDIVIDUAL ISOLATE: Primer IRF1-7

(xi) SEQUENCE DESCRIPTION: SEQ ID NO:20:

GAAGGCCAAC TTTCGCTGTG                                                  20

(2) INFORMATION FOR SEQ ID NO:21:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: DNA
```

(iii) HYPOTHETICAL: NO (iv) ANTI-SENSE: NO (vi) ORIGINAL SOURCE:
            (C) INDIVIDUAL ISOLATE: Primer IRF1-8

(xi) SEQUENCE DESCRIPTION: SEQ ID NO:21:

CACTGGGATG TGCCAGTCGG                                                   20

(2) INFORMATION FOR SEQ ID NO:22:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (vi) ORIGINAL SOURCE:
            (C) INDIVIDUAL ISOLATE: Primer TCF7-3

(xi) SEQUENCE DESCRIPTION: SEQ ID NO:22:

CCGTTCCTTC CGATGACAGT GCT                                               23

(2) INFORMATION FOR SEQ ID NO:23:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (vi) ORIGINAL SOURCE:
            (C) INDIVIDUAL ISOLATE: Primer TCF7-4

(xi) SEQUENCE DESCRIPTION: SEQ ID NO:23:

GACATCAGCC AGAAGCAAGT                                                   20

(2) INFORMATION FOR SEQ ID NO:24:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (vi) ORIGINAL SOURCE:
            (C) INDIVIDUAL ISOLATE: Primer EGRI1-6

(xi) SEQUENCE DESCRIPTION: SEQ ID NO:24:

CCACCTCCTC TCTCTCTTCC TA                                                22

(2) INFORMATION FOR SEQ ID NO:25:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (vi) ORIGINAL SOURCE:
            (C) INDIVIDUAL ISOLATE: Primer EGRI1-7

(xi) SEQUENCE DESCRIPTION: SEQ ID NO:25:

TCCATGGCAC AGATGCTGTA C                                                      21

(2) INFORMATION FOR SEQ ID NO:26:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (vi) ORIGINAL SOURCE:
            (C) INDIVIDUAL ISOLATE: Primer CD14-5

(xi) SEQUENCE DESCRIPTION: SEQ ID NO:26:

CCGCTGGTGC ACGTCTCTGC GACC                                                   24

(2) INFORMATION FOR SEQ ID NO:27:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (vi) ORIGINAL SOURCE:
            (C) INDIVIDUAL ISOLATE: Primer CD14-6

(xi) SEQUENCE DESCRIPTION: SEQ ID NO:27:

CACGCCGGAG TTCATTGAGC C                                                      21

(2) INFORMATION FOR SEQ ID NO:28:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (vi) ORIGINAL SOURCE:
             (C) INDIVIDUAL ISOLATE: Primer CDC25-3

(xi) SEQUENCE DESCRIPTION: SEQ ID NO:28:

GAGAGGAAGG AAGCTCTGGC TC                                                22

(2) INFORMATION FOR SEQ ID NO:29:

(i) SEQUENCE CHARACTERISTICS:
             (A) LENGTH: 22 base pairs
             (B) TYPE: nucleic acid
             (C) STRANDEDNESS: single
             (D) TOPOLOGY: linear (ii) MOLECULE TYPE: DNA (iii) HYPOTHETICAL: NO (iv) ANTI-SENSE: NO (vi) ORIGINAL SOURCE:
             (C) INDIVIDUAL ISOLATE: Primer CDC25-5

(xi) SEQUENCE DESCRIPTION: SEQ ID NO:29:

GTCCTGAAGA ATCCAGGTGA CC                                                22

(2) INFORMATION FOR SEQ ID NO:30:

(i) SEQUENCE CHARACTERISTICS:
             (A) LENGTH: 25 base pairs
             (B) TYPE: nucleic acid
             (C) STRANDEDNESS: single
             (D) TOPOLOGY: linear (ii) MOLECULE TYPE: DNA (iii) HYPOTHETICAL: NO (iv) ANTI-SENSE: NO (vi) ORIGINAL SOURCE:
             (C) INDIVIDUAL ISOLATE: Primer Sau3AI-2 for semiadapter #2

(xi) SEQUENCE DESCRIPTION: SEQ ID NO:30:

TCGCGGCCGA ATTCTAGAGC TCGCT                                             25

(2) INFORMATION FOR SEQ ID NO:31:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (ii) MOLECULE TYPE: DNA (iii) HYPOTHETICAL: NO (iv) ANTI-SENSE: NO (vi) ORIGINAL SOURCE:
             (C) INDIVIDUAL ISOLATE: Primer Sau3AI-3

(xi) SEQUENCE DESCRIPTION: SEQ ID NO:31:

CGCCGGCTTA AGATCTCGAG C                                                 21

(2) INFORMATION FOR SEQ ID NO:32:

(i) SEQUENCE CHARACTERISTICS:
             (A) LENGTH: 28 base pairs
             (B) TYPE: nucleic acid

```
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: Primer Sau3AI S-1

(xi) SEQUENCE DESCRIPTION: SEQ ID NO:32:

GATCTCGAGG ATCCTCAGAG AGTAGTAG                                      28

(2) INFORMATION FOR SEQ ID NO:33:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: Primer Sau3AI S-2 for adapter #S-1/2

(xi) SEQUENCE DESCRIPTION: SEQ ID NO:33:

AGCTCCTAGG AGTCTCTCAT CATC                                          24

(2) INFORMATION FOR SEQ ID NO:34:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: 5'Biotin-YAC primer #1: PCR amp of YACs (xi) SEQUENCE DESCRIPTION: SEQ ID NO:34:

AGCGAGCTCT AGAATTCGGC CGC                                           23

(2) INFORMATION FOR SEQ ID NO:35:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: 5'Biotin-YAC primer #2: PCR amp of YACs (xi) SEQUENCE DESCRIPTION: SEQ ID NO:35:
```

CTACTACTCT CTGAGGATCC TCGAGA                                      26

(2) INFORMATION FOR SEQ ID NO:36:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: Primer A106-1 for RAD50

(xi) SEQUENCE DESCRIPTION: SEQ ID NO:36:

GTCATCCAGA CTCAGAGCTC                                             20

(2) INFORMATION FOR SEQ ID NO:37:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: Primer A106-2 for RAD50

(xi) SEQUENCE DESCRIPTION: SEQ ID NO:37:

CTGTCTAGGC AAACATGCTC                                             20

(2) INFORMATION FOR SEQ ID NO:38:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: Primer G10-C for RAD50

(xi) SEQUENCE DESCRIPTION: SEQ ID NO:38:

GAGAGGAATT CTTTTAATGA ACATTGAATC CCAGGGAG                          38

(2) INFORMATION FOR SEQ ID NO:39:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
             (C) INDIVIDUAL ISOLATE: Primer G10-N for RAD50

(xi) SEQUENCE DESCRIPTION: SEQ ID NO:39:

GAGAGGATCC TTTGTGGACT CCAGGTCCCT GGTGAGATT                                          39

(2) INFORMATION FOR SEQ ID NO:40:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (ii) MOLECULE TYPE: DNA (iii) HYPOTHETICAL: NO (iv) ANTI-SENSE: NO (vi) ORIGINAL SOURCE:
             (C) INDIVIDUAL ISOLATE: Primer G34-2

(xi) SEQUENCE DESCRIPTION: SEQ ID NO:40:

CCACACTGAT GAACACACTC T                                                              21

(2) INFORMATION FOR SEQ ID NO:41:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (ii) MOLECULE TYPE: DNA (iii) HYPOTHETICAL: NO (iv) ANTI-SENSE: NO (vi) ORIGINAL SOURCE:
             (C) INDIVIDUAL ISOLATE: Primer G34-3

(xi) SEQUENCE DESCRIPTION: SEQ ID NO:41:

AGCTCGCTCT TGGAGATGGT G                                                              21

(2) INFORMATION FOR SEQ ID NO:42:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (ii) MOLECULE TYPE: DNA (iii) HYPOTHETICAL: NO (iv) ANTI-SENSE: NO (vi) ORIGINAL SOURCE:
             (C) INDIVIDUAL ISOLATE: Primer G34-4

(xi) SEQUENCE DESCRIPTION: SEQ ID NO:42:

TGGCTTCCTC AGTCTCGAAG G                                                              21

```
(2) INFORMATION FOR SEQ ID NO:43:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: Primer G34-5

(xi) SEQUENCE DESCRIPTION: SEQ ID NO:43:

CACCATCTCC AAGAGCGAGC T                                              21

(2) INFORMATION FOR SEQ ID NO:44:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: Primer G34-6

(xi) SEQUENCE DESCRIPTION: SEQ ID NO:44:

CACCATGAGG CATGCGTGCG CCTG                                           24

(2) INFORMATION FOR SEQ ID NO:45:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: Primer G34-7

(xi) SEQUENCE DESCRIPTION: SEQ ID NO:45:

CAGGCGCACG CATGCCTCAT GGTG                                           24

(2) INFORMATION FOR SEQ ID NO:46:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO
```

(vi) ORIGINAL SOURCE:
            (C) INDIVIDUAL ISOLATE: Primer G34-8

(xi) SEQUENCE DESCRIPTION: SEQ ID NO:46:

GTAGATCTGG ACCCCGTTGC TGAC                                              24

(2) INFORMATION FOR SEQ ID NO:47:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: Primer G34-9

(xi) SEQUENCE DESCRIPTION: SEQ ID NO:47:

GTCAGCAACG GGGTCCAGAT CTAC                                              24

(2) INFORMATION FOR SEQ ID NO:48:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: Primer G34-10

(xi) SEQUENCE DESCRIPTION: SEQ ID NO:48:

ACCAGTTCCC CACGGATGAT GAGGCTG                                           27

(2) INFORMATION FOR SEQ ID NO:49:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: Primer G34-11

(xi) SEQUENCE DESCRIPTION: SEQ ID NO:49:

CCTCCGCGAG CAGACCCACA GCCGGCA                                           27

(2) INFORMATION FOR SEQ ID NO:50:

(i) SEQUENCE CHARACTERISTICS:
        (A) LENGTH: 23 base pairs (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: Primer G18-1

(xi) SEQUENCE DESCRIPTION: SEQ ID NO:50:

ATCAGACCAG GGACAGACTT GCC                                            23

(2) INFORMATION FOR SEQ ID NO:51:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: Primer G18-2

(xi) SEQUENCE DESCRIPTION: SEQ ID NO:51:

CATCTTCTTC ATGCCCTAAC TG                                             22

(2) INFORMATION FOR SEQ ID NO:52:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: oligonucleotide #4578

(xi) SEQUENCE DESCRIPTION: SEQ ID NO:52:

TAGGAGATCT CTTAAGAGCT                                                20

(2) INFORMATION FOR SEQ ID NO:53:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: oligonucleotide #4579

(xi) SEQUENCE DESCRIPTION: SEQ ID NO:53:

| | |
|---|---|
| TCTCGAGAAT TCTCTAGAGG ATCC | 24 |

(2) INFORMATION FOR SEQ ID NO:54:

(i) SEQUENCE CHARACTERISTICS:
        (A) LENGTH: 5893 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: Rad50.seq (ix) FEATURE:
        (A) NAME/KEY: CDS
        (B) LOCATION: 389..4324

(xi) SEQUENCE DESCRIPTION: SEQ ID NO:54:

| | |
|---|---|
| CCAGGAGAGC GGCGTGGACG CGTGCGGGCC TAGAGGCCCA CGTGATCCGC AGGGCGGCCG | 60 |
| AGGCAGGAAG CTTGTGAGTG CGCGGTTGCG GGGTCGCATT GTGGCTACGG CTTTGCGTCC | 120 |
| CCGGCGGGCA GCCCCAGGCT GGTCCCCGCC TCCGCTCTCC CCACCGGCGG GGAAAGCAGC | 180 |
| TGGTGTGGGA GGAAAGGCTC CATCCCCCGC CCCCTCTCTC CCGCTGTTGG CTGGCAGGAT | 240 |
| CTTTTGGCAG TCCTGTGGCC TCGCTCCCCG CCCGGATCCT CCTGACCCTG AGATTCGCGG | 300 |
| GTCTCACGTC CCGTGCACGC CTTGCTTCGG CCTCAGTTAA GCCTTTGTGG ACTCCAGGTC | 360 |
| CCTGGTGAGA TTAGAAACGT TTGCAAACAT GTCCCGGATC GAAAAGATGA GCATTCTGGG | 420 |
| CGTGCGGAGT TTTGGAATAG AGGACAAAGA TAAGCAAATT ATCACTTTCT TCAGCCCCCT | 480 |
| TACAATTTTG GTTGGACCCA ATGGGGCGGG AAAGACGACC ATCATTGAAT GTCTAAAATA | 540 |
| TATTTGTACT GGAGATTTCC CTCCTGGAAC CAAAGGAAAT ACATTTGTAC ACGATCCCAA | 600 |
| GGTTGCTCAA GAAACAGATG TGAGAGCCCA GATTCGTCTG CAATTTCGTG ATGTCAATGG | 660 |
| AGAACTTATA GCTGTGCAAA GATCTATGGT GTGTACTCAG AAAAGCAAAA AGACAGAATT | 720 |
| TAAAACTCTG GAAGGAGTCA TTACTAGAAC AAAGCATGGT GAAAAGGTCA GTCTGAGCTC | 780 |
| TAAGTGTGCA GAAATTGACC GAGAAATGAT CAGTTCTCTT GGGGTTTCCA AGGCTGTGCT | 840 |
| AAATAATGTC ATTTTCTGTC ATCAAGAAGA TTCTAATTGG CCTTTAAGTG AAGGAAAGGC | 900 |
| TTTGAAGCAA AAGTTTGATG AGATTTTTTC AGCAACAAGA TACATTAAAG CCTTAGAAAC | 960 |
| ACTTCGGCAG GTACGTCAGA CACAAGGTCA GAAAGTAAAA GAATATCAAA TGGAACTAAA | 1020 |
| ATATCTGAAG CAATATAAGG AAAAAGCTTG TGAGATTCGT GATCAGATTA CAAGTAAGGA | 1080 |
| AGCCCAGTTA ACATCTTCAA AGGAAATTGT CAAATCCTAT GAGAATGAAC TTGATCCATT | 1140 |
| GAAGAATCGT CTAAAAGAAA TTGAACATAA TCTCTCTAAA ATAATGAAAC TTGACAATGA | 1200 |
| AATTAAAGCC TTGGATAGCC GAAAGAAGCA AATGGAGAAA GATAATAGTG AACTGGAAGA | 1260 |
| GAAAATGGAA AAGGTTTTTC AAGGGACTGA TGAGCAACTA AATGACTTAT ATCACAATCA | 1320 |
| CCAGAGAACA GTAAGGGAGA AGAAAAGGAA ATTGGTAGAC TGTCATCGTG AACTGGAAAA | 1380 |
| ACTAAATAAA GAATCTAGGC TTCTCAATCA GGAAAAATCA GAACTGCTTG TTGAACAGGG | 1440 |
| TCGTCTACAG CTGCAAGCAG ATCGCCATCA AGAACATATC CGAGCTAGAG ATTCATTAAT | 1500 |
| TCAGTCTTTG GCAACACAGC TAGAATTGGA TGGCTTTGAG CGTGGGCCAT TCAGTGAAAG | 1560 |

```
ACAGATTAAA AATTTTCACA AACTTGTGAG AGAGAGACAA GAAGGGGAAG CAAAAACTGC   1620

CAACCAACTG ATGAATGACT TTGCAGAAAA AGAGACTCTG AAACAAAAAC AGATAGATGA   1680

GATAAGAGAT AAGAAAACTG GACTGGGAAG AATAATTGAG TTAAAATCAG AAATCCTAAG   1740

TAAGAAGCAG AATGAGCTGA AAAATGTGAA GTATGAATTA CAGCAGTTGG AAGGATCTTC   1800

AGACAGGATT CTTGAACTGG ACCAGGAGCT CATAAAAGCT GAACGTGAGT TAAGCAAGGC   1860

TGAGAAAAAC AGCAATGTAG AAACCTTAAA AATGGAAGTA ATAAGTCTCC AAAATGAAAA   1920

AGCAGACTTA GACAGGACCC TGCGTAAACT TGACCAGGAG ATGGAGCAGT TAAACCATCA   1980

TACAACAACA CGTACCCAAA TGGAGATGCT GACCAAAGAC AAAGCTGACA AGATGAACA    2040

AATCAGAAAA ATAAAATCTA GGCACAGTGA TGAATTAACC TCACTGTTGG GATATTTTCC   2100

CAACAAAAAA CAGCTTGAAG ACTGGCTACA TAGTAAATCA AAAGAAATTA ATCAGACCAG   2160

GGACAGACTT GCCAAATTGA ACAAGGAACT AGCTTCATCT GAGCAGAATA AAAATCATAT   2220

AAATAATGAA CTAAAAAGAA GGGAAGAGCA GTTGTCCAGT TACGAAGACA AGCTGTTTGA   2280

TGTTTGTGGT AGCCAGGATT TTGAAAGTGA TTTAGCAGG CTTAAAGAGG AAATTGAAAA    2340

ATCATCAAAA CAGCGAGCCA TGCTGGCTGG AGCCACAGCA GTTTACTCCC AGTTCATTAC   2400

TCAGCTAACA GACGAAAACC AGTCATGTTG CCCCGTTTGT CAGAGAGTTT TTCAGACAGA   2460

GGCTGAGTTA CAAGAAGTCA TCAGTGATTT GCAGTCTAAA CTGCGACTTG CTCCAGATAA   2520

ACTCAAGTCA ACAGAATCAG AGCTAAAAAA AAAGGAAAAG CGGCGTGATG AAATGCTGGG   2580

ACTTGTGCCC ATGAGGCAAA GCATAATTGA TTTGAAGGAG AAGGAAATAC CAGAATTAAG   2640

AAACAAACTG CAGAATGTCA ATAGAGACAT ACAGCGCCTA AAGAACGACA TAGAAGAACA   2700

AGAAACACTC TTGGGTACAA TAATGCCTGA AGAAGAAAGT GCCAAAGTAT GCCTGACAGA   2760

TGTTACAATT ATGGAGAGGT TCCAGATGGA ACTTAAAGAT GTTGAAAGAA AAATTGCACA   2820

ACAAGCAGCT AAGCTACAAG AATAGACTT AGATCGAACT GTCCAACAAG TCAACCAGGA    2880

GAAACAAGAG AAACAGCACA AGTTAGACAC AGTTTCTAGT AAGATTGAAT TGAATCGTAA   2940

GCTTATACAG GACCAGCAGG AACAGATTCA ACATCTAAAA AGTACAACAA ATGAGCTAAA   3000

ATCTGAGAAA CTTCAGATAT CCACTAATTT GCAACGTCGT CAGCAACTGG AGGAGCAGAC   3060

TGTGGAATTA TCCACTGAAG TTCAGTCTTT GTACAGAGAG ATAAAGGATG CTAAAGAGCA   3120

GGTAAGCCCT TTGGAAACAA CATTGGAAAA GTTCCAGCAA GAAAAGAAG AATTAATCAA     3180

CAAAAAAAT ACAAGCAACA AAATAGCACA GGATAAACTG AATGATATTA AGAGAAGGT     3240

TAAAAATATT CATGGCTATA TGAAAGACAT TGAGAATTAT ATTCAAGATG GAAAGACGA    3300

CTATAAGAAG CAAAAAGAAA CTGAACTTAA TAAAGTAATA GCTCAACTAA GTGAATGCGA   3360

GAAACACAAA GAAAAGATAA ATGAAGATAT GAGACTCATG AGACAAGATA TTGATACACA   3420

GAAGATACAA GAAAGGTGGC TACAAGATAA CCTTACTTTA AGAAAAAGAA ATGAGGAACT   3480

AAAAGAAGTT GAAGAAGAAA GAAAACAACA TTTGAAGGAA ATGGGTCAAA TGCAGGTTTT   3540

GCAAATGAAA AGTGAACATC AGAAGTTGGA AGAGAACATA GACAATATAA AAAGAAATCA   3600

TAATTTGGCA TTAGGGCGAC AGAAAGGTTA TGAAGAAGAA ATTATTCATT TAAGAAAGA    3660

ACTTCGAGAA CCACAATTTC GGGATGCTGA GGAAAAGTAT AGAAAATGA TGATTGTTAT    3720

GAGGACAACA GAACTTGTGA ACAAGGATCT GGATATTTAT TATAAGACTC TTGACCAAGC   3780

AATAATGAAA TTTCACAGTA TGAAAATGGA AGAAATCAAT AAAATTATAC GTGACCTGTG   3840

GCGAAGTACC TATCGTGGAC AAGATATTGA ATACATAGAA ATACGGTCTG ATGCCGATGA   3900
```

```
AAATGTATCA GCTTCTGATA AAAGGCGGAA TTATAACTAC CGAGTGGTGA TGCTGAAGGG    3960

AGACACAGCC TTGGATATGC GAGGACGATG CAGTGCTGGA CAAAAGGTAT TAGCCTCACT    4020

CATCATTCGC CTGGCCCTGG CTGAAACGTT CTGCCTCAAC TGTGGCATCA TTGCCTTGGA    4080

TGAGCCAACA ACAAATCTTG ACCGAGAAAA CATTGAATCT CTTGCACATG CTCTGGTTGA    4140

GATAATAAAA AGTCGCTCAC AGCAGCGTAA CTTCCAGCTT CTGGTAATCA CTCATGATGA    4200

AGATTTTGTG GAGCTTTTAG GACGTTCTGA ATATGTGGAG AAATTCTACA GGATTAAAAA    4260

GAACATCGAT CAGTGCTCAG AGATTGTGAA ATGCAGTGTT AGCTCCCTGG GATTCAATGT    4320

TCATTAAAAA TATCCAAGAT TTAAATGCCA TAGAAATGTA GGTCCTCAGA AAGTGTATAA    4380

TAAGAAACTT ATTTCTCATA TCAACTTAGT CAATAAGAAA ATATATTCTT TCAAAGGAAC    4440

ATTGTGTCTA GGATTTTGGA TGTTGAGAGG TTCTAAAATC ATGAAACTTG TTTCACTGAA    4500

AATTGGACAG ATTGCCTGTT TCTGATTTGC TGCTCTTCAT CCCATTCCAG GCAGCCTCTG    4560

TCAGGCCTTC AGGGTTCAGC AGTACAGCCG AGACTCGACT CTGTGCCTCC CTCCCCAGTG    4620

CAAATGCATG CTTCTTCTCA AAGCACTGTT GAGAAGGAGA TAATTACTGC CTTGAAAATT    4680

TATGGTTTTG GTATTTTTTT AAATCATAGT TAAATGTTAC CTCTGAATTT ACTTCCTTGA    4740

CATGTGGTTT GAAAAACTGA GTATTAATAT CTGAGGATGA CCAGAAATGG TGAGATGTAT    4800

GTTTGGCTCT GCTTTTAACT TTATAAATCC AGTGACCTCT CTCTCTGGGA CTTGGTTTCC    4860

CCAACTAAAA TTTGAAGTAG TTGAATGGGG TCTCAAAGTT TGACAGGAAC CTTAAGTAAT    4920

CATCTAAGTC AGTACCCACC ACCTTCTTCT CCTACATATC CCTTCCAGAT GGTCATCCAG    4980

ACTCAGAGCT CTCTCTACAG AGAGGAAATT CTCCACTGTG CACACCCACC TTTGGAAAGC    5040

TCTGACCACT TGAGGCCTGA TCTGCCCATC GTGAAGAAGC CTGTAACACT CCTCTGCGTC    5100

TATCCTGTGT AGCATACTGG CTTCACCATC AATCCTGATT CCTCTCTAAG TGGGCATTGC    5160

CATGTGGAAG GCAAGCCAGG CTCACTCACA GAGTCAAGGC CTGCTCCCTG TAGGGTCCAA    5220

CCAGACCTGG AAGAACAGGC CTCTCCATTT GCTCTTCAGA TGCCACTTCT AAGAAAAGCC    5280

TAATCACAGT TTTTCCTGGA ATTGCCAGCT GACATCTTGA ATCCTTCCAT TCCACACAGA    5340

ATGCAACCAA GTCACACGCT TTTGAATTAT GCTTTGTAGA GTTTTGTCAT TCAGAGTCAG    5400

CCAGGACCAT ACCGGGTCTT GATTCAGTCA CATGGCATGG TTTTGTGCCA TCTGTAGCTA    5460

TAATGAGCAT GTTTGCCTAG ACAGCTTTTC TCAACTGGGT CCAGAAGAGA ATTAAGCCCT    5520

AAGGTCCTAA GGCATCTATC TGTGCTAGGT TAAATGGTTG GCCCCAAAG ATAGACAGGT     5580

CCTGATTTCT AGAACCCGTG ACTGTTACTT TATACAGCAA AGGAAACTTT GCAGATGTGA    5640

TTAAAGCTAA GGACCTTAAG ACAGAGTATC CTGGGGGTGG TGGTGGGGTG GGGGGGGGTC    5700

CTAAATGTAA TCACGAGTAA GATTAAGAGC CAATCAATTC TAGTCATATA TTAAACATCC    5760

ACAATAACCA AGATATTTTT ATCCCAAGAA TGCAAGATTT CAGAAAATGA AAAATCTGTT    5820

GATAAATCCA TCACTATAAT AAAACCGAAG GTGAAAAAAA TTCTGAAAAA AAAAAAAAA    5880

AAAAAAAAA AAA                                                      5893
```

(2) INFORMATION FOR SEQ ID NO:55:

(i) SEQUENCE CHARACTERISTICS:
        (A) LENGTH: 472 base pairs
        (B) TYPE: nucleic acid
        (C) STRANDEDNESS: double
        (D) TOPOLOGY: linear (ii) MOLECULE TYPE: cDNA to mRNA -continued (iii) HYPOTHETICAL: NO (iv) ANTI-SENSE: NO (vi) ORIGINAL SOURCE:
    (C) INDIVIDUAL ISOLATE: G18.seq (xi) SEQUENCE DESCRIPTION: SEQ ID NO:55:

```
GTGGAAGAAT GGTGAAATCA TTGATACTTT ACAACAAGTT TATGAGATCA ATGCCCCAAA    60

CAAATCAGCA GTTTACAAAT GGATAACTCA GTTTAAGAAG GGATGAGACG ATATTAAAGA   120

TGAAGCCCAC AGTGACAGAC TGTTCACATC AATTTGTGAG GAAAAAAATC ATCTTCTTCA   180

TGCCCTAACT GAAGAAGATC AATGATTAAC AGCAGAAACA ATAGCCAACA CCATAGACAC   240

CTCAATTGAT TCAGGTTACA CAATTCTGAC TGAAAAATTA AAGTTGAGTA AACGTTCTAC   300

TTGATGGATG CCCAAATCAC TGCTTCCAGA TCAGCTGCAG ACAACAGCAG AACTTCCTCA   360

ATAAGTGGGA TCAAGTTCCT AAAGCATTTC TTCAAAGAAT TGTAACAGGA GGTGATGGAA   420

TGTGGCTTTA CCAGTACAAT CTTCAATTTG GCAAGTCTGT CCCTGGTCTG AT          472
```

(2) INFORMATION FOR SEQ ID NO:56:

(i) SEQUENCE CHARACTERISTICS:
        (A) LENGTH: 1189 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: Tc1.seq (xi) SEQUENCE DESCRIPTION: SEQ ID NO:56:

```
CCTGTGAACA TTGACAATAT ATTACTTTTA GTGGTACACA GTTCTTGAGA AAATGTCTTG    60

ATTTTTACAT TGCCATTTGT GATATTTTTA GCAGTCCACC ACAATATCAT TTTTATAATA   120

AAAATAAAAT ATACTCATTG ATGATAGAGA AAATATTGTT AAAGACCTCT TGGGACAGGA   180

AAAGGCTCAG TCATAAAATC AGATGCTTAT TCATTTTCAG CTGTGTCATT TTGACTCATT   240

ACTTTCAAGA ATAACTATAA TATTGCTAGA CAGTTCATTA CACTGAGAAG AACTTTCCTT   300

GAACTTCACA TGGAGATTGA GTAAAGCTCT TCTATTTGTT TTTTGAAGTA CTCTCTCAGC   360

TCAGGTCTCT TAGCTTTTAG TGTTGGTGTC AGCAAGCCAT TTTGAACTGA GAACATGTCA   420

GAATGGATGT GAATGGCTTT AACCTGCTCA AAAGAATGGA GTCCACTTTC TTTTCCTAAC   480

CTCACCATAT CTTCCAAAAT GGCTTTCTTC AGATCCTTAT TTGTGCAGAG ATCTGCATAT   540

GTTCCTTCAA TTCCTCTCTT CTGGGCCCAG GAGGGCATAA CTTCAGGGTC AGGCACAACA   600

ATGCCTACCA AAAGGCCTTT TAAGCTGTCC CCATGGACAT AGATTTGCGC CACAGGTTGG   660

CTCCGGATGT AGATGTTCTC AATCTTCTCG GGTGCAACAT ATTCTCCCTG AGCAAGTTTA   720

AATATATGCT TTTTCCGATC AATAATTTTA AGAGTTCCTG CCGGCAGCCA TTTTCCGATG   780

TCTCCAGTGT GAAGCCAGCC ATCGCTGTCC AGGGCCTCCT TCGTCCTGTC TGGATCTTTC   840

AAGTAGCCTC TGAACACATT TGGTCCTCTC ACACATATCT CTCCCTCTCC TTTGCAGGCC   900

CAGTAGTTCA GTTCCTCAAC ATCAACGAGC TTGATATGAT TGCAGGGAAG TGGCGCCCCT   960

ACGTGCCCTG AGGTCCAGTC GCCAGGAGTG GTGAAGGTAC ATCCAGCTGT GCACTCAGTT  1020
```

| | |
|---|---|
| TGGCCATAAC CTTCATAAAC CTGGCACCCT AGAGCTGCCC GGAGAAATCC CAGAACTGTT | 1080 |
| GGTGATGCTG GGGCTGCTCC AGTAACAATC ATCCGCACAA GTCACCTAGC TCAGGCAGTC | 1140 |
| GCAGTATCCT CAGGATCTCC TGTGTCTGCA TCTTCTCAGA AGTGAGAGG | 1189 |

(2) INFORMATION FOR SEQ ID NO:57:

(i) SEQUENCE CHARACTERISTICS:
        (A) LENGTH: 987 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: Tc2.seq (xi) SEQUENCE DESCRIPTION: SEQ ID NO:57:

| | |
|---|---|
| CCTCTCACTT CTGAGAAGAT GCAGACACAG GAGATCCTGA GGATACTGCG ACTGCCTGAG | 60 |
| CTAGGTGGCT TGGGACAGTT TTTCCGCAGC CTCTCGGCCA CCACCCTCGT GAGTATGGGT | 120 |
| GCCCTGGCTG CCATCCTTGC CTACTGGTTC ACTCACCGGC CAAAGGCCTT GCAGCCGCCA | 180 |
| TGCAACCTCC TGATGCAGTC AGAAGAAGTA GAGGACAGTG GCGGGGCACG GCGATCTGTG | 240 |
| ATTGGGTCTG GCCCTCAGCT ACTTACCCAC TACTATGATG ATGCCCGGAT CATGTACCTG | 300 |
| GTGTCCCGCC GTGGGCTTAG CATCTCAGGG AATGGGCCCT GTCTTGGTTT CAGGAAGCCT | 360 |
| AAGCAGCCTT ACCAGTGGCT GTCCTACCAG GAGGTGGCCG ACAGGGCTGA ATTTCTGGGG | 420 |
| TCCGGACTTC TCCAGCACAA TTGTAAAGCA TGCACTGTCA GTTTATTGGT GTTTTTGCAC | 480 |
| AAAATCGGCC AGAGTGGATC ATTGTGGAGC TGGCCTGCTA CACATATTCC ATTCTTTTGA | 540 |
| GCAGGTTAAG GCCATTTACA TCCATTCTGA CATGTTCTCA GTTCAAAATG GCTTGCTGAC | 600 |
| ACCAACACTA AAAGCTAAGA GACCTGAGCT GAGAGAGTAC TTCAAAAAAC AAATAGAAGA | 660 |
| GCTTTACTCA ATCTCCATGT GAAGTTCAAG GAAAGTTCTT CTCAGTGTAA TAAACTGTCT | 720 |
| AGCAATATTA TAGTTATTCT TGAAAGTAAT GAGTCAAAAT GACACAACTG AAAATGAATA | 780 |
| AGCATCTGAT TTTATGACTG AGCCTTTTCC TGTCCCATGA GGTCTTTAAC AATATTTTCT | 840 |
| CTATCATCAA TGAGTATATT TTATTTTTAT TATAAAAATG ATATTGTGGT GGACTGCTAA | 900 |
| AAATATCACA AGTGGCAATG TAAAAATCAA GACATTTTCT CAAGAACTGT GTACCACTAA | 960 |
| AAGTAATATA TTGTCAATGT TCACAGG | 987 |

(2) INFORMATION FOR SEQ ID NO:58:

(i) SEQUENCE CHARACTERISTICS:
        (A) LENGTH: 691 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: Tc3.seq (xi) SEQUENCE DESCRIPTION: SEQ ID NO:58:

-continued

```
CCTGTGAACA TTGACAATAT ATTACTTTTA GTGGTACACA GTTCTTGAGA AAATGTCTTG      60

ATTTTTACAT TGCCATTTGT GATATTTTTA GCAGTCCACC ACAATATCAT TTTTATAATA     120

AAAATAAAAT ATACTCATTG ATGATAGAGA AAATATTGGA GGATCCAGAA TTCTCGAGTT     180

GCCTCCTTTT TTGGCAGACT TCATCTTCTC ATCTCCCAAA CCCCCTGAGC CCGTAGGGTT     240

TTCATAGTGG ACAAAGAACT TGTGGTCTTT TAAAACTGGG ACTGATACTT TTTTGAGAGA     300

GTATCGTGTC GAAAGTGTGA TGTTCTACCA CTTTACCAAT AACTAATTTT AAATACACAT     360

TGTCCTCTCG ATTTTTGGAC CAAACAGACG CTCACAGTGG AGGCTTATCA AGGGTTGCAT     420

TGGGGAAGAA GCCTCTCCCT CTCTGTCAGC ACCAGCTGGT AAAGGTGACT GTACAGATGT     480

GCATTTTCCT TTTGGTATAA ATGGTCCACA GCACTAACTG GTAAGGCTTA TTGTGCAGTA     540

TATTGTCAGT ATTCTTCTGG TTCAGCATGC CTTATAGTTC ANATATAACC TGTATTAANT     600

GTATAGATTG TGCAGTAAAA GCTGTTACCA AGTTGTCAGA ACATAAGAGC GAAAACAAGG     660

TCATATGTAA TATATTGTCA ATGTTCACAG G                                   691

(2) INFORMATION FOR SEQ ID NO:59:

(i) SEQUENCE CHARACTERISTICS:
        (A) LENGTH: 2511 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: TcA.seq (xi) SEQUENCE DESCRIPTION: SEQ ID NO:59:

CCTCTCACTT CTGGAGAAGA TGCAGACACA GGAGATCCTG AGGATACTGC GACTGCCTGA      60

GCTAGGTGAC TTGGGACAGT TTTTCCGCAG CCTCTCGGCC ACCACCCTCG TGAGTATGGG     120

TGCCCTGGCT GCCATCCTTG CCTACTGGTT CACTCACCGG CCAAAGGCCT TGCAGCCGCC     180

ATGCAACCTC CTGATGCAGT CAGAAGAAGT AGAGGACAGT GGCGGGGCAC GGCGATCTGT     240

GATTGGGTCT GGCCCTCAGC TACTTACCCA CTACTATGAT GATGCCCGGA CCATGTACCA     300

GGTGTTCCGC CGTGGGCTTA GCATCTCAGG GAATGGGCCC TGTCTTGGTT TCAGGAAGCC     360

TAAGCAGCCT TACCAGTGGC TGTCCTACCA GGAGGTGGCC GACAGGGCTG AATTTCTGGG     420

GTCCGGACTT CTCCAGCACA ATTGTAAAGC ATGCACTGAT CAGTTTATTG GTGTTTTTGC     480

ACAAAATCGG CCAGAGTGGA TCATTGTGGA GCTGGCCTGC TACACATATT CCATGGTGGT     540

GGTCCCGCTC TATGACACCC TGGGCCCTGG GGCTATCCGC TACATCATCA ATACAGGGCT     600

CAGCTGCCAA GAAGGAGCCT CTGCAACAGC CTCCACACAG GGTACAGCCC TCTGAAGTTC     660

ATGACAGCTT GGCACAGATG CAGGGGGTGC GGACATCAGC ACCGTGATTG TGGACAAACC     720

TCAGAAGGCT GTGCTTCTGC TAGAGCATGT GGAGAGGAAG GAGACTCCAG GCCTCAAGCT     780

GATCATCCTC ATGGACCCAT TCGAAGAAGC CCTGAAAGAG AGAGGGCAGA AGTGCGGGGT     840

GGTCATTAAG TCCATGCAGG CCGTGGAGGA CTGTGGCCAA GAGAATCACC AGGCTCCTGT     900

GCCCCCGCAG CCTGATGACC TCTCCATTGT GTGTTTCACA AGCGGCACGA CAGGGAACCC     960

AAAAGGTGCG ATGCTCACCC ATGGGAACGT GGTGGCTGAT TTCTCAGGCT TTCTGAAAGT    1020
```

```
GACAGAGAGT CAGTGGGCTC CCACTTGTGC GGATGTGCAC ATTTCCTAGT TGCCTTTAGC    1080

ACACATGTTT GAGCGAATGG TGCAGTCTGT CGTCTATTGC CACGGAGGGC GTGTTGGCTT    1140

CTTCCAGGGA GATATCCGCC TTCTCTCAGA TGACATGAAG GCTCTATGCC CCACCATCTT    1200

CCCTGTGGTC CCACGACTGC TGAACCGGAT GTACGACAAG ATCTTCAGCC AGGCAAACAC    1260

ACCATTAAAG CGCTGGCTCC TGGAGTTTGC AGCAAAACGT AAGCAAGCCG AGGTCCGGAG    1320

TGGAATCATC AGGAATGATA GTATCTGGGA TGAACTCTTC TTTAATAAGA TTCAGGCCAG    1380

TCTTGGTGGG TGTGTGCGGA TGATTGTTAC TGGAGCAGCC CCAGCATCAC CAACAGTTCT    1440

GGGATTTCTC CGGGCAGCTC TAGGGTGCCA GGTTTATGAA GGTTATGGCC AAACTGAGTG    1500

CACAGCTGGA TGTACCTTCA CCACTCCTGG CGACTGGACC TCAGGGCACG TAGGGGCGCC    1560

ACTTCCCTGC AATCATATCA AGCTCGTTGA TGTTGAGGAA CTGAACTACT GGGCCTGCAA    1620

AGGAGAGGGA GAGATATGTG TGAGAGGACC AAATGTGTTC AAAGGCTACT TGAAAGATCC    1680

AGACAGGACG AAGGAGGCCC TGGACAGCGA TGGCTGGCTT CACACTGGAG ACATCGGAAA    1740

ATGGCTGCCG GCAGGAACTC TTAAAATTAT TGATCGGAAA AAGCATATAT TTAAACTTGC    1800

TCAGGGAGAA TATGTTGCAC CCGAGAAGAT TGAGAACATC TACATCCGGA GCCAACCTGT    1860

GGCGCAAATC TATGTCCATG GGACAGCTT AAAGGCCTTT TTGGTAGGCA TTGTTGTGCC    1920

TGACCCTGAA GTTATGCCCT CCTGGGCCCA GAAGAGAGGA ATTGAAGGAA CATATGCAGA    1980

TCTCTGCACA AATAAGGATC TGAAGAAAGC CATTTTGGAA GATATGGTGA GGTTAGGAAA    2040

AGAAAGTGGA CTCCATTCTT TTGAGCAGGT TAAAGCCATT CACATCCATT CTGACATGTT    2100

CTCAGTTCAA AATGGCTTGC TGACACCAAC ACTAAAAGCT AAGAGACCTG AGCTGAGAGA    2160

GTACTTCAAA AACAAATAG AAGAGCTTTA CTCAATCTCC ATGTGAAGTT CAAGGAAAGT    2220

TCTTCTCAGT GTAATGAACT GTCTAGCAAT ATTATAGTTA TCTTGAAAG TAATGAGTCA    2280

AAATGACACA GCTGAAAATG AATAAGCATC TGATTTTATG ACTGAGCCTT TTCCTGTCCC    2340

AAGAGGTCTT TAACAATATT TTCTCTATCA TCAATGAGTA TATTTTATTT TTATTATAAA    2400

AATGATATTG TGGTGGACTG CTAAAAATAT CACAAATGGC AATGTAAAAA TCAAGACATT    2460

TTCTCAAGAA CTGTGTACCA CTAAAAGTAA TATATTGTCA ATGTTCACAG G             2511
```

(2) INFORMATION FOR SEQ ID NO:60:

(i) SEQUENCE CHARACTERISTICS:
        (A) LENGTH: 2416 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: TcB.seq (xi) SEQUENCE DESCRIPTION: SEQ ID NO:60:

```
CCTCTCACTT CTGGAGAAGA TGCAGACACA GGAGATCCTG AGGATACTGC GACAGCCTGA      60

GCTAGGTGAC TTGGGACAGT TTTTCCGCAG CCTCTCGGCC ACCACCCTCG TGAGTATGGG     120

TGCCCTGGCT GCCATCCTTG CCTACTGGTT CACTCACCGG CCAAAGGCCT TGCAGCCGCC     180

ATGCAACCTC CTGATGCAGT CAGAAGAGGT AGAGGACAGT GGCGGGGCAC GGCGATCTGT     240

GATTGGGTCT GGCCCTCAGC TACTTACCCA CTACTATGAT GATGCCCGGA CCATGTACCA     300
```

-continued

```
GGTGTTCCGC CGTGGGCTTA GCATCTCAGG GAATGGGCCC TGTCTTGGTT TCAGGAAGCC    360

TAAGCAGCCT TACCAGTGGC TGTCCTACCA GGAGGTGGCC GACAGGGCTG AATTTCTGGG    420

GTCCGGACTT CTCCAGCACA ATTGTAAAGC ATGCACTGAT CAGTTTATTG GTGTTTTTGC    480

ACAAAATCGG CCAGAGTGGA TCATTGTGGA GCTGGCCTGC TACACATATT CCATGGTGGT    540

GGTCCCGCTC TATGACACCC TGGGCCCTGG GGCTATCCGC TACATCATCA ATACAGCGGA    600

CATCAGCACC GTGATTGTGG ACAAACCTCA GAAGGCTGTG CTTCTGCTAG AGCATGTGGA    660

GAGGAAGGAG ACTCCAGGCC TCAAGCTGAT CATCCTCATG GACCCATTCG AAGAAGCCCT    720

GAAAGAGAGA GGGCAGAAGT GCGGGGTGGT CATTAAGTCC ATGCAGGCCG TGGAGGACTG    780

TGGCCAAGAG AATCACCAGG CTCCTGTGCC CCCGCAGCCT GATGACCTCT CCATTGTGTG    840

TTTCACAAGC GGCACGACAG GAACCCAAA AGGTGCGATG CTCACCCATG GAACGTGGT    900

GGCTGATTTC TCAGGCTTTC TGAAAGTGAC AGAGAGTCAG TGGGCTCCCA CTTGTGCGGA    960

TGTGCACACT TCCTATTTGC CTTTAGCACA CATGTTTGAG CGAATGGTGC AGTCTGTCGT   1020

CTATTGCCAC GGAGGGCGTG TTGGCTTCTT CCAGGGAGAT ATCCGCCTTC TCTCAGATGA   1080

CATGAAGGCT CTATGCCCCA CCATCTTCCC TGTGGTCCCA CGACTGCTGA ACCGGATGTA   1140

CGACAAGATC TTCAGCCAGG CAAACACACC ATTAAAGCGC TGGCTCCTGG AGTTTGCAGC   1200

AAAGCGTAAG CAAGCCGAGG TCCGGAGTGG AATCATCAGG AATGATAGTA TCTGGGATGA   1260

ACTCTTCTTT AATAAGATTC AGGCCAGTCT TGGTGGGTGT GTGCGGATGA TTGTTACTGG   1320

AGCAGCCCCA GCATCACCAA CGGTTCTGGG ATTTCTCCGG GCAGCTCTAG GGTGCCAGGT   1380

TTATGAAGGT TATGGCCAAA CTGAGTGCAC AGCTGGATGT ACCTTCACCA CTCCTGGCGA   1440

CTGGACCTCA GGGCACGTAG GGGCGCCACT TCCCTGCAAT CATATCAAGC TCGTTGATGT   1500

TGAGGAACTG AACTACTGGG CCTGCAAAGG AGAGGGAGA ATATGTGAGA GGACCAAATG   1560

TGTTCAAAGG CTACTTGAAA GATCCAGACA GGACGAAGGA GGCCCTGTAC GGCGATGGCT   1620

GGCTTCACAC TGGAGACATC GGTAAATGGC TGCCGGCAGG AACTCTTAAA ATTATTGATC   1680

GGAAAAAGCA TATATTTAAA CTTGCTCAGG GAGTATATGT TGCACCCGAG AAGATTGAGA   1740

ACATCTACAT CCGGAGCCAA CCTGTGGCGC AAATCTATGT CCATGGGGAC AGCTTAAAGG   1800

CCTTTTTGGT AGGCATTGTT GTGCCTGACC CTGAAGTTAT GCCCTCCTGG GCCCAGAAGA   1860

GAGGAATTGA AGGAACATAT GCAGATCTCT GCACAAATAA GGATCTGAAG AAAGCCATTT   1920

TGGAAGATAT GGTGAGGTTA GGAAAAGAAA GTGGACTCCA TTCTTTTGAG CAGGTTAAAG   1980

CCATTCACAT CCATTCTGAC ATGTTCTCAG TTCAAAATGG CTTGCTGACA CCAACACTAA   2040

AAGCTAAGAG ACCTGAGCTG AGAGAGTACT TCAAAAAACA AATAGAAGAG CTTTACTCAA   2100

TCTCCATGTG AAGTTCAAGG AAAGTTCTTC TCAGTGTAAT GAACTGTCTA GCAATATTAT   2160

AGTTATTCTT GAAAGTAATG AGTCAAAATG ACACAGCTGA AAATGAATAA GCATCTGATT   2220

TTATGACTGA GCCTTTTCCT GTCCCAAGAG GTCTTTAACA ATATTTTCTC TATCATCAAT   2280

GAGTATATTT TATTTTTATT ATAAAAATGA TATTGTGGTG GACTGCTAAA AATATCACAA   2340

ATGGCAATGT AAAAATCAAG ACATTTTCTC AAGAACTGTG TACCACTAAA AGTAATATAT   2400

TGTCAATGTT CACAGG                                                  2416
```

(2) INFORMATION FOR SEQ ID NO:61:

(i) SEQUENCE CHARACTERISTICS:
        (A) LENGTH: 2416 base pairs
        (B) TYPE: nucleic acid (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
         (C) INDIVIDUAL ISOLATE: TS.seq (xi) SEQUENCE DESCRIPTION: SEQ ID NO:61:

```
CCTGTGAACA TTGACAATAT ATTACTTTTA GTGGTACGCA GTTCTTGAGA AAATGTCTTG      60
ATTTTTACAT TGCCATTTGT GATATTTTTA GCAGTCCACC ACAATATCAT TTTTATAATA     120
AAATAAAATA TACTCATTGA TGATAGAGAA AATATTGTTA AAGACCTCTT GGGACAGGAA     180
AAGGCTCAGT CATAAAATCA GATGCTTATT CATTTTCAGC TGTGTCATTT TGACTCATTA     240
CTTTCAAGAA TAACTATAAT ATTGCTAGAC AGTTCATTAC ACTGAGAAGA ACTTTCCTTG     300
AACTTCACAT GGAGATTGAG TAAAGCTCTT CTATTTGTTT TTTGAAGTAC TCTCTCAGCT     360
CAGGTCTCTT AGCTTTTAGT GTTGGTGTCA GCAAGCCATT TTGAACTGAG AACATGTCAG     420
AATGGATGTG AATGGCTTTA ACCTGCTCAA AAGAATGGAG TCCACTTTCT TTTCCTAACC     480
TCACCATATC TTCCAAAATG GCTTTCTTCA GATCCTTATT TGTGCAGAGA TCTGCATATG     540
TTCCTTCAAT TCCTCTCTTC TGGGCCCAGG AGGGCATAAC TTCAGGGTCA GGCACAACAA     600
TGCCTACCAA AAAGGCCTTT AAGCTGTCCC CATGGACATA GATTTGCGCC ACAGGTTGGC     660
TCCGGATGTA GATGTTCTCA ATCTTCTCGG GTGCAACATA TTCTCCCTGA GCAAGTTTAA     720
ATATATGCTT TTTCCGATCA ATAATTTTAA GAGTTCCTGC CGGCAGCCAT TTTCCGATGT     780
CTCCAGTGTG AAGCCAGCCA TCGCTGTCCA GGGCCTCCTT CGTCCTGTCT GGATCTTTCA     840
AGTAGCCTTT GAACACATTT GGTCCTCTCA CACATATCTC TCCCTCTCCT TTGCAGGCCC     900
AGTAGTTCAG TTCCTCAACA TCAACGAGCT TGATATGATT GCAGGGAAGT GGCGCCCCTA     960
CGTGCCCTGA GGTCCAGTCG CCAGGAGTGG TGAAGGTACA TCCAGCTGTG CACTCAGTTT    1020
GGCCATAACC TTCATAAACC TGGCACCCTA GAGCTGCCCG GAGAAATCCC AGAACTGTTG    1080
GTGATGCTGG GGCTGCTCCA GTAACAATCA TCCGCACACA CCCACCAAGA CTGGCCTGAA    1140
TCTTATTAAA GAAGAGTTCA TCCCAGATAC TATCATTCCT GATGATTCCA CTCCGGACCT    1200
CGGCTTGCTT ACGCTTTGCT GCAAACTCCA GGAGCCAGCG CTTTAATGGT GTGTTTGCCT    1260
GGCTGAAGAT CTTGTCGTAC ATCCGGTTCA GCAGTCGTGG GACCACAGGG AAGATGGTGG    1320
GGCATAGAGC CTTCATGTCA TCTGAGAGAA GGCGGATATC TCCCTGGAAG AAGCCAACAC    1380
GCCCTCCGTG GCAATAGACG ACAGACTGGA TTACTCTCTC AAACATGTGA GCCAGAGGCA    1440
GGGAGGAGAT GAGCACATCG TCCTGTCTCG GAAAGATCAC TTTCTCTGTC ACTTTCAGAA    1500
AGCCTGAGAA ATCGGCCACC ACGTTCCCAT GGGTAAGCAT CGCACCTTTT GGGTTCCCTG    1560
TCGTGCCGCT TGTGAAACAC ACAATGGAGA GGTCATCAGG CTGCGGGGGC ACAGGAGCCT    1620
GGTGATTCTC TTGGCCACAG TCCTCCACGG CCTGCATGGA CTTAATGACC ACCCCGCACT    1680
TCTGCCCTCT CTCTTTCAGG GCTTCTTCGA ATGGGTCCAT GAGGATGATC AGCTTGAGGC    1740
CTGGAGTCTC CTTCCTCTCC ACATGCTCTA GCAGAAGCAC AGCCTTCTGA GGTTTGTCCA    1800
CAATCACGGT GCTGATGTCC GCTGTATTGA TGATGTGGCG GATAGCCCCA GGGCCCAGGG    1860
TGTCATAGAG CGGGACCACC ACCATGGAAT ATGTGTAGCA GGCCAGCTCC ACGATGATCC    1920
ACTCTGGCCG ATTTTGTGCA AAAACACCAA TAAACTGATC AGTGCATGCT TTACAATTGT    1980
```

```
GCTGGAGAAG TCCGGACCCC AGAAATTCAG CCCTGTCGGC CACCTCCTGG TAGGACAGCC      2040

ACTGGTAAGG CTGCTTAGGC TTCCTGAAAC CAAGACAGGG CCCATTCCCT GAGATGCTAA      2100

GCCCACGGCG GAACACCTGG TACATGGTCC GGGCATCATC ATAGTAGTGG GTAAGTAGCT      2160

GAGGGCCAGA CCCAATCACA GATCGCCGTG CCCCGCCACT GTCCTCTACT TCTTCTGACT      2220

GCATCAGGAG GTTGCATGGC GGCTGCAAGG CCTTTGGCCG GTGAGTGAAC CAGTAGGCAA      2280

GGATGGCAGC CAGGGCACCC ATACTCACGA GGGTGGTGGC CGAGAGGCTG CGGAAAAACT      2340

GTCCCAAGTC ACCTAGCTCA GGCAGTCGCA GTATCCTCAG GATCTCCTGT GTCTGCATCT      2400

TCTCAGAAGT GAGAGG                                                      2416
```

(2) INFORMATION FOR SEQ ID NO:62:

(i) SEQUENCE CHARACTERISTICS:
        (A) LENGTH: 1698 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: TS2.seq (xi) SEQUENCE DESCRIPTION: SEQ ID NO:62:

```
CCTGTGAACA TTGACAATAT ATTACTTTTA GTGGTACACA GTTCTTGAGA AAATGTCTTG        60

ATTTTTACAT TGCCATTTGT GATATTTTTA GCAGTCCACC ACAATATCAT TTTTATAATA       120

AAAATAAAAT ATACTCATTG ATGATAGAGA AAATATTGTT AAAGACCTCT TGGGACAGGA       180

AAAGGCTCAG TCATAAAATC AGATGCTTAT TCATTTTCAG CTGTGTCATT TTGACTCATT       240

ACTTTCAAGA ATAACTATAA TATTGCTAGA CAGTTCATTA CACTGAGAAG AACTTTCCTT       300

GAACTTCACA TGGAGATTGA GTAAAGCTCT TCTATTTGTT TTTTGAAGTA CTCTCTCAGC       360

TCAGGTCTCT TAGCTTTTAG TGTTGGTGTC AGCAAGCCAT TTTGAACTGA GAACATGTCA       420

GAATGGATGT GAATGGCTTT AACCTGCTCA AAAGAATGGA GTCCACTTTC TTTTCCTAAC       480

CTCACCATAT CTTCCAAAAT GGCTTTCTTC AGATCCTTAT TTGTGCAGAG ATCTGCATAT       540

GTTCCTTCAA TTCCTCTCTT CTGGGCCCAG GAAGGCATAA CTTCAGGGTC AGGCACAACA       600

ATGCCTACCA AAAGGCCTT TAAGCTGTCC CCATGGACAT AGATTTGCGC CACAGGTTGG       660

CTCCGGATGT AGATGTTCTC AATCTTCTCG GGTGCAACAT ATTCTCCCTG AGCAAGTTTA       720

AATATATGCT TTTTCCGATC AATAATTTTA AGAGTTCCTG CCGGCAGCCA TTTTCCGATG       780

TCTCCAGTGT GAAGCCAGCC ATCGCTGTCC AGGGCCTCCT TCGTCCTGTC TGGATCTTTC       840

AAGTAGCCTT TGAACACATT TGGTCCTCTC ACACATATCT CTCCCTCTCC TTTGCAGGCC       900

CAGTAGTTCA GTTCCTCAAC ATCAACGAGC TTAATATGAT TGCAGGGAAG TGGCGCCCCT       960

ACGTGCACTG AGGTCCAGTC GCCAGGAGTG GTGAAGGTAC ATCCAGCTGT GCACTCAGTT      1020

TGGCCATAAC CTTCATAAAC CTGGCACCCT AGAGCTGCCC GGAGAAATCC CAGAACTGTT      1080

GGTGATGCTG GGGCTGCTCC AGTAACAATC ATCCGCACAC ACCCACCAAG ACTGGCCTGA      1140

ATCTTATTAA AGAAGAGTTC ATCCCAGATA CTATCATTCC TGATGATTCC ACTCCGGACC      1200

TCGGCTTGCT TACGCTTTGC TGCAAACTCC AGGAGCCAGC GCTTTAATGG TGTGTTTGCC      1260
```

-continued

```
TGGCTGAAGA TCCTGTCGTA CATCCGGTTC AGCAGTCGTG GGACCACAGG GAAGATGGTG        1320

GGGCATAGAG CCTTCATGTC ATCTGAGAGA AGGCGGATAT CTCCCTGGAA GAAGCCAACA        1380

CGCCCTCCGT GGCAATAGAC GACAGACTGG ATTACTCTCT CAAACATGTG AGCCAGAGGC        1440

AGGAAGGAGA TGAGCACATC GTCCTGTCTC GGAAAGATCA CTTTCTCTAC TTCTTCTGAC        1500

TGCATCAGGA GGTTGCATGG CGGCTGCAAG GCCTTTGGCC GGTGAGTGAA CCAGTAGGCA        1560

AGGATGGCAG CCAGGGCACC CATACTCACG AGGGTGGTGG CCGAGAGGCT GCGGAAAAAC        1620

TGTCCCAAGT CACCTAGCTC AGGCAGTCGC AGTATCCTCA GGATCTCCTG TGTCTGCATC        1680

TTCTCCAGAA GTGAGAGG                                                      1698
```

(2) INFORMATION FOR SEQ ID NO:63:

(i) SEQUENCE CHARACTERISTICS:
        (A) LENGTH: 2416 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: FL.seq (xi) SEQUENCE DESCRIPTION: SEQ ID NO:63:

```
CCTGTGAACA TTGACAATAT ATTACTTTTA GTGGTACACA GTTCTTGAGA AAATGTCTTG         60

ATTTTTACAT TGCCATCTGT GATATTTTTA GCAGTCCACC ACAATATCAT TTTTATAATA        120

AAAATAAAAT ATACTCATTG ATGATAGAGA AAATATTGTT AAAGACCTCT TGGGACAGGA        180

AAAGGCTCAG TCATAAAATC AGATGCTTAT TCATTTTCAG CCGTGTCATT TTGACTCATT        240

ACTTTCAAGA ATAACTATAA TATTGCTAGA CAGTTCATTA CACTGAGAAG AACTTTCCTT        300

GAACTTCACA TGGAGATTGA GTAAAGCTCT TCTATTTGTT TTTTGAAGTA CTCTCTCAGC        360

TCAGGTCTCT TAGCTTTTAG TGTTGGTGTC AGCAAGCCAT TTTGAACTGA AACATGTCA         420

GAATGGATGT GAATGGCTTT AACCTGCTCA AGAATGGAG TCCACTTTCT TTTCCTAACC         480

TCACCATATC TTCCAAAATG GCTTTCTTCA GATCCTTATT TGTGCAGAGA TCTGCATATG        540

TTCCTTCAAT TCCTCTCTTC TGGGCCCAGG AGGGCATAAC TTCAGGGTCA GGCACAACAA        600

TGCCTACCAA AAAGGCCTTT AAGCTGTCCC CATGGACATA GATTTGCGCC ACAGGTTGGC        660

TCCGGATGTA GATGTTCTCA ATCTTCTCGG GTGCAACATA TTCTCCCTGA GCAAGTTTGA        720

ATATATGCTT TTTCCGATCA ATAATTTTAA GAGTTCCTGC CGGCAGCCAT TTTCCGATGT        780

CTCCAGTGTG AAGCCAGCCA TCGCTGTCCA GGGCCTCCTT CGTCCTGTCT GGATCTTTCA        840

AGTAGCCTTT GAACACATTT GGTCCTCTCA CACATATCTC TCCCTCTCCT TTGCAGGCCC        900

AGTAGTTCAG TTCCTCAACA TCAACGAGCT TGATATGATT GCAGGGAAGT GGCGCCCCTA        960

CGTGCCCTGA GGTCCAGTCG CCAGGAGTGG TGAAGGTACA TCCAGCTGTG CACTCAGTTT       1020

GGCCATAACC TTCATAAACC TGGCACCCTA GAGCTGCCCG GAGAAATCCC AGAACTGTTG       1080

GTGATGCTGG GGCTGCTCCA GTAACAATCA TCCGCACACA CCCACCAAGA CTGGCCTGAA       1140

TCTTATTAAA GAAGAGTTCA TCCCAGATAC TATCATTCCT GATGATTCCA CTCCGGACCT       1200

CGGCTTGCTT ACGCTTTGCT GCAAACTCCA GGAGCCAGCG CTTTAATGGT GTGTTTGCCT       1260

GGCTGAAGAT CTTGTCGTAC ATCCGGTTCA GCAGTCGTGG GACCACAGGG AAGATGGTGG       1320
```

```
GGCATAGAGC CTTCATGTCA TCTGAGAGAA GGCGGATATC TCCCTGGAAG AAGCCAACAC    1380

GCCCTCCGTG GCAATAGACG ACAGACTGCA CCATACGCTC AAACATGTGT GCTAAAGGCA    1440

AATAGGAAAT GTGCACATCC GCACAAGTGG GAGCCCACTG ACTCTCTGTC ACTTTCAGAA    1500

AGCCTGAGAA ATCAGCCACC ACGTTCCCAT GGGTGAGCAT CGCACCCTTT GGGTTCCCTG    1560

TCGTGCCGCT TGTGAAACAC ACAATGGAGA GGTCATCAGG CTGCGGGGGC ACAGGAGCCT    1620

GGTGATTCTC TTGGCCACAG TCCTCCACGG CCTGCATGGA CTTGATGACC ACCCCGCACT    1680

TCTGCCCTCT CTCTTTCAGG GCTTCTTCGA ATGGGTCCAT GAGGATGATC AGCTTGAGGC    1740

CTGGAGTCTC CTCCCTCTCC ACATGCTCTA GCAGAAGCAC AGCCTTCTGA GGTTTGTCCA    1800

CAATCACGGT GCTGATGTCC GCTGTATTGA TGATGTAGCG GATAGCCCCA GGGCCCAGGG    1860

TGTCATAGAG CGGGACCACC ACTATGGAAT ATGTGTAGCA GGCCAGCTCC ACAATGATCC    1920

ACTCTGGCCG ATTTTGTGCA AAACACCAA TAAACTGATC AGTGCATGCT TTACAATTGT     1980

GCTGGAGAAG TCCGGACCCC AGAAATTCGG CCCTGTCGGC CACCTCCTGG TAGGACAGCC    2040

ACTGGTAAGG CTGCTTAGGC TTCCTGAAAC CAAGACAGGG CCCATTCCCT GAGATGCTAA    2100

GCCCACGGCG GAACACCTGG TACATGGTCC GGGCATCATC ATAGTAGTGG GTAAGTAGCT    2160

GAGGGCCAGA CCCAATCACA GATCGCCGTG CCCCGCCACT GTCCTCTACT TCTTCTGACT    2220

GCATCGGGAG GTTGCATGGC GGCTGCAAGG CCTTTGGCCG GTGGGTGAGC CAGTAGGCAA    2280

GGATGGCAGC CAGGGCACCC ATACTCACGA GGGTGGTGGC CGAGAGGCTG CGGAAAAACT    2340

GTCCCAAGTC ACCTAGCTCA GGCAGTCGCA GTATCCTCAG GATCTCCTGT GTCTGCATCT    2400

TCTCAGAAGT GAGAGG                                                   2416

(2) INFORMATION FOR SEQ ID NO:64:

(i) SEQUENCE CHARACTERISTICS:
        (A) LENGTH: 406 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
         (C) INDIVIDUAL ISOLATE: FL2.seq (xi) SEQUENCE DESCRIPTION: SEQ ID NO:64:

TGGTGTCAGG GGNCAACAGA GGCCGAAGGC GCCCTCTTGA AAAAAATAA GCTACAAGAT       60

GAGTAGAGTG GTTTACACAG AGGACTGTGG AGGTGGTGGG TAATAAACTT AAGCACCAGT     120

TTTAATCAAG TACGGGCTGG ATAATTAGAC AAGATATNGG NNNCTGAGCC TCGCGTCAAC     180

TGAATCGGCA GCTCGGCCGC CTGTTGCCAC AGGCTCCTTT CTCCACGGCG TCCTTGCGGG     240

ACCGCCAGAG TGTGCTTGGC TTCCGCGTAT CCGTGTGTCT GCGCGTCGCC GGCGACTGTC     300

CCGTGTTTCC CTGTGAGGCT GCCACGCCCA GGCGTGCATG TGCGTCTCGA GACCTGTGGA     360

CCTGGGCGGC AGAAAGGCTT CCCGTGGCTG TTGCCCGCTG ACACCA                   406

(2) INFORMATION FOR SEQ ID NO:65:

(i) SEQUENCE CHARACTERISTICS:
        (A) LENGTH: 234 base pairs
        (B) TYPE: nucleic acid
```

(C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: G205a.seq (xi) SEQUENCE DESCRIPTION: SEQ ID NO:65:

```
CAGGCTCATG GTGTGGAAGT CAGACCGGGA GTCTCCTGGA GCAGACTCAC AGTGTAGGGG      60

GTCAGCAGAG GCAGCAGCTT TGGGAATCCC GGCACTGCAG CCTCAGGGGT NGGCTCGCTG     120

AGTGGGTCAA GGTCTTTAGG GTTCTTGGGC CCAGCCTTGG AGCCTGCCCT CCCAGCCCTC     180

CTGACATTCT TAGAAGCACC TACTTTCCTG CCTGAAATCC TTTCCTGATT TAAA          234
```

(2) INFORMATION FOR SEQ ID NO:66:

(i) SEQUENCE CHARACTERISTICS:
        (A) LENGTH: 161 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: G205b.seq (xi) SEQUENCE DESCRIPTION: SEQ ID NO:66:

```
GCTGTATAGT ATTCCACTGT GTATATATAG TTTTGGATCT TATCGCAGTG CCTCAAGTTC      60

TGTGAAGGAG AGAATCTGGA TAATTGTATC AGGAGGTCCT TAGACCATAT TTAGGATCCT    120

TCCATTGGGA CTTGGGCAGC AAGGTTACCA AAACTTAAAT G                        161
```

(2) INFORMATION FOR SEQ ID NO:67:

(i) SEQUENCE CHARACTERISTICS:
        (A) LENGTH: 445 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: G205c.seq (xi) SEQUENCE DESCRIPTION: SEQ ID NO:67:

```
CTCTCCTTCT GCATCCCCGA CTCTCCTTGA GAACCTATTT GGCAGAAGCT CTCCACCCAG      60

CAAGTCCGCA GCTTGATGAG CTCCCTCCTG TGTTAACTGG AACCCCTGCT GTACTTCATT    120

CCACATAATA GTTCATCGGA TCCAAAGTCC CCACCTGCTT TGGAAGCAAC CACCTGCTCT    180

TCTCATAACT CTCCTCCAGT TTGTGCAGTG AAGAATCAAC CTTTATCCAA GAAGTCTGGC    240

CTTTGCCCTG GCTCTTGGGA GGTCCTACCA GCTACAAACC CTTGGAGTAA ACAACGTGGC    300

TAGTCCTTGT CACCAGTTCC CAGGAGGTAG CCCCAAATTC CTAGGGATTT CCCAAGTGAT    360
```

```
AGGAGTATCT TATTACTCAT GGTGGTCTCT GAGAGTTTAT GTGAGTGAAG TGGCTCATGG      420

TGGGCCCTAG GTAGTTTTTG CTGAC                                           445
```

(2) INFORMATION FOR SEQ ID NO:68:

(i) SEQUENCE CHARACTERISTICS:
        (A) LENGTH: 1661 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: G221.seq (xi) SEQUENCE DESCRIPTION: SEQ ID NO:68:

```
TCCAGGTCAG CTACACACTG TATGCCTGAG CCCATGTTAA TCTGTTGTAG TGAAGACACA       60

TTTGGCAAGC ACAGTGGCTG CAAATGGGGC TACTGTTGAA TTGGTAGTAG CCTGCTGTCA      120

TCTTTCAGGA TTTAACTGGG TTTTGCTGGT AAATTAAATG AAGATATGAC GGACTCCCTT      180

TTAGGTCTAT AATGGTGGCA ATAATTTCTG CCATTAACCC TGGAATGTGA TATTGTTCTT      240

GATTTACTAT TTTGCCTGGA ATGGGAAGGT TTTGAAGGCT TCCACTTGGC TTTCTTCACT      300

ATGATCACTC TCACCATGCA GGCCAAGGAC CCAATGTAGG GGCTGTGCTA ATTATCAAGT      360

GTGTTGATCT GATTATATCA CTGTGGGTCT GTGGACCCAG AGGACCTGCT ATTAGCAGAA      420

CTCAGGACAG GAATCTATCA CCTGGCCCAC ATATACCCCT CATTCTAATG AGAGGATTGT      480

GGCGCCACTT CAGGTACCTA GGTAACAATG TCAATTCTAA TCCCGGGTTC AATAGTCTTT      540

CACATGTTAG GATATTCTCT TTCCTAGTAT GTAGCTATCC AAGTTAAGTG CCCACAGGTC      600

CCCCTGGGAA AGGGCTGGGG AAATCATTAT CATGCACACT TGCTGTGGTG GTGTGGGACT      660

CTTCCTTCTG GGAGATCTGG CATCTTCTTC AATCAGTAGG TTCTAAGTCT GAAAACTGGT      720

TCAGATCTGG AAACTCGGCA GGTTACTTTT TATTGGGGTG ACTGGACTCA TTATCCATGA      780

TTGATTTCTT TTTCTTGCAC AGAATAACCC GCAGCACTGT TGGCTGGCCA TCTATTGTGA      840

CCCTCCAGAT GCTATGTTTT ATTAACCATG TCCATAACTC CCCGGGAGCC AGGCCCTCTT      900

AACAGCCATT CCAATCTTGC CACCCAGACA ACTGGGCCAA GTGCTATGAC TTGGCCTCTA      960

TTATCTCAGA GTCCTATCAC CCCTACTGCT ATCAGTGAGC CCAGTTCTGT GACATTTCCT     1020

ATCAATGCTG GCCTATTTTA GCCACCATTT TAGTTCTTGG TGATACTGGT GCCCTTCTTT     1080

CCAATACATT TCTTGTTTTG GTATCTTCTT GGCCCTCAGG CGAGTATTCT GAATTTGCTT     1140

AGTATATTTA TTCCTGCACA CCCACGTCCT TCATAGTCTG CCATAGCCAT TCTGGCTACC     1200

CTCACTTAAT ATGGGCCATC CTCTTTCCAT GCTTCTAGGA GCCATCCAAA CGATGTATTT     1260

GCACCATCTC TTGGGCTTT GCCACAGTTT TAAATACTTT ATCCTGGAAG AATGTTCCCA     1320

TATCCATAAA CTCTTTTGTT CAAATTTCTG TTCCACCCCC TTGGTCCAGA ATCCAGTCCT     1380

GTGCATACTC TCCAAGCTCC TGCTAGTACT CTCTGGATAT GACCAGAATT TCCTTTGAGG     1440

TATAGTCCTT TTCTACACTA GCAAGTTCAG CATGTCTGGC CAGGTTAGGT TTTGACTTAA     1500

CCCTAGTTAT TGGCCTAGCA CAAAGAGGTA ACATGGAATG AGAGCATGTC TTGCAGGACA     1560

GAAGCCTCCG CATTTTCTTT TTAAAGTAAG AAGCAAGTTC TAGCTTTTAA CAGAGATGAG     1620
```

TAGGTCACTT CTGCAGGTCC AGAGTGTTTA GTGAAATCTG A                               1661

(2) INFORMATION FOR SEQ ID NO:69:

(i) SEQUENCE CHARACTERISTICS:
        (A) LENGTH: 1379 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: G238con.seq (xi) SEQUENCE DESCRIPTION: SEQ ID NO:69:

```
CTCTGTGCAC TGTAGNGTCT TCTTGTGTAC CAGCACTTTT TTCTTCCCAT TTCTTTCTCC      60
ATGTTTACCA TCAACACTGT GAGAATAACT GAAGTTTCCT TATCCAAAAA AAGGGTGCTA     120
CTCCAGATTC CGCCACTACT GTTTTCGAAA AGCACAAAAC CAACAGAGCC TCAGGGGGGG     180
CTGACCCTCT TTCTGGATCC CACCTCCATC CCCCCGAACT TACGTTGTGC TTTCCTCAGC     240
AGCCACCGAG GCCTCCAGTT CCGTCTCCAA AGATGATGGG TTCCTTCCAG TGGGTGCAAA     300
GTGAGAGCCC CAGTGATTGG TGTTCATAGT GGGTCAGTGT GAACAACGCC CAATGGCCTG     360
CCTGGGCCAG CTGGGGCCTC GTTTTGCTTT GGTCTGAAAG ACATTTTTGT TTTCTGGTGA     420
GAACAGCCCC AGCCTGGCCA GGAGCCGGCC AGCGGCAGGA ATACAAACCC TTTCATGTGA     480
CAGACCCAAG TGGAGTGATG CCCTCCTGCC AACAGCAGGC CCTCCCCTGC CGCTCCTGGG     540
AGGCGGCCAT TTGCATATTT CCCATTCATC CTGGCCTTGA AAAGGAGGCC TGAGTTCCCA     600
GTGCTCCTGC CCGCTGAGGG CTGGGCCGCT CCAGTCTAGT GTTAACTCTG TGGACACTGT     660
AGGCTCTCAC AGGCCAACAG CAGAACTTGA CCGCTTGCTG CCGGAGGGAG AGCAGCTTAA     720
GGCTGCAGCT GCTGTGCCGC CTGACCTCCA GAGGGGGGAT TCAGGAGGTG GCAGATTCCC     780
GTTGACCAGC ACAGCCTTTT GCTAAACTGG AGGAAATTCA GATTTGTTTC TTCTTGAGGC     840
ATTCAGAAGA GGAATTTTGT CAGACTATGG GGATGCCAGA ATATTCAGCT ATTTACCAAA     900
TTTGCCAGAA AATGTGCCCT TAACCAAGGG CCAAACTCTT TTTGTCTTGC TCACTTTCTA     960
GTCTACAAAA AAATTCAGTG ACTCTGGAAT GGTAGGTGAA GGAGCCATGC CGGATCCTGG    1020
CTGCAGCAGC AATCCCTTTG CCAAGGATGT AGGAGCACAG CTTGCCTGGG GCACTTTTGC    1080
ATCCCCAGGG CTGAGTGCCA TTAGCTTGTG GGCTGTGACT CTGAAGGCAT GAGGCAGATA    1140
TACAGTACCC ATCACCATCT TTTTCCTTTC TCCCATAGCT AAGTGCCATC CTGCCAGCCT    1200
CAGCTTCCTG CCCCAGTCCT CAGTGCAGAC AGGCCTCTGC CTCCTTCCCG CCACTGTGTG    1260
AGGGCTCCTG CCAGGGGCCC AACATCTTA CAGGCTCTTC CTGTGACTTA CCAACCCACT    1320
TCTGTCCCTC TTCGATAGCC CTGTTCTCTA CCCTTTCCCA CCCAGCTCGG ATCCTCTCC    1379
```

(2) INFORMATION FOR SEQ ID NO:70:

(i) SEQUENCE CHARACTERISTICS:
        (A) LENGTH: 2661 base pairs
        (B) TYPE: nucleic acid
        (C) STRANDEDNESS: double
        (D) TOPOLOGY: linear (ii) MOLECULE TYPE: cDNA to mRNA -continued (iii) HYPOTHETICAL: NO (iv) ANTI-SENSE: NO (vi) ORIGINAL SOURCE:
    (C) INDIVIDUAL ISOLATE: G229con.seq (xi) SEQUENCE DESCRIPTION: SEQ ID NO:70:

```
TCTCTAGACC CTTCCTGCTT CTCTCCCCAC AGCAGCCACC CATTAATTCA TTACATAAAT    60
ATGTACTGAG CACCTACAAA GTGTCAGGAA CTGTGCCAGG CTCTGAAAGG AAACCAACCC   120
TTGAGGAGCT TACACTTTAG GGGTTAGTCT GGCTGTGTGT CATAAGGGTT ACCTGCCAGC   180
TCAGCATGAA CTCCAAGCCC TTTGGTCTGA CCTAAGACCC TCCCTTACTG CCCTGGCCCC   240
GACAGCCCCT GCAGATACCT CTAGCCTCAT TGCTCACCAT CCATCTCCTT CATATCAGCC   300
CTGGACCCCA GTAACACGAC CCAGACCACA GCACTCCCAC CATCACCTGC TACCCCTGCC   360
TGGAATGCAC CCCAGACCAA ATGGTTGACA TCTGTCTCCA CAATGGGGTA AGACTAATGT   420
CCAGCGGGAG GTGGAGAGGT CCTGCACTGG GGCCTCCTCT TCCTCAACAC CTACTCTGAG   480
GCTTGCCTGC CCACCTCTTA CGCCACAGGG GTGGACTGTT ATCTGTTCCT CAGGGGACTG   540
TGAGGGTCTC TGCTCTGAAC TACTGCTTTA TCCCCCAGCT CGGAGGAGGG CCCCTCATGG   600
CATCAAGTGC CAGCAGTGAC TATGTTCCAG AGTCTGATGA AAGTGAGCCT CTTTTCACCT   660
TTGAATAAAA GAAATGCACA CAGCTTTTAC AGAAGTCCGG ATGGAAAGGC AACATCCAAT   720
TTTCCAAAGT TTAGAAAATG TTCTTGGGAC CAAGATCAGC AACAGGCTAT AAGCAGGTAC   780
TAAGTACACA GCCAGGGCTG TTGTTTTCAT TATTCTTATC AAAAATAGCA TCTGTGAGGG   840
AGCCAAGAGG AGGCCCTTGG GGCCATCCAG GAGCCAGGGG AACTGGGAGC CAACACCAG    900
CACAGCTGCC AGCTCTTTTT CCCACTTAAC GGATTCGGGA ACCATCTCAA AGGAAGCTGC   960
AGGAGGGAGG GAAGCCCAGC TCTCTGGGAA TGTGTCACAC TTCCTCCAGT TAGGCCTGGG  1020
GCAGCCCCAA GCTCTCCTGA TGGAGGCCCT GGCTCCTATC CAGGCCTCTT CCTCTACCAG  1080
ACTGGATAAG GGTGAGGTCA TGTGCTGGGG AAGGGAGGCC AGGGAAGCAG CAACTGGGTT  1140
GGAGCCAGTC AGAAACAACA CAATAACAGG ATAACTCATA GTCTCCCCTC TCCCCTTACA  1200
CTCCAGGAAG CTGTCCCTGA GTGAACTCCA TACCCCTCAG GTCCCTTCTC CCACTGGGAC  1260
CTCTCTGGGG CAGATTCTGT GGGTGCCTCT TAGTCCTCAA CTGAAATGGA AGCTCTCTCT  1320
CTTCTCAGGG CTAGGGGCAG CACTGTGAAT CAGACAGACC CTAATGCCTC CTCTCACCAA  1380
TCCAGTCCTG GACATGGGCA GCAACCAGTG TTGGAACCCA GGTGGAAATA AGAGGAAGCT  1440
GCCAGAGCCT CGAGCCATAC CCTGGGCCAT GGTCACACCA AAGGTTCTTG TGCCTATGGG  1500
GCTGAGGGAC AGAGATATGC AGCCTTGGGC TCTGAGATCA AACAAAAATG GGTGTGGGCC  1560
TGGGTCCCCA AGTTACAATG AACCCCCCTG TTAGGAAGGT GCATCTGACC TTAGACTCTG  1620
TCAGGCTGAA GGACCAGGTC CCCAAGTTAC AATGAACCCC CCTGTTAGGA AGGAGCATCT  1680
GACCTTAGAC TCTGTCAGGC TGAAGGACCA GGAGTCACAA GCAGACAGAC AGACACAGCA  1740
GGACCATGAC AGGGGCAGAC AAACAGATAG GCATAGCTCA GGCTCCTGGC AGTGATGAGT  1800
AAACGGACAG ACACTGATAG ACAGTTAGAC TCAGCGAGAG CCTGGAAAGG ACAGATGGAG  1860
AGACAAGAGG GAACGCTGGC AGTGAAAGAC TGACAGACAT AGAGGAGATG GCGGACTTGG  1920
CAAGAGCCCC TGGCAGGGAC AGACAGAGAC GCAGTTGCAA GCTGTGGTCA GGTTAAAATG  1980
TGGCCATTCT GTCTCTGAGC TCAGCCCCTG ACTGCAGATC CCGATTCTCT TGGAGGTTCC  2040
TCCTCTTGGC ACTGTGATCA GAGACTTTGT GGGACTCTTG GGACCCATTT CTCCAGGACT  2100
```

| | |
|---|---|
| ACAATGCCCT CAACCCCACA AGTCCCAGGA AGGTAGTAGG CTGTGGCCCT CACTGTCCCT | 2160 |
| GGAGTCAGAC TCAAGAATCA ATCCATTCTC CTGGTTTTTT CCTCCCCTTC CTGGCCTGTG | 2220 |
| GGGCAGAGAA AGCCTCCTCG ACATCTCTCC TGGGGCCACC TACTCCCAGC ATGGTGGCTG | 2280 |
| TGCTTGTCGT GGAAAAGGTC CTTTTAGGAA CCACTATGAG TCCAGACTCT GTTGGCACAG | 2340 |
| GGGGCGGTGC CCAGAAGAGG CTATAGTCCG GCATTTGCAC GACTATCCGA GGATGTTGAG | 2400 |
| CTCCACCTGG CCGCCTTCTC TTCTCACCAC CCCTCATGAC CTCCAGGCCC CAGAGGCCTG | 2460 |
| AGGGCCTAAA AGGTTTTGAC CCAGGGGAGC AATTCCAGGC CAGGTGAGGA TGGGGTGATT | 2520 |
| AGTCCCCTTC ATAGCTGCAG AGACTGAAGC TGACTTGAAC ACACTCTGCT CTGAGGCTGT | 2580 |
| AGGGTCCAAG AACCCCCCTG GGGTGAGCTG AGGTTTTTCT ACTTTCAGGG GACCGTTGTG | 2640 |
| CTGAAAGCAT GACGAGGCTG C | 2661 |

(2) INFORMATION FOR SEQ ID NO:71:

(i) SEQUENCE CHARACTERISTICS:
        (A) LENGTH: 863 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: G248.seq (xi) SEQUENCE DESCRIPTION: SEQ ID NO:71:

| | |
|---|---|
| CTATGCTAGA GAAAAAGGGA GGTAGTGGTT TCATCCGCCA CTACTACCTA TGGATGTGAA | 60 |
| CAGAACCTCT GCTCCTGATG CAGACCCCTG GCCCTTTCCC AGCTCCTATT CTGTTTTGAC | 120 |
| TTCTGCACAC CCCTTTTTCT GACCCTGATA CTATCCCAGA TCATTATTCT TCCTCTAGTC | 180 |
| CTACCCTTGT TCTAGCCAGT GCCCCAGACC CAAGGTGAGC TAAGGGACAG TCTCTCAAAG | 240 |
| TCTGGGCAGA GAGCCTCAGG AAGTTGGGGT ATGGCTGAGA GAAGAGGGGA GTGCAGGGGG | 300 |
| ATAGGCTAC AGACTCTGAA TGCTTGACCT TCCTTATTTT CTGTCTTTGA ACTTATTTCA | 360 |
| ACAGAGGAAC CCTTATCATC TAGCCCTGTG GCTCTCTAGT ACCTTGTACC TGCTTCCTGT | 420 |
| CCCATAATTG TGAGCGTTTA GCTGTGGTGC AGGTGAGAGA CCCATTCTCC CACCCTCAGG | 480 |
| AGCCAGGAAG GCCCACCAGT ATGGCAGGGA GGCCTAGGCA GAGATATACA GGAGAGCAGA | 540 |
| GACGTCTGGA GCTAGGTCAC CGGTGGTCAG CAGGGCCTCC TGCAGAGGGA GCAGCCTCCT | 600 |
| TTGGCCTTTG CTTGTCTGAC TTCTAATGAT CCTGTAAAAA TTAGTTTTGT TTTTTAAGCA | 660 |
| CCCCAATGAT GCATGAATAC ACTCTTTTGT CAAATCTTAA AAAGAGAAAA TCCTTTTTTT | 720 |
| TTTAAATAAA AAAGAAAGTT ATTTAGTCTT AAGATTGTAA AACTGTAAAG TTAAATAAAG | 780 |
| TGGCCGCCCT TTGGCTGCCC TGATCCCCAT CCCCTACTCC AGCTTCTGCA AGTAACCACA | 840 |
| ATTCTCAGCT AGGTGTATAT CCT | 863 |

(2) INFORMATION FOR SEQ ID NO:72:

(i) SEQUENCE CHARACTERISTICS:
        (A) LENGTH: 1378 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
            (C) INDIVIDUAL ISOLATE: G248a.seq (xi) SEQUENCE DESCRIPTION: SEQ ID NO:72:

```
GCCGCCCGGG CAGGTTGCTG AGTCTCTGAA GGTAGGAGTG GGAAGTCTCG CATTGGAAAG      60
GCCTTCTTAG GTGCAGTAGT ATTTGTTATT TTACACCTTA ACCTCAAAGG AAGTCCTTCT     120
TTTTCTTGGG ATGGAGCACT TTAGTTCTCA TAACTCTTCT CTGAAGTCAT TGCAGAGTGG     180
GTGGAGGAAG GTGAGGGTGA TGCTTGGGTC TGAATTTTCT TGGTAAACTT ACAAGTGGAT     240
CTATCAAAAA CCAGAGGGTT TTTTCTTAAC CACAACACCC CCAGAATTC CATTTCCTGC      300
AGATGTAGCA GCAGCACGTC TAGCCATCTT GGCCCAGGCC TCTGGACCAT GCCTTGGGAG     360
GGCTCTGCCC TCTGCCTTGA GTTCCATTAG AACTTCTCCA GTGGAAAGAG TGAGTTACTT     420
TGCCCTGGCC TGGTGGGCAG GCTTTTTCCT CTCTGACTTG GCTAAATGAA ATGGGATTTA     480
AGGTAGCTCT CCCTGTGGGT AAAAGACATT TTGCTCTATG CTAGAGAAAA AGGGAGGTAG     540
TGGTTTCATC TGCCACTACT ACCTATGGAT GTGAACAGAA CCTCTGCTCC TGATGCAGAC     600
CCCTGGCCCT TTCCCAGCTC CTATTCTGTT TTGACTTCTG CACACCCCTT TTTCTGACCC     660
TGATACTATC CCAGATCATT ATTCTTCCTC TAGTCCTACC CTTGTTCTAG CCAGTGCCCC     720
AGACCCAAGG TGAGCTAAGG GACAGTCTCT CAAAGTCTGG GCAGAGAGCC TCAGGAAGTT     780
GGGGTATGGC TGAGAGAAGA GGGGAGTGCA GGGGGATAGG CATACAGACT CTGAATGCTT     840
GACCTTCCTT ATTTTCTGTC TTTGAACTTA TTTCAACAGA GGAACCCTTA TCATCTAGCC     900
CTGTGGCTCT CTAGTACCTT GTACCTGCTT CCTGTCCCAT AATTGTGAGC GTTTAGCTGT     960
GGTGCAGGTG AGAGACCCAT TCTCCCACCC TCAGGAGCCA GGAAGGCCCA CCAGTATGGC    1020
AGGGAGGCCT AGGCAGAGAT ATACAGGAGA GCAGAGACGT CTGGAGCTAG GTCACCGGTG    1080
GTCAGCAGGG CCTCCTGCAG AGGGAGCAGC CTCCTTTGGC CTTTGCTTGT CTGACTTCTA    1140
ATGATCCTGT AAAAATTAGT TTTGTTTTTT AAGCACCCCA ATGATGCATG AATACACTCT    1200
TTTGTCAAAT CTTAAAAAGA GAAAATCCTT TTTTTTTTAA ATAAAAAAGA AAGTTATTTA    1260
GTCTTAAGAT TGTAAAACTG TAAAGTTAAA TAAAGTGGCC GCCCTTTGGC TGCCCTGATC    1320
CCCATCCCCT ACTCCAGCTT CTGCAAGTAA CCACAATTCT CAGCTAGGTG TATATCCT     1378
```

(2) INFORMATION FOR SEQ ID NO:73:

(i) SEQUENCE CHARACTERISTICS:
            (A) LENGTH: 797 base pairs
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (vi) ORIGINAL SOURCE:
            (C) INDIVIDUAL ISOLATE: G248b.seq (xi) SEQUENCE DESCRIPTION: SEQ ID NO:73:

```
GTGTATATCC TTCCAGACGT CTTTCTATAC ATTTACTTTT CCTTATTGTT TAAACCAATG      60
```

```
GTGAGTTGTC TTTTCTCTTA CTTAAATCTG AAAGTGTTCC TAACCAATTT AATAACAATT        120

GCCTCAGTGC TGTTTATTGA AAGGTTCTTC GTTTCATACT GACATAAAAC GCCAGTTGTG        180

TTAGACCCTG GCCAGGCCTG CTTCCTCAAA GACCCAGAGT AAACATGAAC TGTAAACTCC        240

AAAACTGTAC AACTAGTTTT TAAAGAAAGA TTGCCCAAGA TACTGGCACA AGACTTTTTA        300

AGGCCTAGGA TTTGCATATT AGACCTATGT AATGTGGCTT ACTGAAGAGC AGAGTTCTTG        360

CTTTCTTTGG TAGTGTAAGC TCTTTCTGGT GCTCACACAG GAAGGACTGT AAAGGGCAGT        420

GAGGGCTCGA ATCTGGACTC TTCTGACATG AGGGACATCT CATTTTATGC AGGCTGCCAA        480

GACCATTGAA CTTGGAGGAT GCCTTTGTGA GAAAGCAAGA AAGGCAGTGG GGAGCTGCAG        540

CCCCCACATG CACCTTCATC TCAGGAACAT CCTTTGTACT TTTTTTTTTA ATATTGTACA        600

GAGCTGTTTT TTTTTATTAT ACTTTAAGTT TTAGGGTACA TGTGCACAAC ATGCAGGTTA        660

GTTACATATG TATACATGTG CCATGTTGGT GTGCTGCACC CATTAACTCG TCATTTAACA        720

TTAGGTATAT CTCCTAATCC TGCCCGGGCG GCCGCTCGAG CCCTATAGTG AGTCGTATTA        780

GGATGGAAGC CGAATTC                                                       797

(2) INFORMATION FOR SEQ ID NO:74:

(i) SEQUENCE CHARACTERISTICS:
        (A) LENGTH: 403 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: G248c.seq (xi) SEQUENCE DESCRIPTION: SEQ ID NO:74:

CATTGATGGA ACCAATACAG AAAAAGGATT TTCATCATCC AGGCCTTCTT CTACAGCTGA         60

AAGACTGGCA GCTGGTATAC AACTGTTCCC TGCAAGGATT GGGAGTTAGC AGCTTTATGG        120

ATAAGGGCAA TGCTAGTGCT TGCTTCTGTT CCTTACTAAT AAATATCGTT TGTGACACTT        180

TTTTTCAGAA TAGGGCATTT TTGTCTGTAT TAAAAACCTG TTGAGGCAGG TATCCTTTGT        240

CCTCAATTAT TTTCTTAATG ATACCTGGGA ACCTATCTCC TGCCTTTGGT CAGCAGAAAC        300

TGCTTCTCCT ATTACCTGGA TATTTTTAAG GCCAAACCTC TTGCTAAAAT TATCAAACCA        360

TCCTTTGGTG GCATTAATTT TCAAGTTTAG CTCCTTCAAC CTC                          403

(2) INFORMATION FOR SEQ ID NO:75:

(i) SEQUENCE CHARACTERISTICS:
        (A) LENGTH: 1083 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: G220a.seq (xi) SEQUENCE DESCRIPTION: SEQ ID NO:75:
```

```
GGAAGACACT GATCATCTGT CACAAACTTG GTGAGTCATA AATAGTGCCA CCTAAACCAT      60

GAGATAAACT GGGGGTGCAC CTGGAAACCA GGTAGCCCCC CTCAAGGGCA GGGGCTTTTG     120

TATTATAGGT CTGCTGCTAT TCTCCCAGTA CCCTCAATGG CACATGTCAT GTAGAAGAGT     180

CTCAGTAAAT ACCTGGTGGG TGACAGAATG GAGGTGGGTG ATTCTGTTGA TGAGCAGGCT     240

GGCACCGATG AGCATGGAGT ATCTGCCAGC CCTAGGATGG TGCTGTGTCT GTGTCCATCC     300

ACTGTATGGT TACAAGAACT CAAGGTACCT GGGATCCCTC AGTCCTCACA GACCAGCTCC     360

CAAGCTGGGC ACAAAAGACA ATGTATGTTG AGTGTTGTTT CTGACATGAG ACTACTGGGA     420

CAGTAGGTGT CTGCCTGCTC CAGTATGAAG GATCCCACTA CTTTGTCACT GGATGGCTTT     480

GGGTTGCAGT GGTTTTCTTA CCAAAGCACA ATGACCCTTC AGTGGGGTCA GCTTCAGCAA     540

GATAAAGGCC TGGCCTGAAA CAGGTGTCTT CTATAAGAAA GACAGAGTTG TGTCCATTAT     600

GCCTCTCTCG CTGCTTCCTG GTAAAGGGAC CTAGGCATCC CTGGGTGACT GGAGTGCCTG     660

GTGACCACTT CCATCCACCC CCATTATCTG CTGCTAAGGT ACACATGAAG TATCTTAGTT     720

CCCAGAAAGA GAACCCCTGT TGAACAGTAA CAAGCCCCAG CATAGGGTGC TAATGATTTA     780

TCTGCTTTCA CATTTGAGCG TGCTTTCTTG GAAGTGATGG AGAATCTTCG GCCTGAAGAT     840

GTGGAGGCGC ATGCAGAGTC CTGAGCTCCC ACACAGGCAG TTAGGTGTAA CTGAGAAGGA     900

GCTGTGAGCA TATCTGGCTC TCCAGCTCCC ACAGCAAGCG GGTCCACCA GTATTGACAT      960

GGCTCTTGTC TGCATGATAA GCTGGACCAA CAAGGCCAGG GCTCTGCCCA CAAAGCTAAA    1020

CTAGTATGGG GACTTGGCAC TTGTCCCTGT CAGGGGAATG GTAAGCATTT TCGCACAGAC    1080

TAG                                                                  1083

(2) INFORMATION FOR SEQ ID NO:76:

(i) SEQUENCE CHARACTERISTICS:
        (A) LENGTH: 854 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: G255.seq (xi) SEQUENCE DESCRIPTION: SEQ ID NO:76:

CTCAGTTTGG GCTCTGGGCT AATCATCTGT CCTGTCCTAC TTGTCTTCCA CAAGGGACCG      60

ACTGGTCATG AAGGCCATGA AGGCTGTCTG CTGTGTGTCC CTGGAAATGT CTGTCGACAG     120

CCTCTCTAGG CAGAAGTGTT TCTTCTTGTG TACCAACCAA GACCTATAGG CCTCGCCTCA     180

TCTCCCAAGC TATACCTTAC CACAAAGCAG AACAAGGGTG GACTAAGAAC TGGCAGAGAT     240

TTATACTTGG CTTTCCAGAG GTCCCAGGTT TGTGGTAGGG GTTCATGAGG CTGGCTGCTA     300

TCTAGATGAG ATATGCAGAG TGAGCTCCTT TCCCTGAATG CTGGGCATCC CATCGGTAGT     360

ATGGGACAGG GTAAGCTCCT GGCCTGGCTG GCTCCAATGC TGCCTGAGTG AAGCTATGTA     420

ACCCTGGGAC ATCTCTCTTA GCATGCTGAT ATTTGGCTGC TTCTCTGATA ATGGGAGCAG     480

CATTCTCTGG TACGGGGTGC TGTGGAAGAC CTAGGGAATG GGACAACAGA TTAAAATGGG     540

CTTTGAAGAC CCTTGGAGAG GTGACCAGGG AGGCCCAACC TTCTATTTCC TGTGCTCAGG     600
```

-continued

```
CCTTGGGAGA GACAGAAACC ACGAGGGTCC AAGGTCCCCA ACCAGTGGGA CCCCGACACC    660

AGGAGGACAG GACTCTCAGA GTTCTGTGCC TACTCCTCAG TTTCTTTTGT GTCTGCTGCT    720

ATCAGGAGTC CCAATCTACA GGGCTCAATC AGGATGGGAT CCTTAGTGTG GCACCTGGGT    780

CAGAAAACCG CCCCTGCTAA GAGGCTCAGG ACAGGGCTAA CTGGGAGAAG AGGCCCCACC    840

TAAGTGTCTG CCAC                                                      854
```

(2) INFORMATION FOR SEQ ID NO:77:

(i) SEQUENCE CHARACTERISTICS:
        (A) LENGTH: 605 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: G306.seq (xi) SEQUENCE DESCRIPTION: SEQ ID NO:77:

```
CCCGCACTGG AACAGAAGCT TCGTGAGAAC AGGGACTTTG TCTTGTGTGT TCGCTCCTCT     60

CTTCCCAGGT CCTAGAACAG TGTCTCGTCC ATAACAAACA CTCAATGAAT ATTTAGGGAA    120

TGAATGTCTG CAAGATGCTG AGAATCTCTC ATAGAGTTTT CATATGTGAC CCCTCTTTGA    180

AATTGGGTAT TATCAAGTTA TTCATTTTAA TGATTCAACC TAATTCAGTA ATCAAGCAAA    240

TTGGCAGAGA CCTAAAATAT TTACCCGTTG TTGTGAGGAT GAAATAAGTA AACAAGTGTA    300

AGTTATTTAG AGCAGTGTCT GGTAACCACA GCCCTGTGTA AGAGTTTGCT GCTGTTGTTA    360

AGAAATGCTT GACTTCTTGA TATCTTAAAG TTTTTGCTGA CTCTGCTGCC TGTGTTGGGA    420

TCCCAAGCAG AAACTGTTTG TGGCCCAGCA GGTGTTGGCA CTGGGTGAGT GCTTCTGGCT    480

CTTGTCCCAC GACGGACATC CAGGTCTTCC AGCGGCCTGA GGATATAGGA GGGGCTTCAG    540

GCGGATGATT GTGGCCGTTG CTTATGTTTT TTCCTTGTTT GGCCTACAGG CACATGTCAC    600

CACAC                                                                605
```

(2) INFORMATION FOR SEQ ID NO:78:

(i) SEQUENCE CHARACTERISTICS:
        (A) LENGTH: 890 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: G256.seq (xi) SEQUENCE DESCRIPTION: SEQ ID NO:78:

```
GGGGCCAGTC ATCTTGAAGA AGTCTTCCAC ATGCCCTGT CACACTCATC CCTTTACCAA      60

AAGCCCCTAC CCATGGGGTG GGTCAGGCAG GCCCCAAGAC AGGCCCGTAT CAGGAGGACC    120

CCTCTTCTCT CAGGGGCTGC CCTCTGGGAT AACCACCCCC GCCCTTCTGG GTTTCCTGCT    180

TCCTATCTGG CTGCAGTTTC TCAGGTCCCT TGTGGATTTC CCCATGGTCT GTCCCCACTC    240
```

-continued

```
ACATCCCCTC TCTGCAAACC TTGCCTACTG GGCCTGCACC TGGCAAATCC ATGCTCAGCA    300

CAGACGGGGA TCAAGACCTC TCAATACAAC TGTCTCCTGC CAATCCCTGC CCCAGCAGCC    360

TGAGGCCCAG TCTGAAACCA GGGAGTTGCT CTCCTTTCTC CTCCCTTGAC CTCACCCCTC    420

AGACCATGCC AATTCTGCCT CCTAAACCTC CCAGGCCAGC CCCTCCCCCA GCTCCCAGTG    480

ACAGTGTCCT CAGGTACCTG AGCTCAGCTC TCGGTGCTAC CAGAGGGACT GCCAGGGGCT    540

GCAGCCGGGC CTCCTGCAGA GGCTGAGTCC CACACGCAGG GAACAGCCAT GCCACTGCTA    600

GCAGACCAGT AAGAGAATGG CCACCTGGGG CCTGAGCGCC CTCGGCCATC CACCAGAAAC    660

AAAGTGTCAA GGAGAAGCTG CCCGAAGCCC ATGGGACAAA CCACTGGGGA CTGGAACACC    720

AGTAATTCTG TATTGGGAAG CGGCACCAAG AGATGTGCTT CTCAGAGCCT GAGGCTGAAC    780

GTGGATGTTT AGCAGCGTGA CCGGCTACCA GACAAACTCT CATCTGTTCC AGTGGCCTCC    840

TGGCCACCCA CCAGGACCAA GCAGGGCGGG CAGCAGAGGG CCAGGGTAGT              890
```

(2) INFORMATION FOR SEQ ID NO:79:

(i) SEQUENCE CHARACTERISTICS:
        (A) LENGTH: 1370 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: G181.seq (xi) SEQUENCE DESCRIPTION: SEQ ID NO:79:

```
GCAGAGGAGC CATGTCCTGC TGCTTCTGCA AAAAACTCAG AGTGGGGTGG GGAGCATGCT     60

CATTTGTATC TCGAGTTTTA AACTGGTTCC TAGGGATGTG TGAGAATAAA CTAGACTCTG    120

AACAACTGCT TTGTTACCAG TGTCTCAATT TGACTTGGGA CTTAGTGACC ATTTTAAGGG    180

AGACTGGTGC GCCACAAATC CTGGGTGGCT TGATCCTGCC ACGTGGATGC TGTCTGGGTG    240

AGCTTGTTCT CACACTGCCC TCCTGCCACC CCCATTTCCA GAAAGGTGAT GATAACCCTA    300

GCAATCTTGG AAAATCCACA GGAACTGCTA CCAGGTACCA GGAGCCGTTC TGAGCATTTT    360

ACCTATGCTA TCTAACTTAT TCCTCACCCC AACCAAGAGT ATGTTTTCTC CGTTTCATGG    420

GAAACTGAAG TTCGGCCTGG TTGAGCAACT GTCTAAGCTG ATAGTGGCCC AGCTGGGGCT    480

TGAATTCAGG TCCCTGTGGT CTGGAGCATG CTAATCCTGT GGCATGTCTC CCCCTAGTGG    540

TCCTTCCAGA AACTGCAGCC GCCGCCCCTG CTCCTCCCAG GGCCAACATC AGGGATCAAC    600

ATCCCCTGAC CCCCTCAAGG CAGCAGGTTC TGCTGACACA AGCCACCCAA TTCTTCATTC    660

CATTCCTTTA AAACCCTCCA AGCCTGGAGT CTCCACCCCT GCCTAAGCCC CCAGCCTCTC    720

CTGCCTGATG ATTTAGCAGC CACCCTGTAG GCCTCCCGGC CAGCCCTGGA ACCCACACCC    780

TGACGATCTG TGCTCTACTG GGGAGCCAGA TGGAGTTTTA GAAAATGCAA ATCTGACCAT    840

GTGGATCTAT ACTGAATCCC CCAGTCCTCG GGTCTTCTG GACCTTGTCC ATATCCTTAG    900

GACAACGTAT AAGGCTCACC TCCATCTGTT GCTTCTGTTT CCCCCATGGC TACCACCCTA    960

ATCAATGCTC CAGCCAACAG GAGTGCTGGG ACTTCCTAGA CAGCCTTCCA TGAAGCCTCT   1020

CTTCATGCCC TGGAGCTTCT ATCCACATTG TCACCTCAGT CTGGCATGCC CTTACTTGGC   1080
```

```
TTGATGAGTT CCTATTCCAT GGACCAACTC AAACTCTGCC CACCTCTGGA CTGTCCACAC      1140

CATCCCAGGA TGGGGCCCTC CTCCGAAATA GGTGGGTACA CAGGGACCCA CTGGAGGGAC      1200

AGCCACTGTG GCACGGAGGT GGTGCAGACC AGCCTGGAGG CAGAAGGCAG GAGGCTGGGA      1260

CATCCCGAGT GTGGCTTCAG TCTACCACCT GGCCCTTTAG CCCTGAGTGC CCCCCTCTAA      1320

CTCCCCTGCA CACCACCCTG TGGCCCTACT CAGTCTGCCA GTGGAAGGAG                 1370

(2) INFORMATION FOR SEQ ID NO:80:

(i) SEQUENCE CHARACTERISTICS:
         (A) LENGTH: 695 base pairs
         (B) TYPE: nucleic acid
         (C) STRANDEDNESS: double
         (D) TOPOLOGY: linear (ii) MOLECULE TYPE: cDNA to mRNA (iii) HYPOTHETICAL: NO (iv) ANTI-SENSE: NO (vi) ORIGINAL SOURCE:
         (C) INDIVIDUAL ISOLATE: G257.seq (xi) SEQUENCE DESCRIPTION: SEQ ID NO:80:

GGACATGCAG CGAGCTGTGC CTGCCCAAAC AGGGCCTCAG GGAAAGTCTG AGGGACCCGT       60

GAGGGATCCA GAAGAGTCTT GGAGGAGGCT CATTCCAGAA CCACTCGTCC TGCTGAGAGC      120

AGAAAGCCCA CATCTGCCAC CTCAATTCTG ACCCATCAGT TCCAGGGGGA TGCAGGTGCG      180

CGAGCCGGGC AAGGGCCTGG GACTTCCACC TGGCATCTTG ACCCAGACTC TAGCTCCAGA      240

CATAGAGGGC AGGAACGGAT GCCTGCAGGA CTTCAGAAAT TAAACAGGCT TCTGGTCTCA      300

TGATTTCTCC TGCTTTTGAT TTTTAATGCA CCTCCCGATG GCTCTTCCCA AGAGGGCACA      360

CATAGGCTGT GGCCCCTCTG GGTGCCTGAT GATCCTCCCA GCCAGAGATG AGGCTCAGAG      420

CAGAGACTCA GGAGCAGGGG ATGCATTTCT GGCCCTAGAG GGAGTACACC AGGCGAGTAG      480

TAGACACAGG TCAGGGAGGG CACTGTGGTG GGAAGGCCTG GCACACCCAT TGGGCGTTTG      540

TGTCCACAAG GACCCTCTGC CTGAGTGATG TGCATGGTGG AGTTGCCAGA TCCTGAGGGA      600

AAAAGGAAG CCCCAAGAAC AAAGAAGCAA ACAAGGAGGT CTCATTGTCC TTGGCCATCC       660

TCAAAAGTTG ACACCCCGCC ACTACTTTCT GCCTG                                 695

(2) INFORMATION FOR SEQ ID NO:81:

(i) SEQUENCE CHARACTERISTICS:
         (A) LENGTH: 700 base pairs
         (B) TYPE: nucleic acid
         (C) STRANDEDNESS: double
         (D) TOPOLOGY: linear (ii) MOLECULE TYPE: cDNA to mRNA (iii) HYPOTHETICAL: NO (iv) ANTI-SENSE: NO (vi) ORIGINAL SOURCE:
         (C) INDIVIDUAL ISOLATE: E2.seq (xi) SEQUENCE DESCRIPTION: SEQ ID NO:81:

CAAACCCACT CCACCTTACT ACCAGACAAC CTTAGCCAAA CCATTTACCC AAATAAAGTA       60

TAGGCGATAG AAATTGAAAC CTGGCGCAAT AGATATAGTA CCGCAAGGGA AAGATGAAAA      120

ATTATAACCA CGCATAATAT AGCAAGGACT AACCCCTATA CCTTCTGCAT AATGAATTAA      180
```

```
CTAGAAATAA CTTTGCAAGG AGAACCAAAG CTAAGACCCC CGAAACCAGA CGAGCTACCT        240

AAGGAACAGC TAAAAGAGCA CACCCGTCTA TGTAGCAAAA TAGTGGGAAG ATTTATAGGT        300

AGAGGCGACA AACCTACCGA GCCTGGTGAT AGCTGGTTGG CCAAGATTAG GAATCTTAGT       360

TCAACTTTAA AATTTGCCCA CAGGAACCCT CTAAATCCCC TTGGTAAATT TAACTGTTAG       420

TCCAAAGAGG AACAGCTCTT TGGACACTAG GGAAAAACCT TGTAGAGAGA GTAAAAAATT      480

TAACACCCAT AGTAGGCCTA AAAGCAGCCA CCAATTAAGA AAGCGTTCAA GCTCNACACC       540

CGCTACCTAA AAAATCCCCA CATATNTGTG GACTCCTCAC ACCCTANTGG GCCAATCTAT       600

CACCCTATAG AAGAACTAAT GTTAGTATAG GTAACATGAA AACATTCTCC TCCGCATAAG      660

CCTGCGTCAG ATTAAAACAC TGAACTGACA ATTAACAGCC                            700
```

(2) INFORMATION FOR SEQ ID NO:82:

(i) SEQUENCE CHARACTERISTICS:
        (A) LENGTH: 254 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: E9f.seq (xi) SEQUENCE DESCRIPTION: SEQ ID NO:82:

```
CCCTGAGTTA AGGATCAGTT GGNTGTGGTG TTAGCTAAGA AGGCTGCCAC CCATCATTCA       60

CATAATGAAG TGACTCAGNG GACTGTGCTG ATGGTTCTGT CCCAGGCACA GAAGACTAGG      120

AGGCTATGGA GGGAGGACAG ACTGAATTAT GTTTCANGTG CAATGGGGGA GGAGAGGCAG      180

GCAGCAAGTT CCTGGGCCCA AAGTGGCACG GGTGCAGAGT GGGAAGGTGG CAAACCCCTC      240

TGTGCTGGTG ATAG                                                       254
```

(2) INFORMATION FOR SEQ ID NO:83:

(i) SEQUENCE CHARACTERISTICS:
        (A) LENGTH: 391 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: E9r.seq (xi) SEQUENCE DESCRIPTION: SEQ ID NO:83:

```
TGCANCTGTG CCTCCTGTCG GTGTATTTGC ATNTGGTGCT GCCTATGTAG GGTTGCTATT        60

CCCTCCTCCT CACTCTGTCC GGAGAACCCC CATCCATCCT TCGAAGTCCA GCTTGGTAGN      120

TGATCGATAA CACACATGCC CAGAGAGGAG CTTCTTCTGT CCCTGGAATA CAGNCTCTCC      180

TNGTACCATA TCTGTCGCCC AAGTGCAAGT GGNTCTGATT GGATGTGTCC CAGCTTCTCT     240

TGCAGGTCTT AGGTGGGCTT GGTCCTTGAA AGCACTGGCC AATCAGAACT TGCCACTCGA     300
```

-continued

```
AAACAGTCGA GAGCTGCCTG TGGGGTTGGA GTTCGGATGC TNGATTTCTG GTTCTCACAG      360

ATGTNAANAA TCCTTAGACC TGCTGTTCCA A                                     391
```

(2) INFORMATION FOR SEQ ID NO:84:

(i) SEQUENCE CHARACTERISTICS:
        (A) LENGTH: 302 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: G123con.seq (xi) SEQUENCE DESCRIPTION: SEQ ID NO:84:

```
CAAGCATGAT ACCAGGGCCA TGGCAGGTGA GCTATCCCCA GGTTCAGTGG AGAGAAGCTA       60

CTCCTGGCCT TTCTCCCACC AGTCAGAGAA GCAGCTGCAT TATATGGCTA AAGGGCTGAC      120

CTCAGCTTTG TTCCAGCCCT TGGGGCAGCT TGACCTTAGG CCATCACTTG GCCCACACTC      180

TATACTCTTG GGGAGCCTTG AACTGCCAGG CCACTGGCTG GCATGGTTCT GAACCTGAAC      240

CTCTGAGATG TCTGGGTGCT CTCAGGGTAA GAGGCAAAGA GAGGCAGCCT ACCACCTCCC      300

AC                                                                     302
```

(2) INFORMATION FOR SEQ ID NO:85:

(i) SEQUENCE CHARACTERISTICS:
        (A) LENGTH: 2995 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: A116con.seq (xi) SEQUENCE DESCRIPTION: SEQ ID NO:85:

```
CCGCAAATGT CTGTAAACTT GGCCCAACAT GAGAAATCTA GCTGGTGTGG CTGAGCACCA       60

CTTTTGTCAG TTTACCCCAG TGGAAAGTGG TCCTTGATGA CAGTTATCTC ATCACAACCC      120

CAGCAAAACA GATCTTTCAA CAACCTCCTA GCTCCCTCAA CCTAGAACTT CCACCATTAG      180

TGCTTATACT GAAACTCTTG AGAATGACCC ACAGAAGCAC TGTCAGGTCC TTAGAATGAT      240

CTAATTATTA AGCACAAACT TGGTTCAGAT CTTACTAATA CTGCTCCGTT TCAGGCACTG      300

TTTGGCTAAT GACTCGGTAG TGTCAGCTGC CATCACCTTT AGGTGAGCTG TCAGACCTTA      360

TTTAGTTTCT TTTCCTAGGA AAAGGCTGAA GTCTTGGTAG GATGTGATGG GACAGCTCTC      420

CATCCTGAAA GGTCTGGCTC TATCCCACAC TACTCCAGGC TTGGTCCCTA GGACCCAGCT      480

CCATTGTGAT GGGGGCCAGG GGAGAGTTTT GAGGTCCCTC CCTGGAGATT CCAAGCAATT      540

GCTACCAATC ATTTAGGACT CCTGGGATCA GAGGGGATGG GGAAATTGAG GACTCCATCT      600

TGGTTGTGGA GATTGGAAGC TGATGGACAT AATTCCTCTC TCTTTTTGGT AATTTACAAG      660

CAATTAACTT TGCTTTTAGA ACTTGAGAGA TTTCCACAGC TGCCTAAGAC TTCACATACT      720
```

```
CACTGCCTAC CCTCCATCAG GGATTAGATT GAAGGGCAGG AGAAAAAGAA GTCAGAGCTG      780
CTGCTTGTTC TGGGTGGTAT CACTTTCCTC CCGTCAGTCC ACTCTACCTT GCTCTGCACC      840
ACCTGCCATC ACCCACTAGG AGAACCCAGA TGGAAGCCAC AGGTGGCTAG CCACCTCAAT      900
CCAAATCTTA AAAGGGCTG GTCCCTGAAG GAGCTGGAAA AGTCCATCCT GTCTATTCCT       960
CTGTTCCCAG GTGAAGCTAT TCTTGAGAAA TCCAAGTGGA GCTTCCAAGT AGAACTTCTT     1020
TTTTTTTTTT TTTTTGAGAC AGAGTCTCGC TCTGTTGCCC AGGCTAGAGT GCAGTGGCGT     1080
GATCTCAGCT CACTGCAACC TCCACCTCCT GGGTTCAAGT GATTGGCCTG CCTCAGCCTC     1140
CCTAGTAGCT GGAATTACAG GCATGCACCA CCACGCCTGG TTAGTTTTTT TTTAGTAGAG     1200
ACAGGGTTTC ACCATGTTGC CCAGCCTGGT TTTGAACTCC TGAACTCAGG CAATCCACCT     1260
GCCTCGGCCT CCCAAAGTGC CAAGATTACA AGTGTGAGCC ACCGCGCTCG GCCCAAGGGG     1320
AGCTTCTGAC AAGCAGGGCC TGGGATAGGG GCCTGTCCAG GCATCCACAT ATAGAATATT     1380
TACCCAGCAG GAGTCCCCCT GCCACTCACA CAGCATCTCC AAGATCAGGG ACCAGTACTT     1440
CCTGAGCTTG ACAGAGAATG AATGTGTCAG ACTGACCTCT GCCCATTTTG TAGTTTTCTC     1500
ATCATTTTCT CACTCAGTCT TCCCTTTTCA AGGGCCCACA CTCTTCCCGA GGGCTGGGCC     1560
TAGTGAGCGG GGTCACAGTA CATATGGTTT CTGGGACTGA GAAGGTGGAA GATGTGTCCA     1620
TAGAGCTTTT GTTTCCTAAG CAACGTATTA CTGCCATGAT TCCATTCCCT AGATGATGCT     1680
GGTGATGCAA GCTGGCTTCT CTTGGCCAGC CTACCCTACT GCTGGGTAGT GTTTATGCCC     1740
CATGGCCAGA CACTGAAGAG GGAGACAGGA AAAGCACATA TCCACACCTT CCACCCTCAG     1800
ACATTCCTGT AACTTGAGCT TATCTAAGGG GGCATTGTCA TATGTCAGGG GTTCCCAAAC     1860
TACGGTCTTC AGAAACACTG TTTACCCTCC ATAGAGGTTG TGTGCATCAG CCCAGGCAGA     1920
ATCCTGCTTC ATGAAGGTGT TTTCCTAATG CATGTGTGCA TGGACCTGTC TCATGCTACA     1980
CTGCAGGGCT GGTATTCAGC ACCAATAGTT ATTGTTGGCT GCTAAAATAG CAAACTAGCC     2040
AAAATGGCAG GTAAATAACC CCAAGCCCCT ATCGCCAGTG TCCTCCCACT ACTCCAAACC     2100
CCTCTCCCTC AGACCTGCCC CCAGTCCAGT ATCTACCTGC ACTGTTCAAT ATGGTAACCA     2160
CTGACCACAT GTGACTATTT ACATACAGTT TATTAAATGC AATTAAAAGT TCAATTCCTT     2220
ATTGCACTGG CCACATCTCA AGTGCTTAGC TGGCACATGT GGCTAGTGCC AGTGCCTACT     2280
GTATTGAGCG GTACAGACAG ACATTTCATC ACTCTAGAAA CTGGATGGCA AGTGCTACTC     2340
AGCACAGCAG CCGTGAGGAC CTTTCTTGGG CTGCTGACTG TTCTGTCTGT GACTGTGTCA     2400
TGTCAACTGA CTTTTTGGAG CAGCATCTGT GTGTTAGCAG GACACATCAC CTATGGCACA     2460
TGCCTCAAAA CTTAACACTC CTTGGGCCCC AGGAGCCCAG AATCAACTGA CAGCCCTGGT     2520
GATTGTCAAG GACAGGTGAC TATGTTTATA TAAGCATGTT CCTATGACAG GAATGTCCCC     2580
TCCTTCTGCC ATTGTCTATG TGAGCATAAA CAAAAGGATT TTTTTTTTT GAGACAAAGT      2640
CTCGCTCTTG TCACCCAGGC TGGCGTGCAG TGGCACAGTC TCAGCTCACT GCAACCTTCA     2700
TCTCCCGGGT TCAAGTGATT CTTGTGCTTC AGCCTCCACA GTAGCCGGGA TTACAGGCGC     2760
CCGCCACCAG GCCCGGCTAA TTTTTTTTTT TGAGACGGAG TCTCGCACTG TCGCCCAGGC     2820
TGGAGTGCAG CGGTGCAATC TCGGCTCGCT GCAGCTCTGC CTCCGGNGTT CATGCCATCT     2880
CCTGCCTCAG CCTCCCGAGT AGCTTGGGAC TACAGGCACC CGCCACTAGG CCCGGATTAT     2940
TTTTTTATTT AGGAGGAACG GGTTCACGGT AGCCAGGATG CTTGATCTCG ACCGG          2995
```

(2) INFORMATION FOR SEQ ID NO:86:

(i) SEQUENCE CHARACTERISTICS:
        (A) LENGTH: 1870 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: A25con.seq (xi) SEQUENCE DESCRIPTION: SEQ ID NO:86:

| | | | | | |
|---|---|---|---|---|---|
| GTCATCCTTC | AACAAACACT | TAAAAAATGT | TTGAAAACCC | CATCAATTCA | GTCAGACTCT | 60 |
| TTGGGTGGGA | GCAAGATCCA | GGCATCAGTA | TTTTTTAATA | TCCCAGATGA | TGGTAATATG | 120 |
| CAGCCAGGAT | TTAAAGTCAC | TGGTTTAATA | TCTTGGGAAA | AGCAGATCCA | CTCAAGACCT | 180 |
| CACAGGGTCC | TGACAAAGGC | CACTTTCAGC | TCAGTGGAGT | GGGACACTGG | GGTGGGAAGA | 240 |
| TGTCCATTTT | TTGGATGTGG | GTCAGTCTCT | TGCACAGGCA | GAGGTATTGC | AGCATGCTGT | 300 |
| TGTAATGTGT | ATCTTCCTTG | GCAGTGTCTG | TTGAAAGCTG | GTTGCATCAG | TTTGTAATGG | 360 |
| GGTGTTATGG | CAACAAGGTG | GGCCCAGCCC | CCCCCAGGAA | GTGGATCACT | GAGCACAGCT | 420 |
| TCTACAGGGC | CATTTGTAGA | GAGGTGGCAG | ATGGGCTTCC | CAGGGGCTGC | CACCCAGGGC | 480 |
| AGAGCCAGTG | CTGAGGCTCT | GACAACCTCG | GCAGGGTGGG | GGAGAAGGCC | AGACTCAGGG | 540 |
| TGTTTATGTT | TGTGGGTAAT | GACAGTCAGC | TCTGGGCTCC | AGATGATGCC | TACTCCCTGG | 600 |
| CCTCTGTGTT | CAGATTAGGA | ACTTGCAACA | TCTTGCTGAG | GACCATGTCA | GGCTCAGCTC | 660 |
| TAAGTGCTGT | GGCTGAGAAT | TTTCCTTCCT | CTCTGTGTGG | TTAGTGGCAG | CCTCCCTAGC | 720 |
| AATGGCTGAC | CTCTAGCATA | CTCTGTCAAA | CTACAGGCAG | CTGGGACAAG | ACAGGACATG | 780 |
| GGGCTCACAG | ACAGGTATTC | CACAACCTGG | GCCCTGTCAA | CCCTCCCAGA | AATGCATGGG | 840 |
| CCATGAACCT | CCTGCTGTGG | GAGGGGCAGT | GCAGAGAAGT | CTCAATAAGC | TTCTCTTGGC | 900 |
| CCTCTGGGAT | CTCCACCATC | CACAGTGTGT | AGGGCTGAGC | TGCAGGCTGG | GTCTTCAGGT | 960 |
| GGTGTCCCTG | CACATCTGCT | TTGCAGCGTG | GCGTCTATAG | AGCAAGAGTG | AACGGGAAGG | 1020 |
| GGCCTCGGGC | CTCCTGTAGC | TCTGCTGGGC | AGGGACGCTG | CGGGGCCTCA | GCTGGGCTTC | 1080 |
| CTTGGCTAAA | GGGCACAGAG | TGGCGTAGGC | TGCAAGAGGA | CAAGCTAAGC | TGATGAAGGC | 1140 |
| TCTATCACTC | AAGGGTAGCC | ATGTAAAAAA | AAATCCCTAC | AGGTAAAAGA | AGCATGAATG | 1200 |
| AGACAGGCGG | GGCATAACAA | TGTCTCCCCA | CTGAAGCTGC | AACTCTCTGC | TTCACTGGCT | 1260 |
| TCAGCCTCCT | CTCTGTGAAA | TGGGGCAAT | GTCCCCTAGG | CCTCTTCCTC | CCTGTCCAGT | 1320 |
| TAGAGCTGAG | GGTCTACAGG | CCAGAGGGAG | GCCTGGCTCT | CAGGGCCTTG | TTCTCTGTNT | 1380 |
| TNGCCTCTNC | GCTGGCNACC | CCAGCCCCAN | TTTCCACGTC | AACCTCCCTT | GTTTTTTTAT | 1440 |
| TATACCNCAA | CAGCAGCTCT | TGGCAGCCCA | GTTGGACTAC | CCCCTTCCTG | TTGNCTTCCT | 1500 |
| TAGCAAAGCA | TTTTATGGAA | TGCTTCCTTT | TCATGCTTCA | GGAAACCGGT | GGCCGGGAGG | 1560 |
| AGTTCTTGAT | TTCATTTTCT | TCCCTAGAGA | TATGTGTGCT | TCGGAATACA | CAAATTAAAC | 1620 |
| AAAAGCGAGG | GCTGACTGGG | ACCAGGAGAG | TGAGTGATCC | TGGCTTCCCT | TGATTTACAT | 1680 |
| GCTTATTTTC | CTTCTCAAAT | CACTCCAGTA | AGTACAGAAG | TCACTAATCT | ATTGCCTTCT | 1740 |
| ATTATCTGCA | TTATAGTTAA | AAACATCGAC | ATGAACAAAC | AAAAGCCCTT | GCGTAGCCTA | 1800 |
| GAGAAGTCAC | AAAGCTCACA | CCCAGACTCT | CGCCTAAGAG | AGTCTCTCAG | GGCTCACTCA | 1860 |

```
GGGACTATTT                                                                    1870

(2) INFORMATION FOR SEQ ID NO:87:

(i) SEQUENCE CHARACTERISTICS:
        (A) LENGTH: 806 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
         (C) INDIVIDUAL ISOLATE: A46.seq (xi) SEQUENCE DESCRIPTION: SEQ ID NO:87:

CTACTACTAC TAACTCGAGA ATTCTGGATC CTCCAAACAC ACTCCACCTT ACTACCAGAC    60

AACCTTAGCC AAACCATTTA CCCAAATAAA GTATAGGCGA TAGAAATTGA AACCTGGCGC   120

AATAGATATA GTACCGCAAG GGAAAGATGA AAAATTATAA CCAAGCATAA TATAGCGAGG   180

ACTAACCCCT ATACCTTCTG CATAATGAAT TAACTAGAAA TAACTTTGCA AGGAGAGCCA   240

AAGCTAAGAC CCCCGAAACC AGACGAGCTA CCTAAGAACA GCTAAAAGAG CACACCCGTC   300

TATGTAGCAA AATAGTGGGA AGATTTATTG GTAGAGGCGA CAAACCTACC GAGCCTGGTG   360

ATAGCTGGTT GTCCAAGATA GAATCTTAGG TCACTTTAAT TTGCCACAGA ACCCTCTAAA   420

TCCCCTTGTA AATTTTCTGT TAGCCCAAAG AGGAACAGCT CTTTGGACAC TAGGNNNNNA   480

CCTTGTAGAG AGAGTGAGAG AATTTAACAC CCATAGTAGC CCTAAAAGCA GCCACCAATT   540

AAGAAAGCGT TCAAGCTCAA CACCCACTAC CTAAAAAATC CCAAACATAT AGCTGAACTC   600

CTCACACCCA ATTGGGCCAA TCTATCACCC TATAGAAGAG CTAATGTTAG TATAAGTAAC   660

ATGAAAACAT TCTCCTCCGC ATAAGCCTGC GTCAGATTAA AACACTGAAC TGACNATTAA   720

CAGCCCAATA TCTACAATCA ACCAACAAGT CATTATTACC CTCACTCTCA ACGAGGATCC   780

AGAATTCTCG AGTTAGTAGT AGTAGT                                        806

(2) INFORMATION FOR SEQ ID NO:88:

(i) SEQUENCE CHARACTERISTICS:
        (A) LENGTH: 639 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
         (C) INDIVIDUAL ISOLATE: A66.seq (xi) SEQUENCE DESCRIPTION: SEQ ID NO:88:

CTGAAGACTG TTCCCAGTGG TCTTAGATAC AGAGTGGTGG CCCTTGGTCC TGTCAGAGTA    60

GGTTTAAAGA CCACACAGGT AGATTTCTCC CAGAAACAAC ACCACTTAGA ATTTTCCTTC   120

AGGGAGCATA GCACAGGGGA GATGTCCACA CACAGTCATA CCTGTGTTTG GAATCCCAGC   180

TCTGCCTTTT TGCTTGTGGG TGGTCGAGTT GGGAGTGTGC TTGAGAAATT ATTCAGCCTC   240
```

| TTCAACTCTC AGTTTCTACC TCTCCTTTCC AGGCTGAGCT GAACATCACA GAGGGGAATA | 300 |
| TCTGTGATTT TCTTGAGAAA CTTCACAGCG AAAGCTGCTG GCTCTGCCCT TGGTAGCCAT | 360 |
| TTTTATGGTC TGGAGGGACA GTGGCTTCTT CCTAGAGCCA CTTTGCAGTG TTCCCTTGAG | 420 |
| GCCAGCTGTC CATCCTCGAG AGCAGTTAGG AGGTCCATGT TGAGAGTGTG CTCAGTCCTT | 480 |
| AGTTGGAAAC CTGGAAACGC AGGCCATGAG GGTGGTGTCC CACTGGCATA TGGCAGGTGG | 540 |
| GGCCTTCTGC CACCCTGGCT GTGTGTGTGG CGTCCAGTGC GAGTGGTAGC CAGACATCAT | 600 |
| GCCCACCTGC CCTCGAGCTG CTTGCCTGCA GCTGGCTCC | 639 |

(2) INFORMATION FOR SEQ ID NO:89:

(i) SEQUENCE CHARACTERISTICS:
        (A) LENGTH: 509 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: A42.seq (xi) SEQUENCE DESCRIPTION: SEQ ID NO:89:

| CTACTACTAC TAACTCGAGA ATTCNGGATC CTCCCCGAAA CCAGACGAGC TACCTAAGAA | 60 |
| CAGCTAAAAG AGCACACCCG TCTATGTAGC AAAGTAGTGG GAAGATTTAT AGGTAGAGGC | 120 |
| GACAAACCTA CCGAGCCTGG TGATAGCTGG CTGCCCAAGA TAGAATCTTA GNNCAACTTT | 180 |
| AAATTTGCCC ACAGAACCCT CTAAATCCCC TTGTAAATTT ANCTGTTAGT CCAAAGAGGA | 240 |
| ACAGCTCTTT GGACACTAGG AAAAAACCTT GTAGAGAGAG TAAAANATTT AACACCCATA | 300 |
| GTAGGCCTAA AAGCAGCCAC CAATTAAGAA AGCGTTCAAG CTCAACACCC ACTACCTAAA | 360 |
| AAATCCCAAA CATATAACTG AACTCCTCAC ACCCAATTGG ACCAATCTAT CACCCTATAG | 420 |
| GAGAACTAAT GTTAGTATAA GTAACATGAA AACATTCTCC TCCGCATAAC CCTGCGAGGA | 480 |
| TCCAGAATTC TCGAGTTAGT AGTAGTAGT | 509 |

(2) INFORMATION FOR SEQ ID NO:90:

(i) SEQUENCE CHARACTERISTICS:
        (A) LENGTH: 1834 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: A76con.seq (xi) SEQUENCE DESCRIPTION: SEQ ID NO:90:

| GGCAGCCAGC GCAGGGGCTT CTGCTGAGGG GGCAGGCGGA GCTTGAGGAA ACCNCAGATA | 60 |
| AGTTTTTTTC TCTTTGAAAG ATAGAGATTA ATACAACTAC TTAAAAAATA TAGTCAATAG | 120 |
| GTTACTAAGA TATTGCTTAG CGTTAAGTTT TTAACGTAAT TTTAATAGCT TAAGATTTTA | 180 |
| AGAGAAAATA TGAAGACTTA GAAGAGTAGC ATGAGGAAGG AAAAGATAAA AGGGTTTCTA | 240 |

-continued

```
AAACATGACG GAGGTTTAGA TGAAGCTTCT TCATGGAGTA AAAATGTATT TAAAAGAAAA      300

TTGAGAGAAA GGACTACAGA GCCCCGAATT AATACCCAAT AGAAGGGCAA TGCTTTTAGA      360

TTAAAATGAG GGGTGACTTA AACAGCTTAA AGTTTAGTTT AAAAGTTGTA GGGTGATTCA      420

CATAATTTGN AGGCGATCCT TTTCAAAAGA GATTAAACCG AAGGTGATTA AAAGACCTTG      480

TAATCCATGA CCCAGGGAGA ATTCCGTCAT TTAAACCCTA GTTAACGCAT TNTCTAAACC      540

CAGGCGAANC TGGAAAGATT AATTGGGAGC TGGTAGGATG AAACAATTTG GAGAAGATAG      600

AAGTTTGAAG TGGCAAACTG GAAGACAGAA GTACGGGAAG GCGAAGAAAA GAATAGAGAA      660

GATAGGGAAA TTAGAAGATA AAAACATACT TTTAGAAGAA AAAAGATAAA TTTAAACCTG      720

AAAAGTAGGA AGCAGAAGAA AAAAGACAAG CTAGGAAACA AAAAGCTAAG GGCAAAATGT      780

ACAAACTTAG AAGAAAATTG GAAGATAGAA ACAAGATAGA AAATGAAAAT ATTGTCAAGA      840

GTTTCAGATA GAAAATGAAA AACAAGCTAA GACAAGTATT GGAGAAGTAT AGAAGATAGA      900

AAAATATAAA GCCAAAAATT GGATAAAATA GCACTGAAAA AATGAGGAAA TTATTGGTAA      960

CCAATTTATT TTAAAAGCCC ATCAATTTAA TTTCTGGTGG TGCAGAAGTT AGAAGGTAAA     1020

GCTTGAGAAG ATGAGGGTGT TTACGTAGAC CAGAACCAAT TTAGAAGAAT ACTTGAAGCT     1080

AGAAGGGAA GTTGGGTTAA AAATCACATC AAAAAGCTAC TAAAAGGACT GGTGTAATTT     1140

AAAAAAACTA AGCAGAAGGC TTTTGGAAGA GTTAGAAGAA TTTGGAGGCC TTAAATATAG     1200

TAGCTTAGTT TGAAAATGTG AAGGACTTTC GTACCGGAAG TAATTCAAGA TCAAGAGTAA     1260

TTACCAACTT AATGTTTTTG CATTGGACTT TGAGTTAAGA TTATTTTTTA AATCCTGAGG     1320

ACTAGCATTA ATTGACAGCT GACCCAGGTG CTACACAGAA GTGGATTCAG TGAATCTAGG     1380

AAGACAGCAG CAGACAGGAT TCCAGGAACC AGTGTTTGAT GAAGCTAGGA CTGAGGAGCA     1440

AGCGAGCAAG CAGCAGTTCG TGGTGAAGGT AGGAAAAGAG TCCAGGAGCC AGTACGATTT     1500

GGTGAAGGAA GCTAGGAAGA AGGAAGGAGC GCTAACGATT TGGTGGTGAA GCTAGGAAAA     1560

AGGATTCCAG GAAGGAGCGA GTGCAATTTG GTGATGAAGG TAGCAGGCGG CTTGGCTTGG     1620

CAACCACACG GAGGAGGCGA GCAGCCGTTG TGCGTAGAGG ATCCAAGGCC ACCATCCCAT     1680

TGTCCCAAGG CCACAGGGAA AGCGAGTGGN TGGTAAANAT CCGTGAGGTC GGCAATATGT     1740

TGTTTTTCTG GAACTTACTT ATGGTAACCT TTTATTTATT TTCTAATATA ATGGGGGAGT     1800

TTCGTACTGA GGTGTAAAGG GATTTATATG GGGG                                1834
```

(2) INFORMATION FOR SEQ ID NO:91:

(i) SEQUENCE CHARACTERISTICS:
        (A) LENGTH: 1666 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: E105con.seq (xi) SEQUENCE DESCRIPTION: SEQ ID NO:91:

```
CTACTACTAC TAACTCGAGA ATTCTGGATC CTCTGTAGCT TTTTTTTTTT ACAGACTNCA       60

CAGAGGAATG CAGTTGTCTT GACTTCAGGT CTGTCTGTTC TGTTGGCAAN TAAATGCAGA      120
```

-continued

```
ACTGTTCTNA TCCCGCTGCT ATTAGAATGC ATTGTGAAAC GACTGGAGTA TGATTAAAAG      180

TTGTGTTCCC CAATGCTTGG AGTAGTGATT GTTGAAGGAA AAAATCCAGC TGAGTGATAA      240

AGGCTGAGTG TCGAGGAAAT TTCTGCAGTT TTAAGCAGTC GTATTTGTGA TTGAAGCTGA      300

GTACATTTTG CTGGTGTATT TTAAGGTAAA ACGCTTTTTG TTCATTTCTG GTGGTGAGAG      360

GGGACTTGAA GCCTTAAGTC TTTTCCAGAT GCAACCTTAA AATCAGTGAC AAGAACAATT      420

CCAACCAAGC AACAGTCTTC AAGAAATTAA ACTGGCAAGT GGAATGTTTA ACAGTTCAGT      480

GTCCTTTAGT GCATTGTTTA TGTGTGGGTT TCCTCTCTCC CCTCCCTTGG TCTTAATTCC      540

TTACATGCAG GAACACTCAG CAGACACACG TATGCGAAGG GCCAGAGAAG CCAGACCCAG      600

TAAGAAAAAA TAGCCTATTT ACTTAAATA AACCAAACAT TCCATTTTAA ATGTGGGGAT       660

TGGGAACCAC TAGTTCTTTC AGATGGTATT CTTCAGACTA TAGAAGGAGC TTCCAGTTGA      720

ATTCACCAGT GGCCAAAATG AGGAAAACAG GTGAACAAGC TTTTTCTGTA TTTACATACA      780

AAGTCAGATC AGTTATGGGG AGGATCCAGA ATTCTCGAGT TAGTAGTAGT AGTCTACTAC      840

TACTAACTCG AGAATTCTGG ATCCTCTGTA GCTTTTTTTT TTTACAGACT NCACAGAGGA      900

ATGCAGTTGT CTTGACTTCA GGTCTGTCTG TTCTGTTGGC AANTAAATGC AGAACTGTTC      960

TNATCCCGCT GCTATTAGAA TGCATTGTGA AACGACTGGA GTATGATTAA AAGTTGTGTT     1020

CCCCAATGCT TGGAGTAGTG ATTGTTGAAG GAAAAAATCC AGCTGAGTGA TAAAGGCTGA     1080

GTGTCGAGGA AATTTCTGCA GTTTTAAGCA GTCGTATTTG TGATTGAAGC TGAGTACATT     1140

TTGCTGGTGT ATTTTAAGGT AAAACGCTTT TTGTTCATTT CTGGTGGTGA GAGGGGACTT     1200

GAAGCCTTAA GTCTTTTCCA GATGCAACCT TAAAATCAGT GACAAGAACA ATTCCAACCA     1260

AGCAACAGTC TTCAAGAAAT TAAACTGGCA AGTGGAATGT TTAACAGTTC AGTGTCCTTT     1320

AGTGCATTGT TTATGTGTGG GTTTCCTCTC TCCCCTCCCT TGGTCTTAAT TCCTTACATG     1380

CAGGAACACT CAGCAGACAC ACGTATGCGA AGGGCCAGAG AAGCCAGACC CAGTAAGAAA     1440

AAATAGCCTA TTTACTTTAA ATAAACCAAA CATTCCATTT TAAATGTGGG GATTGGGAAC     1500

CACTAGTTCT TTCAGATGGT ATTCTTCAGA CTATAGAAGG AGCTTCCAGT TGAATTCACC     1560

AGTGGCCAAA ATGAGGAAAA CAGGTGAACA AGCTTTTTCT GTATTTACAT ACAAAGTCAG     1620

ATCAGTTATG GGGAGGATCC AGAATTCTCG AGTTAGTAGT AGTAGT                   1666
```

(2) INFORMATION FOR SEQ ID NO:92:

(i) SEQUENCE CHARACTERISTICS:
        (A) LENGTH: 1033 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: G180con.seq (xi) SEQUENCE DESCRIPTION: SEQ ID NO:92:

```
GGATCCTCTA GAGCGGCCGC CTACTACTAC TACTCGAGAA TTCTGGATCC TCGGCCTGTG       60

GAGGATAGGG AAATGGAACA GTCCTGGCAG TTCAGGTGGC TGGGGCTGG GACCTTTGGA       120

CAGGCTGTAT ATTAAGCAGG TTTCACGCGA CGCCTCCTCT TCTGAGCATT CCCCATGGCC      180

TCGCTAGTGC AGGATGGACA GGAACTGTAC TCAGGTCCAG GTGACAGCTC ATGCCTGGAT      240
```

```
TTTCCCAAGG GGGCGGATCC AACCAGTCCA CCAGTCCGTT CTGGCAGCTT TAAGCTCCTC      300

TCAGACAGGA TGACATCCAA CTTGTTTCAA GGGCTTTCCA GTGGGCTGCA CTTGTTCTGT      360

CCCACAGGAT CTATAGGGAA ACCCCAGCTC TGGGCAAACA GACCCCCACC CCCTGACTAA      420

GGCCTCCAGA ATCTGGGCCA GAGGCCAGGG TGGGGCAAGA CACTGAGCCA GGACAGCGGT      480

TTTCTGGCTT CCTTAGTTTG TGTCCACAGA CATCCTCACT ATCCTAGGAG ATGACCCCAG      540

CAGGAATGGG GAGCTGAAGC CTGAAGAGTC ACTGAAATGA TTTACATAAT TTCCTTAATG      600

CTCACCACGA TCATGTGAGA GAGAGAACAT GACCCGTTTC ACAGACGCAT CACTGAAGCT      660

GTGAGCAGAG AAACGACTTG TCTTGCCAGA CAGTGGCAGA TACAACACTT AACCCAAAGT      720

CTCTGAGTCT CCTCAGGTGC CCTTTCATCA CTCTTCCTGC TACTTGGCAT CAACCAGCCG      780

GGATGAGACA CTGAAAGGGA TGCCAGGTCT TTGTTATGTT GCATCCAAAT GCTAGCTAGC      840

CCCTACCAGC CCATCTACCA CACCCGGGCT GCCTCTCATA TCTAGTATCT CAGCCCTCCA      900

GACCCTCACT CCTCCTTGAG ACTCTAGCCC CCAGTCCCCA GTTCCTCCCA GACTTCCCAG      960

ACTCTTCACA ATCACCAGTG TGGGAGGATC CAGAATTCTC GAGTAGTAGT AGTAGTAGTC     1020

GACCCGGGAA TTC                                                       1033
```

(2) INFORMATION FOR SEQ ID NO:93:

(i) SEQUENCE CHARACTERISTICS:
        (A) LENGTH: 1950 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: G310con.seq (xi) SEQUENCE DESCRIPTION: SEQ ID NO:93:

```
CTCTGTCATC CAGGCTGGAT TGCAGTGGCA CCATCACAGC TCACTGCAGC GTCAACCTCC       60

TGGGCTCGGG TGATCCTCCC ATCTCAGTCT CCTGGGTAGC TGGCACTATA GGCATGTGCC      120

ACCACGCCAG GCTAATTTTT GTATTTTTTG TAGAGATGGG ATTTCTCCAT GTTTCCTAGG      180

CTGGTCTCAA ACTTCTGGGC TCAAGCAATC TGCCTATGTT GGCCTCCCAA AGTGCTGGGA      240

TTACAGGTGT GTGCCACTGC ACCCGGCAAC TTACATTTTT AAAAGATCTC TAGCTTTTGT      300

GTGGGCACAG ATTAGGTTGT AATGTTCGAC CAGAGAAACA AGTTAGGATG CTATTGCTCC      360

ATGGTGAGTG ACATGGTTAT ACAGGGTGAA TGGTGCAGGG TGGGCTGGAG GAGAAGACAG      420

AATCCTACAG TGCAGGGCAT TGTAGTGGGC ATCTGATCTC TCTCTTCTCC CACCTCTATG      480

CAGCTGCTTC TCTCTCCTCA GAATCCAGAC CCAAATTTTA CCTTCTGCTG GGAAAGCCTT      540

CCTTCCCTAT TTTTTGTTTG CAGGTGGCGG GGGCTCCCTG GACCTGGGAT TCCCACGTTC      600

TTCCTCCTAA CTTGCTGCCT CGTGGCCCTA GACCCCTCTT GTGTAACACA GACATCAGTC      660

AGGCTCTCTC AGGCTCCTAA GACCTGGACG ACAGGCTCAA GCTCCTATTT GCTCACGTGC      720

AAGTGGAAAG CTTTTGCCAG GGTGTTTGCA AGTTCCCTTG TGCATGACTG TGCATGACTA      780

GCACTGACTC TCTCCTGATA CAGCATGGTT AGATCTGTGT GTGGCTCATC AGGACATTCA      840

ACAAGTAATG CCCCTGTTCT GCACCCCACA GAAGGCAGTC CTTTCCACTG AGTCCCATTC      900
```

-continued

```
ACACAGCCAA GCTGACCATC ACCCGGATCT GCCTGTGGCA GAAGCAACTT CAAAGTGAGC      960

GCTAGTGCTC CTATTCTTGA AGTCCTGTGG TCACGCTACA GTGATAGAAC TTCTTCTTCT     1020

TCACCCCCTT TCCATTCTGT CTGCAGCTTT GTGCCATCTT GCCAGTTCCC CCTCTCTCTT     1080

CACCCAATTG CAGTTTATTT CTAATACACA GAGCAATTTC TGTAGCCCTT TTGTAACAAT     1140

TCATTGCTCA CCTATGGACC CAAGATCTCA GCTTCCTACC TCCCTCTAGT GGCTGATGCA     1200

GGTATTTCCA AAAAAAAAGT CCTAGAGCAG GATCCTGGCT GGCCACACGG CTGTCCAGTG     1260

CTGCTCCTGC CCACAAGGTT CTAAGAGGTT AAGGCTTGAC ATATCAGAAA GGAAAGGAA      1320

GCCTGTGTGA CACAGAAGCC TGGGTTGAGG GAGGCTACGC TCTGTGTACT GTCCCCGGGC     1380

AGAGGCGGTT TTCTGGGTCA CCTGCATGTC CCAACACCGG CCTCTGGTGG TCGGCAGATG     1440

TTAATCCTAA AACCCTTCTG TCCCCACCTC AGAGGTGAAG TACCTGTGCA CTAGCCTTCC     1500

CCGTCTGGGT CCCCCAAGGC CCCCACACTG GGCGCACAGG GTACAGGGAG GAGCCAAGCC     1560

CTCTGCTCCA GTTCTGCCTT CTGCGCAGGA GCCCTTTGAC TTCTGGGAGT CAACCCCAGC     1620

TCACCCAACA AGGAGATAGG GCAGGTGGGA GACACCCTAA GCTCAGAAGG CCTACAGGAG     1680

ATGGAGAGCA CCCATCCTCC ACCTCTACTC CTTCTCCAGA CCACTCCACA CCTCGCAGCT     1740

TCTTGCTCCT CACCCTCGCA TTTGGCCCAG TGGGCACCAA GAACAAGCCA GGGTGACTGG     1800

CTAAGCTGGG GCCAAACTCA CTGACAGAAT TGGAATTGTG TCAAAACACC ACTTTTATGT     1860

CCTCACCTTT CAGGCCTGCA TCAGTGTGAG CTCTGCAGAG AAAGGGGCCT GTCTTACTGA     1920

ACCCTCAGAT CCCAGCACGC TGCTGTCCTA                                      1950

(2) INFORMATION FOR SEQ ID NO:94:

(i) SEQUENCE CHARACTERISTICS:
        (A) LENGTH: 1328 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
         (C) INDIVIDUAL ISOLATE: G326con.seq (xi) SEQUENCE DESCRIPTION: SEQ ID NO:94:

GTTTCCAAGA TGATTGTAGA ACTAAAATGA GTTGTAAGCT CCCCTGGAAG AAGGGATGTG       60

GAACCTGTAA CTAGGTTCCT GCCCAGCCTG TGAGAAGAAT TTGGCAGATC ATCTCATTGC      120

CAGTATAGAG AGGAAGCCAG AAACCCTCTC TGCCAAGGCC TGCAGGGGTT CTTACCACCT      180

GACCCTGCAC CATAACAAAA GGACAGAGAG ACATGGTAGG GCAGTCCCAT TAGAAAGACT      240

GAGTTCCGTA TTCCCGGGGC AGGGCAGCAC CAGGCCGCAC AACATCCATT CTGCCTGCTT      300

ATGGCTATCA GTAGCATCAC TAGAGATTCT TCTGTTTGAG AAAACTTCTC TCAAGGATCC      360

AGAAAATATG CTCTTTAAAA TATTTTAAAA CTGATATAGA CCCAAAGGAG AGACCCAGTA      420

ACAATATTCA GCTATATTAT CCATTCTCTC TTTCTTTCAT TCAACAAATC TGTATTGATC      480

ACAGGCTCTC TGCTGGGTGT GGGATGCAGC TGTGGGCCTG TGCTGGAGGT CCTTAGAGGC      540

CAGTACTCCT ATCCTGGGCT TTATCTGCAT GGATTGCTGC AGTGTTGGGC TCCACTGCTG      600

TGTGAAGCAA TTGCTCCTGC TCTTTCTGGG CATGGGAGAA GGGTCAGAGC AGTCGGACAC      660

AGATTCCCAG GCAGGAGAAT GGAACTCCTT CCGAGGAAGA AGACGTGTTT TCCTTCCAGC      720
```

```
ACACACCCAG GCATGGTGGT CAGGACCGTG GACCAGGTCC CCATCTTGTG CATGCACCAA      780

GCCCCAGGAT CAGGAGCAGA GCTAGTGAGG GAGCAAGATG GATGAGGACA GCACGGTGCT      840

GACCACTCTA GACAGACAGG AGACAGGAAA CAGGATCTCA CTTGCAAAAA GACTGATCTC      900

AACTTGATCA ATTAGGCAGA TACTTGAGTT CCAGTATACT CCAGGACTAT TCTAGGGGCT      960

AGGATTCAAC AGTGAATAAA ACAGACAAAA TCCTTTCCCT TGTACACTTA TATCTTCTCA     1020

AAAAAGCTCC TTTCCCCTCT TTCTTATCAG GGTCTAATAT AGTTAATAAG GACTTAAGAC     1080

TGGAATATCA CATCTAAATC CCCAATAATG AGCCCTCACC AATCTGCCAG GTCCCAGAGA     1140

AGCTAAAAAC AATCAGGGCT GTTTGCAGCT AACTGAAATA AAACTTGATT CGAACTCATG     1200

TCAAGCCTGT TGACAACACA CACACATGTC CACGTGTCAC TGCTGTGCAT AGAAACCTCT     1260

GACTCACTAC CATCTGAAGT CCAGGCTCCT TCACAGGTCA TTCAAGGTCG ACCTCTGCCC     1320

CCTCTGAC                                                              1328
```

(2) INFORMATION FOR SEQ ID NO:95:

(i) SEQUENCE CHARACTERISTICS:
        (A) LENGTH: 1093 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: G164con.seq (xi) SEQUENCE DESCRIPTION: SEQ ID NO:95:

```
GTGCTCAATA AATATTTTTG GAAAGAATAA ATCTTCAATC AATCCTATTC AGTAGGTTTG       60

ATGATCACTT CCAATCTATA GAAAGGAAAA CTGACTCCTA GAAAGATTAA TTAACTTGCC      120

CAATGGCAGG TAGCAGTAGA AGCAGAACTT AAAACCAGGT AGCCTGACTT TAGCATCTTA      180

ACACTGGGTT GTTTTGCTTC TACTACTTGC ACTGAAGGCA CTTACCACAA TTTATAGTTG      240

TTTTATTTGT TTGTTGTCTG ACCCTCCTAA ATGTGTATGA TGCTGCTAGA GCAGGGCTAT      300

GTCCTGCTCC CTGCTGTGCC ACCAATACTT AGAACAGTGC CTGGCACATT GCAGCTGTGT      360

GAGTATTTGC TGAGTGAATG AATAAACAAC CCAAATGAAC AGACAAGTGA GGGATGACTG      420

TGGAGGAATA GGGGGTGCCA GTGTGGCAGT TTCCCAGGCC CCAGCTGGAT CCCAGTGCCC      480

AGTCCAGCTG TACCCACGTA AAGGGATCTG CCAAGAGGTG GCTTTTCGCT GTTGCAGAAG      540

GCATCTCTTG GGGCTGATGA CGGTGAGTCT CTCATTCTTA ACAGCAAGAG TCACCCTGCT      600

CCATGAATCT TCAAATTTGG GGTCATTTCC CACCTAAAGG CAGAGATTTG GCCTATGTTC      660

CCAACCACAG CTGAGAGTCC AACCTGCCCC TCGGGTGACA CACATGGCTC TGGGTAGGAT      720

CCGTGTATAC TGCCTCGATT CTACTCATTA CATTATGTCA GCACCTTTTT CAGCTTCTGA      780

GAAACAGGAA GCATCATGAT GTGTGGTGGG GCTTGAAGAA GATGATAAGA GACATAATCA      840

CATTTCTTTG GTTGGGCAC AGAGGGCTGG GGTTCCTGTT TGCTCTGACT CTAAAGTGTC      900

ACCTTTTCCC TTAAGCCAGA ATGTTGGAGG ATGAGGACTA TTTAGACAAC CTGCTTTCAA      960

GGGGAAAGAA AAGAGCAGGG ATCAGAGCCT TTAAAATTAT TATTATGAAA CATCATACAT     1020

ACAAAAAAAT TACAATCTCT ATGTATAGTT GTTAAAACAT AACAAAACCC ATGTGTCCAC     1080
```

```
ACCTGGATCC TGG                                                                  1093
```

(2) INFORMATION FOR SEQ ID NO:96:

(i) SEQUENCE CHARACTERISTICS:
        (A) LENGTH: 2104 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: G65.seq (xi) SEQUENCE DESCRIPTION: SEQ ID NO:96:

```
GAATTCTGGA TCCTCGACCG GGCGACGCCG CGGGAGGTTC TGGAAACGCC CGGAGCTGCG    60
AGTGTCCAGA CACTTCCCTC TGTGACCATG AAACTCTGGG TGTCTGCATT GCTGATGGCC   120
TGGTTTGGTG TCCTGAGCTG TGTGCAGGCC GAATTCTTCA CCTCTATTGG GCACATGACT   180
GACCTGATTT ATGCAGAGAA AGAGCTGGTG CAGTCTCTGA AGAGTACAT CCTTGTGGAG    240
GAAGCCAAGC TTTCCAAGAT TAAGAGCTGG GCCAACAAAA TGGAAGCCTT GACTAGCAAG   300
TCAGCTGCTG ATGCTGAGGG CTACCTGGCT CACCCTGTGA ATGCCTACAA ACTGGTGAAG   360
CGGCTAAACA CAGACTGGCC TGCGCTGGAG GACCTTGTCC TGCAGGACTC AGCTGCAGGT   420
TTTATCGCCA ACCTCTCTGT GCAGCGGCAG TTCTTCCCCA CTGATGAGGA CGAGATAGGA   480
GCTGCCAAAG CCCTGATGAG ACTTCAGGAC ACATACAGGG TGGACCCAGG CACAATTTCC   540
AGAGGGGAAC TTCCAGGAAC CAAGTACCAG GCAATGCTGA GTGTGGATGA CTGCTTTGGG   600
ATGGGCCGCT CGGCCTACAA TGAAGGGGAC TATTATCATA CGGTGTTGTG GATGGAGCAG   660
GTGCTAAAGC AGCTTGATGC CGGGGAGGAG GCCACCACAA CCAAGTCACA GGTGCTGGAC   720
TACCTCAGCT ATGCTGTCTT CCAGTTGGGT GATCTGCACC GTGCCCTGGA GCTCACCCGC   780
CGCCTGCTCT CCCTTGACCC AAGCCACGAA CGAGCTGGAG GGAATCTGCG GTACTTTGAG   840
CAGTTATTGG AGGAAGAGAG AGAAAAAACG TTAACAAATC AGACAGAAGC TGAGCTAGCA   900
ACCCCAGAAG GCATCTATGA GAGGCCTGTG GACTACCTGC CTGAGAGGGA TGTTTACGAG   960
AGCCTCTGTC GTGGGGAGGG TGTCAAACTG ACACCCCGTA GACAGAAGAG GCTTTTCTGT  1020
AGGTACCACC ATGGCAACAG GGCCCCACAG CTGCTCATTG CCCCCTTCAA AGAGGAGGAC  1080
GAGTGGGACA GCCCGCACAT CGTCAGGTAC TACGATGTCA TGTCTGATGA GGAAATCGAG  1140
AGGATCAAGG AGATCGCAAA ACCTAAACTT GCACGAGCCA CCGTTCGTGA TCCCAAGACA  1200
GGAGTCCTCA CTGTCGCCAG CTACCGGGTT TCCAAAAGCT CCTGGCTAGA GGAAGATGAT  1260
GACCCTGTTG TGGCCCGAGT AAATCGTCGG ATGCAGCATA TCACAGGGTT AACAGTAAAG  1320
ACTGCAGAAT TGTTACAGGT TGCAAATTAT GGAGTGGGAG GACAGTATGA ACCGCACTTC  1380
GACTTCTCTA GGCGACCTTT TGACAGCGGC CTTCCAACAT TAGGGCAGAG GGGAATAGTG  1440
TTAGCGACGT TTCTTAACTA CATGAGTGAT GTAGAAGCTG GTGGTGCCAC CGTCTTCCCT  1500
GATCTGGGGG CTGCAATTTG GCCTAAGAAG GGTACAAAGC TGTGTTCTGG TACAACCTCT  1560
TGCGGAGCGG GGAAGGTGAC TACCGAACAA GACATGCTGC CTGCCCTGTG CTTGTGGGCT  1620
GCAAGTGGGT CTCCAATAAG TGGTTCCATG AACGAGGACA GGAGTTCTTG AGACCTTGTG  1680
GATCAACAGA AGTTGACTGA CATCCTTTTC TGTCCTTCCC CTTCCTGGTC CTTCAGCCCA  1740
```

```
TGTCAACGTG ACAGACACCT TTGTATGTTC CTTTGTATGT TCCTATCAGG CTGATTTTTG    1800

GAGAAATGAA TGTTTGTCTG GAGCAGAGGG AGACCATACT AGGGCGACTC CTGTGTGACT    1860

GAAGTCCCAG CCCTTCCATT CAGCCTGTGC CATCCCTGGC CCCAAGGCTA GGATCAAAGT    1920

GGCTGCAGCA GAGTTAGCTG TCTAGCGCCT AGCAAGGTGC CTTTGTACCT CAGGTGTTTT    1980

AGGTGTGAGA TGTTTCAGTG AACCAAAGTT CTGATACCTT GTTTACATGT TTGTTTTTAT    2040

GGCATTTCTA TCTATTGTGG CTTTACCAAA AAATAAAATG TCCCTACCTG AAAAAAAAAA    2100

AAAA                                                                 2104
```

(2) INFORMATION FOR SEQ ID NO:97:

(i) SEQUENCE CHARACTERISTICS:
        (A) LENGTH: 1534 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: Septin-2.seq (xi) SEQUENCE DESCRIPTION: SEQ ID NO:97:

```
CGGGGAGGCC GGTCCCGCGG GCGGGGGAAG GGGCGGTTCC GCGGCTTCTC CCGCCGCCGC      60

CGCCAAGGGG AGTTTCCAGG AAGTGGCCAT ATTGGATCCA TTCAGCCGCA GCCCGCCCGG     120

GCGGAGCGCG TCCCGCAGCC GGCTGGTCCC TGTCTCTGCC CCTGCGCTCG TCCCAGCCCA     180

CCCGCCCGGT GCGGAGCTCG CCATGGCGGC CACCGACCTG GAGCGCTTCT CGAATGCAGA     240

GCCAGAGCCC CGGAGCCTCT CCCTGGGCGG CCATGTGGGT TTCGACAGCC TCCCCGACCA     300

GCTGGTCAGC AAGTCGGTCA CTCAGGGCTT CAGCTTCAAC ATCCTCTGTG TGGGGGAGAC     360

CGGCATTGGC AAATCCACAC TGATGAACAC ACTCTTCAAC ACGACCTTCG AGACTGAGGA     420

AGCCAGTCAC CATGAGGCAT GCGTGCGCCT GCGGCCCCAG ACCTATGACC TCCAGGAGAG     480

CAACGTGCAG CTCAAGCTGA CCATTGTGGA TGCCGTGGGC TTTGGGGATC AGATCAATAA     540

GGATGAGAGT TACAGGCCCA TAGTTGACTA CATCGATGCG CAGTTTGAAA ATTATCTGCA     600

GGAGGAGCTG AAGATCCGCC GCTCGCTCTT CGACTACCAT GACACAAGGT CCACGGTTTG     660

GCTCTACTTC ATCACGCCCA CAGGGCACTC CCTGAAGTCT CTAGATCTAG TGGCCATGAA     720

GAAGCTAGAC AGCAAGGTGA ACATTATCCC CATCATCGCC AAGGCTGACA CCATCTCCAA     780

GAGCGAGCTC ACACAAGTTCA AGATCAAGAT CATGGGCGAG TTGGTCAGCA ACGGGGTCCA     840

GATCTACCAG TTCCCCACGG ATGATGAGGC TGTTGCAGAG ATTAACGTAG TCATGAATGC     900

ACATCTGCCC TTTGCCGTGG TGGGCAGCAC CGAGGAGGTG AAGGTGGGGA ACAAGCTGGT     960

CCGAGCACGG CAGTACCCCT GGGGAGTGGT GCAGGTGGAG AATGAGAATC ACTGCGACTT    1020

CGTGAAGCTG CGGGAGATGT TGATCCGGGT GAACATGGAA GACCTCCGCG AGCAGACCCA    1080

CAGCCGGCAC TACGAGCTCT ACCGGCGCTG CAAGTTGGAG GAGATGGGCT TTCAGGACAG    1140

CGATGGTGAC AGCCAGCCCT TCAGCCTACA AGAGACATAC GAGGCCAAGA GGAAGGAGTT    1200

CCTAAGTGAG CTGCAGAGGA AGGAGGAAGA GATGAGGCAG ATGTTTGTCA ACAAAGTGAA    1260

GGAGACAGAG CTGGAGCTGA AGGAGAAGGA AAGGGAGCTC CATGAGAAGT TGAGCACCT     1320
```

```
GAAGCGGGTC CACCAGGAGG AGAAGCGCAA GGTGGAGGAA AAGCGCCGGG AACTGGAGGA       1380

GGAGACCAAC GCCTTCAATC GCCGGAAGGC TGGGTGGGAG GCCTGCAGTC GCAGGCCTTG       1440

CACGCCACCT CGCAGCAGCC CCTGAGGAAG ACAAGGACA AGAAGAAGTA GGTGGCAGGC        1500

TGCGCCTGCG CTGGCTCCTC TTGCTCCTGT GGGC                                   1534
```

(2) INFORMATION FOR SEQ ID NO:98:

(i) SEQUENCE CHARACTERISTICS:
        (A) LENGTH: 414 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: G42con.seq (xi) SEQUENCE DESCRIPTION: SEQ ID NO:98:

```
CAGGCATAAG CCACCGTGCC TGGCCTGGAA TATTAGTTTT TATATAACTG GTGTAAAGGG        60

TCAAAGAGAT AATATATGTA AACACTTAGC CTGGAACCTG TCTCAAAGTA CCTACTCAAA       120

AAAATGCTAG CTGTGAAGAT GGTGATCCTG TTTAAGGAAG GGTGACTGCC TAAAAGAGAG       180

CAGAAAGTAG GACTAAAAAG GAATTATTTC AATTTGTACC ATCCATGCTG TCCACAGGAA       240

GGCAAAGAGA GAGACCTACA AAGTCTCTGT CCCCAACATG CACTCTGCCA AGTTATATAA       300

CTGTTCTGGT CTGAGACCCA TGCTTAGAGA GGGAGATTAT CCAGGAACCC AGTAGTATAA       360

CTTCTCTTTT CTTAACGAGG TCATGAAGGT AGGAGAAAGC TCCTCTGGCC TCAC            414
```

(2) INFORMATION FOR SEQ ID NO:99:

(i) SEQUENCE CHARACTERISTICS:
        (A) LENGTH: 606 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: G105con.seq (xi) SEQUENCE DESCRIPTION: SEQ ID NO:99:

```
TGGGAAGATA GGGATGGGAG TGGAGGGGCT GTGGGAAGGA GAAGGGTCAC TCAGGGACCT        60

GGCTGTGCCC CTTGCATCCT GACAATGGAT CCACCACAAC TCTACCAGTC TGTATTAGGG       120

GAACATGAGC AAATGGCATC GTGTCTGTGC CAGTCACCAA GCACTGAGGG GAAGCTCTGG       180

AAGTTGCCGC CTGAACCTGC CCTCCAGTCT TGCAAATGCT GAGCAGGAGC CACCAGCCTT       240

GGACTGTCTG TGCTTCTTGC TAGAGCATGT GGGTCATTCC AGCCTTTCCC CAGAACGTCC       300

ATTCTCTCCA CACCTTCTTC ATTCCAAATG GGGATCCTTG CCTTTCTTTT GGACTCCAGA       360

GACATGCATA AAACCACAAC ACAGCTTTAG AAAACAAGGC ACACCTGTAT TAGTCTTACA       420

CCTAAATTGA ATGCAGCCTG CCATAAGGGA GGAATTACAG TCCTTCTAGA GGCCCAAGGT       480

ACCTGCAGCT CCCCCTGACC AGTCCTGTCA AAGCCTTGTT TTTGTCAAAA TGCCACCTTG       540
```

```
GACTCTGTCT GAGAGTTCTG CTGCCCACCA AGAGGGATGG ACAAAGTCTG TTTATCCAGA      600

AACTTG                                                                 606

(2) INFORMATION FOR SEQ ID NO:100:

(i) SEQUENCE CHARACTERISTICS:
         (A) LENGTH: 421 base pairs
         (B) TYPE: nucleic acid
         (C) STRANDEDNESS: double
         (D) TOPOLOGY: linear (ii) MOLECULE TYPE: cDNA to mRNA (iii) HYPOTHETICAL: NO (iv) ANTI-SENSE: NO (vi) ORIGINAL SOURCE:
         (C) INDIVIDUAL ISOLATE: G98con.seq (xi) SEQUENCE DESCRIPTION: SEQ ID NO:100:

CATAATGGAC CCCTCTAAGG ACTTCATGAA AGCTACGGAC CTCTCTCCAA AAAATGCTCA       60

CATGTAGTCT CTAACATTGT GCATATAATT TCGAGGGGTT TGGGATTCTC TAAGCCGTTA      120

ATGCTTCCTT GAGTTAAAAG CTTTAGAATT ATACAAATAA CCTGCTTATA AGAAATGGAT      180

CAAAACACTA TTCTCCCTCC TGTCATAAAG TAAATGCCAA AACCACAGGC CACTTAGCTA      240

AGGGGCATCA GCCTTGTGGA CAAAAGAGTT CTGCTTTTCA TACCACTAGT GGCTGGTGAG      300

AGCTCCTTTC ACTTTGCAGA GAGAATGCTG GTCTTCTTGG GACTACAGAG GCAGACACCG      360

TGGCACTACT ACAGATCTAC AATCTAGCAC ATGTGCATGT GTGCATGATG TCAACCTCTC      420

C                                                                     421

(2) INFORMATION FOR SEQ ID NO:101:

(i) SEQUENCE CHARACTERISTICS:
         (A) LENGTH: 392 base pairs
         (B) TYPE: nucleic acid
         (C) STRANDEDNESS: double
         (D) TOPOLOGY: linear (ii) MOLECULE TYPE: cDNA to mRNA (iii) HYPOTHETICAL: NO (iv) ANTI-SENSE: NO (vi) ORIGINAL SOURCE:
         (C) INDIVIDUAL ISOLATE: G73con.seq (xi) SEQUENCE DESCRIPTION: SEQ ID NO:101:

GTGACTGTGG AGGGCGAGCT GAGCCCTGGC CGCCGCCACA ATGGGCCGCG AGTTTGGGAA       60

TCTGACGCGG ATGCGGCATG TGATCAGCTA CAGCTTGTCA CCGTTCGAGC AGCGCGCCTA      120

TCCGCACGTC TTCACTAAAG GAATCCCCAA TGTTCTGCGC CGCATTCGGG AGTCTTTCTT      180

TCGCGTGGTG CCGCAGTTTG TAGTGTTTTA TCTTATCTAC ACATGGGGGA CTGAAGAGTT      240

CGAGAGATCC AAGAGGAAGA ATCCAGCTGC CTATGAAAAT GACAAATGAG CAACGCATCC      300

GGATGACGGT TCCCTGTCTC TGAAAGACCT TTCTCTGGAA GAGGAGTCTG CATTGTAGTG      360

TCTCAAAGAC ACAATAAACT TCCTATGGTC TG                                    392

(2) INFORMATION FOR SEQ ID NO:102:

(i) SEQUENCE CHARACTERISTICS:
```

(A) LENGTH: 2200 base pairs
(B) TYPE: nucleic acid
(C) STRANDEDNESS: double
(D) TOPOLOGY: linear (ii) MOLECULE TYPE: cDNA to mRNA (iii) HYPOTHETICAL: NO (iv) ANTI-SENSE: NO (vi) ORIGINAL SOURCE:
(C) INDIVIDUAL ISOLATE: G89con.seq (xi) SEQUENCE DESCRIPTION: SEQ ID NO:102:

```
CCACCCAGCC TCAGCACTCA TCTGCGCAGC CATGGAGGCC CTGGGACCTG GGGGCGACCG      60
CGCCTCCCCG GCCTCGTCCA CTAGCAGCCT GGACCTGTGG CATCTGTCCA TGCGCGCGGA     120
CTCGGCCTAC AGCTCTTTCT CCGCAGCCTC CGGCGGCCCC GAGCCGCGCA CGCAGTCGCC     180
GGGGACAGAC CTCCTTCCTT ACCTAGACTG GGACTACGTG CGTGTGGTTT GGGGCGGCCC     240
GGGCCCCGCC CCGCCCGACG CTGCCCTTTG CACATCCCCG CGGCCCCGGC CCGCGGTTGC     300
AGCCCGCAGT GGGCCGCAGC CAACAGAGGT CCCGGGGACC CCGGGACCAC TGAACAGGCA     360
GGCCACCCCG CTGCTGTACG CGCTGGCGGC CGAGGCGGAG GCCGCGGCGC AGGCTGTCGA     420
GCCGCCCAGC CCGCCGGCCT CGAGGGCCGC CTACCGCCAG CGGCTTCAGG GCGCGCAGCG     480
GCGAGTGCTC CGGGAGACGT CGTTCCAGCC CAAGGAGCTC CGCATGAGCC TGCCCGCCCG     540
TCTGCGGCCC ACTGTCCCAG CGCGGCCCCC GGCGACTCAC CCGCGCTCCG CCTCGCTCAG     600
CCACCCGGGC GGGGAGGGGG AGCCGGCGCG CTCCCGGGCT CCCGCGCCAG GAACTGCCGG     660
CCGGGGTCCC CTCGCCAACC AGCAGCGGAA GTGGTGCTTC TCAGAGCCAG GAAAGCTGGA     720
TCGTGTGGGT CGGGGCGGTG GGCCGGCGCG GGAATGCCTG GGTGAGGCCT GCTCCAGCTC     780
TGGCCTCCCT GGGCCCGAGC CCTTGGAGTT CCAGCATCCG GCGCTGGCTA AGTTTGAAGA     840
TCACGAGGTC GGATGGCTGC CCGAGACGCA ACCCCAAGGC TCCATGAACC TGGACTCCGG     900
GTCCTTGAAG CTCGGTGATG CCTTCAGGCC CGCCAGTCGG AGTCGGAGCG CTTCAGGCGA     960
AGTCTTGGGT TCCTGGGGAG GATCAGGAGG GACCATACCC ATTGTCCAGG CTGTCCCCAA    1020
GGAGCAGAAA CCCCCAGACC ATTGTTTCAG ACCAAACTTT CCAGGTTCTT GCCTCAGAAA    1080
GAGGCTGCGG TGATGTATCC TGCAGAGTTA CCCCAGAGCA GCCCTGCTGA CAGTGAACAG    1140
AGGGTCTCAG AGACCTGCAT TGTGCCTGCC TGGCTCCCCT CCCTTCCTGA TGAAGTGTTC    1200
CTAGAAGAGG CCCCACTGGT CAGAATGAGA TCACCACCAG ACCCCATGC CTCCCAGGGG     1260
CCCCCAGCCA GGTCCTATCA GTTCAGCTTC ACCCAGCTCC TGCCGGCTCC TCGGGAGGAG    1320
ACAAGGCTTG AAAACCCTGC CACCCACCCT GTGCTTGACC AGCCATGTGG GCAGGGGCTC    1380
CCTGCACCAA ACAACAGCAT CCAGGGCAAG AAAGTGGAGC TGGCCGCCCG CCTCCAAAAG    1440
ATGCTTCAGG ACCTTCACAC GGAGCAGGAG CGGCTGCAGG GGAGGCACA AGCGTGGGCC     1500
AGGCGCCAAG CGGCTCTGGA GGCTGCAGTG CGCCAGGCCT GTGCCCCTCA GGAGCTGGAG    1560
CGGTTCAGCC GGTTCATGGC CGACCTAGAG CGCGTGCTTG GCCTTCTGCT GCTGCTGGGC    1620
AGTCGCCTGG CGCGCGTGCG CCGCGCCCTG GCCCGGCGG CCTCAGACAG CGACCCTGAT     1680
GAGCAGCGAC TCCGGCTCCT GCAGCGGCAG GAGGAGGACG CCAAGGAGCT GAAGGAGCAC    1740
GTAGCGCGGC GCGAGCGGGC CGTGCGGGAG GTGCTGGTGC GAGCACTACC GGTGGAGGAG    1800
CTGCGCGTCT ATTGCGCCCT GCTGGCGGGC AAGGCCGCCG TCCTGGCCCA GCAGCGCAAC    1860
CTGGACGAGC GCATCCGCCT CCTTCAGGAC CAACTGGACG CCATCAGGGA CGACCTTGGC    1920
```

```
CATCATGCCC CGTCTCCCAG CCCGGCGCGG CCCCCAGGGA CCTGTCCTCC AGTTCAGCCG    1980

CCCTTCCCTC TTCTCCTTAC ATAAGATACC ACTGGGTCAG CCAGGCCTGA GGCGGGCAGT    2040

CGAGGGTGGG AGCTGAAGGG AAGCCATGTT CGGCGGTGCC CGAAACCGGC GCGCAGTCTG    2100

TCTTGAACAT CCTGCTCGGC ACAAAACTTA CCCCTGAGAG CGGCTGGCGC AAACCTCAGG    2160

GCTCCTCATT GGAACAAATT GCCGTGCTGT GCATTCACAT                          2200
```

(2) INFORMATION FOR SEQ ID NO:103:

(i) SEQUENCE CHARACTERISTICS:
        (A) LENGTH: 371 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: G102.seq (xi) SEQUENCE DESCRIPTION: SEQ ID NO:103:

```
GGGGGATCCA GCTCAGAAGC AGAGTGTCCA CGCCAGGGAA TAGTGTGGGG ATTCAGAGCC     60

TGATAATGAT GAGAAGGGGA CCCACCTGAG GGTTAAGTCG CTAGGGGGA AGTCAGATCA     120

TAGAGTAGAG ACGGCATTCT TGCGAGAAGC CACCTGGTAT AAAGTATCAG ACCGAGAAGA    180

GTGACCCTCT CAGTGACACA GATCTGGGGA GATTCAGGTC AGAGTACAGT GGGCATCCCT    240

GCAAGAGGCC ACCTGGTATC AGAGAAGGGC GGGGAATGAG GACATGATCT AGCACCAGAA    300

GTCAAAGTGT ATACAGAATG GAAAAGCATC CCATGAGGGA GTCGGAATGA AGAGTCAAGA    360

GCCTACGCAG G                                                         371
```

(2) INFORMATION FOR SEQ ID NO:104:

(i) SEQUENCE CHARACTERISTICS:
        (A) LENGTH: 407 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: G57.seq (xi) SEQUENCE DESCRIPTION: SEQ ID NO:104:

```
GGCAGAGGAG GACAGGCACC TACTGCATCC AAGCCTTAGG ATATGAGTCA TGTTCCAAAG     60

GTGGGATTGG GAAGGACAAT CAGGGCGTGA TAGTAATATA TGCTGAGTAG AGGCACTAGA    120

CATGGGAAGC AACTAATTCC AACTGAAGAC CCATAGGTGT GGGAGAGAGA GGCTAGAGAG    180

GTCAGCAGGT CCTGAACATC TGCAGAAGGT GGATTGTCCT GTTGGCTCAG GGAGCTTAGG    240

CTTCAAGCCC CCTCACTTGC ATCAGCCCCT TCCAAGGCCC TGCACTTCAA TTTTACCTGG    300

TTTTTCTTAG AAAGGGCCCT CAATATTGTA AAAGCTTGAA GTCTCACAAA TCCCTGGATC    360

TGCTGCTGAT GCCCTGTAAC TTGAATGAAA CCATTCACCA TTTAGGG                  407
```

(2) INFORMATION FOR SEQ ID NO:105:

(i) SEQUENCE CHARACTERISTICS:
        (A) LENGTH: 235 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: G108.seq (xi) SEQUENCE DESCRIPTION: SEQ ID NO:105:

```
GTCCTCTGGG AAGCAGACAC CAAAACAGAA TGAAAAGTGC AGAAGATTTA TTGGGGGTAA      60

GAAGAGCTAA TGCCTATGAA AGATAAAGGA GAAAGGAGCA GAAGTACGGA GAGAAAAGAC     120

AGCTTTCAGA CTGCAGTCCA GATCTAACTC TGGGACGCAA GAGAGGGAAG GATAATTCTG     180

TTGAAAGAGC ATCAGACTGT GATGCGGCTG TAAGAGTGTC TCAACGAGCC CAGTG          235
```

(2) INFORMATION FOR SEQ ID NO:106:

(i) SEQUENCE CHARACTERISTICS:
        (A) LENGTH: 397 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: G127.seq (xi) SEQUENCE DESCRIPTION: SEQ ID NO:106:

```
GGCAGCTGAT AAACAAACAG GGCAAGCACA TTCAGGCCAG AGCAAGGGGA AGCCCCTGAG      60

TCCCCTCTAT GTGCTCTCTG GCAAGATCTA CTTTCTGAAG CATTGACTGG AAATAGAAGT     120

CTCGCCGGGC TGGCTGGAGC CAGAGGCCCC CACACCTTAT CCCCTTTGGA ATCTGCCAGA     180

GGGCAGGTCT GAGTATGGAC TTGGATGATC AACTTGGTTA ATATTCAGGC TATCTTGACA     240

GTCTCCACAC CCGTGAGCAA TGTCCCAGGC AGCCTGCAGG CCTGATAGAA ACTCCACAAA     300

CCCGCCTATC ACGGAAGGTT TTCCCCTTTT GTCGGGGCCT ACCCAGACCC CAGGGGAGGT     360

GCATCCTTGA AAGCCGCTAT GTGAAGTCCC ACATAGT                              397
```

(2) INFORMATION FOR SEQ ID NO:107:

(i) SEQUENCE CHARACTERISTICS:
        (A) LENGTH: 266 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: G86.seq (xi) SEQUENCE DESCRIPTION: SEQ ID NO:107:

| | | | | | |
|---|---|---|---|---|---|
| CCACCCCCTG | TGGCCTTCTT | TAACCATGCT | GGCTAATTCA | GGATCCCTAG | TTCCTTATGA | 60
| CTTTCCTTTA | AAACGTCTAC | CAGAAATTGG | GGGAAAAAAA | GTGTTATTAT | AGGATTAATG | 120
| TAGGTCTTCC | CCACTATACT | GTGAATATCA | TTGAGAGCTT | GGTCCCTACA | CCTTAAATCC | 180
| CCCATCGTCA | ACTATTTTTT | CCCATCTCAG | TGTCCCATGA | TCAAGGAGAC | CCTCCCTGAA | 240
| TGTCCAGTTC | CCCAACCCTT | ACCCCC | | | | 266

(2) INFORMATION FOR SEQ ID NO:108:

(i) SEQUENCE CHARACTERISTICS:
        (A) LENGTH: 370 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: G78.seq (xi) SEQUENCE DESCRIPTION: SEQ ID NO:108:

| | | | | | |
|---|---|---|---|---|---|
| GTAGGTGATG | GGATGATGGT | GAAATACAGG | ATCAAGTACT | CAACTCCAAC | CTGATGGCCA | 60
| TACCCAGGAC | AAATGCTGCC | CCATAGTTGG | AGATCTGGCC | CATGCCTACA | AGGACAAACA | 120
| GCACGACAAA | CATCTCAAAA | TTCTTCGAGA | AGGTCTGCAG | GAAGCTGAAG | CCTGTCTGCA | 180
| CGCCCATGGT | CACGAACAGC | ACATTCTTCC | GGCCAAACCT | GGGAAGGAAA | GGAGAGTGAC | 240
| AGATAACCAG | CTGGAAAAGG | GCAGCAGGAA | TGGGCTCCAC | CAAGTGGGGC | TTTCTCAAGA | 300
| TCCATCCAGT | AAGTGGGTGT | GAACAGTGTT | GCCAGAATAC | TGGCTGCCAG | GGACAGTCTC | 360
| GGTCTCACAG | | | | | | 370

(2) INFORMATION FOR SEQ ID NO:109:

(i) SEQUENCE CHARACTERISTICS:
        (A) LENGTH: 481 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: H993.seq (xi) SEQUENCE DESCRIPTION: SEQ ID NO:109:

| | | | | | |
|---|---|---|---|---|---|
| GGGAGAAATA | GCATGGGCAC | TGTGAGACCG | AGACTGTCCC | TGGCAGCCAG | TATTCTGGAA | 60
| ACACTGTTCA | CACCCACTTA | CTGGATGGAT | CTTGAGAAAG | CCCCACTTGG | TGGAGCCCAT | 120
| TCCTGCTGCC | CTTTTCCAGC | TGGTTATCTG | TCACTCTCCT | TTTCTTCCCA | GGTTTGGCCG | 180
| GAAGAATGTG | CTGTTCGTGG | CCATGGGCAT | GCAGACAGGC | TTCAGCTTCC | TGCAGATCTT | 240
| CTCGAAGAAT | TTTGAGATGT | TTGTCGTGCT | GTTTGTCCTT | GTAGGCATGG | GCCAGATCTC | 300
| CAACTATGTG | GCAGCATTTG | TCCTGGGTAT | GGCCATCAGG | TTGGAGTTGA | GTACTTGATC | 360

```
CTGTATTTCA CCATCATCCC ATCACCTACC TTTCTGGAGA CAGCTGTAAT GTCCCTCAAG    420

GGGGACAGGG TTTCTAACAA AACTAGCCAG AGCTTCCTGG TGAACCTTAC TTACAGGCAG    480

G                                                                    481
```

(2) INFORMATION FOR SEQ ID NO:110:

(i) SEQUENCE CHARACTERISTICS:
        (A) LENGTH: 670 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: G38a.seq (xi) SEQUENCE DESCRIPTION: SEQ ID NO:110:

```
GGGGCAAGTA GCCGGTGCGG GTGGTAGAAC TGGCAGATAA AAGGGCCTGT GGTGAGACTC     60

CAGGTGTGGT TGTATAGGGG GTTGAGGGAG GTAAGCGCGG AGGCGGGATC GAGCAGGGGT    120

CCTTGTAGCC GCCTAAGAAG TGCAGTGGTG AAGCTGACTC CTGTGAGGTG GAGGGGAGGG    180

GTCTGGAAAC AGTGGAGATA CAGCAGCCCT GGGCAGAGCA GAGGAGCCAG GTGAACCCTA    240

CCTTACAGAA ATCTTGTACC CTGGCTGAAG GACGGGCAGG GAGGGGTCGT GAGGAACCCC    300

CTCGCCGGGA TCAGGAAGCC TAGGTCAGTC CGGGTTACAT AGCTGACCTG CTGTGGGACC    360

TCGGGGACCA ACACCCTCGG TTTCTGGTCC CAGGAGATGG ACAAGGACGC AATGTCTGTT    420

CCTGGCCTTG GCTCAGGGCC TAATCTGATC CGCGGATGGT CCTTGCCATC AGGGAAGGGG    480

GACGCAAGAA CTCGGCGGGG GTTTGTGGTG GGTCGCAGA GAGCAAGCCC TATATCTCCC    540

TCCGCAGACC CAGGTGCTCC CCAAACCCGG CCCGGAGCCC GCGAGAACTG GGGGCGGAGG    600

GTGTACTTAG GCGGCCCTGG GGACCTTGAC GGGACAGCTC AGCAGCAGGG GATGGGGGCT    660

CGGCGGCCGC                                                          670
```

(2) INFORMATION FOR SEQ ID NO:111:

(i) SEQUENCE CHARACTERISTICS:
        (A) LENGTH: 408 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: H90.seq (xi) SEQUENCE DESCRIPTION: SEQ ID NO:111:

```
GTCACCAGCA CCTTGGGCTG GGTGTCAGAG AGCTCACAGA ATGTGGATAA CCAACCAGGC     60

AGATGTTGGT AACAGCAACC AGGAGGGCAC AGCACAAACC TGAGCAGGTC TTTTATGTAT    120

GTGAAGGTGA AGGAGTTATG ATTTAGAAAT GGCAGTGGGA AGCAAGGAGA ATGCTGAGGG    180

CCTGCTCAGC TCTTGTCTTC CAGGATCATG GATAGTGCAA AATGAGTAGC CTTCATTTGA    240

GAGACAGAGC CATGAGGCTA GTGGAGTGCT CAGAAAGAAG CCAGATCTCT ATCAAGGAAA    300
```

```
GGAGATGGAG AGAACAACCA GGGATGTACT GAAAGGGGAG AGTTGCATGT CTCCAATGGA      360

ATATGTGTTG CAGAGGACTC AGTCACAGAG AAGACAACTC CAGGAGGG                  408
```

(2) INFORMATION FOR SEQ ID NO:112:

(i) SEQUENCE CHARACTERISTICS:
        (A) LENGTH: 254 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: G66.seq (xi) SEQUENCE DESCRIPTION: SEQ ID NO:112:

```
GGCGATCAAG AAGGATGCCC CCCAGGACAG TGACTCTGCT GGACTTCTCT ACAGAAAACA      60

GTATATCCCT CAGTGGCATG AGAAGATCCA ATAGGGTCAC CACACTCCAC AACTGCAGGG     120

GACACTGTTC ACATTTTAGT CTATGCAGCC TCTGGTGGCC AAAGATTAAT ATGAGAACAC     180

CTTTGCTGTG TGACCTGAAG TTCATGGGCA GTAAATTGTA GCTATTGTTA TGCACGACTT     240

TGGGCGAACC AGGG                                                      254
```

(2) INFORMATION FOR SEQ ID NO:113:

(i) SEQUENCE CHARACTERISTICS:
        (A) LENGTH: 345 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: H973.seq (xi) SEQUENCE DESCRIPTION: SEQ ID NO:113:

```
CACAGGAGGA TCACATAGGG TCACCACACT CCACAACTCC AGGAGATGCT GTTAACATTT      60

TAGTCTATGG ATCCTCTGGT GGCCTAAGAT TTAAATGAGA GCACTTTGT TATGTGACCT      120

GAAGTTAATG TCAATAAGTT ATAGCTATTG TTATGTACGA TGTAAGCAGG GGTCACTGCA     180

GGCCAGAAGG CTGACACAAT TTGGCCAGGC TTTGTTCTTC AAGGAAGGGC AGGGCTCTGA     240

GAAGTGCAGA CCGTGATGCA GGTGAAGGCC AGGAGGCAGG GACTCCCAGG GCAGGTCTGG     300

AAGGAGCGAG GCTGGTGACG GAAGTGGTCA GCAACCTCAA GGCGT                    345
```

(2) INFORMATION FOR SEQ ID NO:114:

(i) SEQUENCE CHARACTERISTICS:
        (A) LENGTH: 413 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO -continued

```
        (iv) ANTI-SENSE: NO (vi) ORIGINAL SOURCE:
             (C) INDIVIDUAL ISOLATE: H505.seq (xi) SEQUENCE DESCRIPTION: SEQ ID NO:114:

GGGAGATCTG CTGCTCTTTT CAGAGCCAGC AGGTAGGAAC ATTTAAGTCT GCTGAAGCTG         60

TGCCCACAGC CGCCCCTTTC CCCACGTGCT CTGTCCCAGG GAGATGGGAG TTTTATCTAT        120

AAGCCTCTGA CTTGGGCTGC TGCTGTTCTT TCAGAGGTGC CCTGCCCAGA GAGGAGGAAT        180

CTGGTGAGGC AGTCTGGCTA CAGAGGCTTT GCTGAGCTGC GGTGAGCTCT GCCCAGTTCC        240

AGCTTCCTCG TGGCATTGTA TACACTGTGA GGGGTAAACC ACGTACTCAA GCCTCAGTAA        300

TGGTGGATGT CCCTTCCCCC ACCAAGCTTG AGTGCCCCAG GTCTACTTCA GACTGCTGTG        360

CTGGCAGCAA GAATTTCAAA CCAGTGGATC TTAGCTTGCT GGGCTTCTTG GGG              413

(2) INFORMATION FOR SEQ ID NO:115:

(i) SEQUENCE CHARACTERISTICS:
            (A) LENGTH: 283 base pairs
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (vi) ORIGINAL SOURCE:
             (C) INDIVIDUAL ISOLATE: H989.seq (xi) SEQUENCE DESCRIPTION: SEQ ID NO:115:

GGTGCCTATG CCACCAGGGC CCTGGGTTTC AAGCATAAAA CGAAGTGGCC GGTTCACCAG         60

ACACCGAGCT AGCTACAAGA GTTTTTTTTC ATACCCCAGT GGCAGTGGAA CACCAGCGAC        120

ACAGAATCAT TTACTCCCCT GGAAAGGGGC TGAAGCCAAG AAACCAAAGG GGCTGGCTCA        180

GCGGATCCCA CTCCCATGGA GCCCAGCAAG CTAAGATCCA CTGGCTTGAA ATTCTCGCTG        240

CCAGCACAGC AGTCTGAAGT TGACCTGGGA TGCTCGAGCT TGG                         283

(2) INFORMATION FOR SEQ ID NO:116:

(i) SEQUENCE CHARACTERISTICS:
            (A) LENGTH: 768 base pairs
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (vi) ORIGINAL SOURCE:
             (C) INDIVIDUAL ISOLATE: E118con.seq (xi) SEQUENCE DESCRIPTION: SEQ ID NO:116:

TGCCTGGAAT TATTATATGC TCATCACTTT ATGAAGAATA AAATTTGTCT TTCCTGCCTT         60

AAAGTTACAT TCGTTCTTCC GCTCAAATCC TGATCTGGTC CATTAAAGAG TGTTCGCAGA        120

CAAAGTTTCT GAAAGATTAG AGAAGAATCC CCCCAAGAT TGCCCCAACA CTGAACTACA         180

GACAAACACT ATTTTATTTA AATAAGGAGA CAGCTTTCTA AAAGTATACA TTCTCTAATA       240
```

```
AAAATAGTTT ATTATTTTGA ATGATTTAAT GGTTTTCTAC ACAATTTACA TCACAACATG         300

TAAATTTTAG CAGTAACATC TGATTCTAAC AGCACATCAT GCTATTCCTT TCATAGAGCC         360

TTCAGAGATT CAATGCTAAA CAAATTTCCT TAGTTGGCAT CAAGGCACTG ATCACTTTAG         420

AGGCTTTTAA GAAATTATTT AAAGATGCAA ATGCCTCTGA GTGAAGTGTA CTATCCCATC         480

ACTGAAGCCC ACAGGAACAA GTCCTACAAT TTTAAAAAGG CTCGATGGAA AAATTTCTCA         540

ATCCTGAAAT CCCCTAGGGA AGGGGTCAGG AGAAAGTGCC ATGGTTGATA TTTAAGAACT         600

CCACAGCTCT TAAAAATAAG CACTTATCCC TAACATGCAA TACTGCAGAT GCAAGTTAAA         660

CTTATCTGTT AACAGCTGCC TGCTGTTTTC TGCTCCCAGA TGAAATGAAG CAACTCTTCT         720

GATAACGAAG AGATACCTGT CTGAGGCAAA CGAAACATTG GCACACAG                      768
```

(2) INFORMATION FOR SEQ ID NO:117:

(i) SEQUENCE CHARACTERISTICS:
        (A) LENGTH: 493 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: E69f.seq (xi) SEQUENCE DESCRIPTION: SEQ ID NO:117:

```
GGGTCATTTT TGCTGTCACC AGCAACGTTG CCACGACGAA CATCCTTGAC AGACACATTC          60

TTGACATTGA AGCCCACATT GTCCCCAGGA AGAGCTTCAC TCAAAGCTTC ATGGTGCATT         120

TCGACAGATC TCACTTCCGT TGTAACGTTG ACTGGAGCAA AGGTGACCAC CATACCGGGT         180

TTGAGAACAC CAGTCTCCAC TCGGCCAACA GGAACAGTAC CAATACCACC AATTTTGTAG         240

ACATCCTGGA GAGGCAGGCG CAAGGGCTTG TCAGTTGGAC GAGTTGGTGG TAGGATGCAG         300

TCCCAGAGCC TCAAGCAGGG TTGGGTTCCC ACTGGCATTG CCATCCCTTA CGGGTTGACT         360

TTCCATCCCC TTGGACCCAA GGCATTTTTA GCACTTGGGT TCCCAGCATG TTGTCACCAA         420

TCCCAACCAA GAATTTGGAA AAATTNTACT GNGTCGGGGT TGGTAGCCAA TTTCTTATGT         480

AGTGTGNTCC CTA                                                            493
```

(2) INFORMATION FOR SEQ ID NO:118:

(i) SEQUENCE CHARACTERISTICS:
        (A) LENGTH: 483 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: E69r.seq (xi) SEQUENCE DESCRIPTION: SEQ ID NO:118:

```
CAGCCAAATT CTACTGGAGG TACAAAGAGG AGTTGGTACC ATTCCTTCGG AAACTATTCC          60
```

```
AATCAATAGA AAAAGAGAGA ATCCTCCCTA ACTCATTTCA TGAGAACAGG ATCATCCTGA      120

TACTAAAGCC GGGCAGAGAC ACAACAAAAT NNGGAATTTT AAGCCAATAT CCCTGATGAA      180

CATCAATGCA AAAATCCTCA ATAAAATACT GGCAAACGAA ATCCAGCAGC ACATCAAAAA      240

GCTTATCCAC CATGGTCAGG CCGGGTTCAT CCCTGGGATT CAAGGCTGGT TCAACATATG      300

CAAATCAATA AATGTNATCC ATCACATNAA CAGAACCCAA CGNCAAAAAC CACATGATTA      360

TCTCAATAGA TTGTAGAAAA GGCCTCCGAC AAAAANTCAA CAACCCTTCA AGCTAAAANN      420

TCTCAATAAA CTATGTTTTG ATGACATATT CAAAATTATA GAGTATTTGA AACCACGGCA      480

TTA                                                                   483

(2) INFORMATION FOR SEQ ID NO:119:

(i) SEQUENCE CHARACTERISTICS:
        (A) LENGTH: 707 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: E36.seq (xi) SEQUENCE DESCRIPTION: SEQ ID NO:119:

CGAGGACCAA ACTCAGGACA CCGAGCTTGT GGAGACCAGA CCAGCAGGAG ATAGAACCTT       60

CCAGAAGTGG GCAGCTGTGG TGGTGCCTTC TGGAGAAGAG CAGAGATACA CATGCCATGT     120

ACAGCATGAG GGGCTGCCGA AGCCCCTCAC CCTGAGATGG GAGCCATCTT CNCAGTCCAC     180

CATCCCCATC GTGGGCATTG TTGCTGGACC TGGCTGTCCT AGCAGTTGTG TCATATCGGA     240

GCCTGTGGTC GCCACTGTGA TGTGTAGGAG GAAGAAGCTC AGTGGAATAA GGAGGGAGCC     300

AACTGTCAGG CTGCCGTGCC AGCGACAGTG CCCAGGGGCG CTGATGTGTC TCTCACAGCT     360

TGGGAAGCCT GAGGCAAGCT GTGCTTGTGA GGGGCTGAGA TGCAGGGATT TCTTGACGCC     420

TCCCCTTTGT GACTTCAAGA GCCTCTGGCA TCTCTTTCTG CAAAGGCACC TGAATGTGTC     480

TGCGTCCCTG TTAGCATAAT GTGAGGAGGT GGAGAGACAG CCCACCCTTG TGTCCACTGT     540

GACCCCTGTT CCCATGCTGA CCTGTGTTTC CTCCCCGTCN CTAATTAGAT GACGAGGCAT     600

TTGGCTACCT TAAGAGAGTC ATAGTTACTC CCGCCGTTTA CCCGCGCTTC ATTGAATTTC     660

TTCACTTTGA CATTCAGAGC ACTGGGCAGA AATCACATCG CCTCAAC                  707

(2) INFORMATION FOR SEQ ID NO:120:

(i) SEQUENCE CHARACTERISTICS:
        (A) LENGTH: 324 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: A104f.seq (xi) SEQUENCE DESCRIPTION: SEQ ID NO:120:
```

```
CATGAAGTCA CTGAGCCTGC TCCACCTCTT TCCTCTCCCA AGAGCTAAAA GAGAGCAAGG      60

AGGAAACAAC AGCAGCTCCA ACCAGGGCAG CCTTCCTGAG AAGATGCAAC CAATCCTGCT     120

TCTGCTGGCC TTCCTCCTGC TGCCCAGGGC AGATGCAGGG GAGATCATCG GGGACATGA     180

GGCCAAGCCC CACTCCCGCC CCTACATGGG TTATCTTATG ATCTGGGATC AGAAGTCTCT     240

GAAGAGGTGC GGTGGCTTCC TGATACAAGA CGACTTCGTG CTGACAGNTG CTCACTGTTG     300

GGGAAGCTCC ATAAATGTCA CCTA                                             324
```

(2) INFORMATION FOR SEQ ID NO:121:

(i) SEQUENCE CHARACTERISTICS:
        (A) LENGTH: 387 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: A104r.seq (xi) SEQUENCE DESCRIPTION: SEQ ID NO:121:

```
ACTACTACTA CTACTAACTC GAGAATTCTG GATCCTCGGC TTAGTTTGCT TCCTGTAGTT      60

AGTAGCGTTT CATGGTTTTC TTTATCCAGT GTACAAAGCT TGAGACTTTG GTGCAGGCTC     120

GTGGAGGCAT GCCATTGTTT CGTCCATAGG AGACAATGCC CTGGGCCACC TTTGTTACAC     180

ACAAGGAGGG CGCTCCAGAG TCCCCCTTAA AGGAAGTCTT TTNAATCTCT GGGTCCCCCA     240

CGCACAACTC AAGGGTACTG TCGNAATAAT GGCGTAAGTC AGATTCGCAC TTTTCGATCT     300

NCCTGCACTG TCATCTTCAC CTCTAGGTAG TGTGTGTGAG TTGTGATGCC CAGGGGGGGN     360

CCNNCTGNCC CCAGNCGGGN CANACTN                                          387
```

(2) INFORMATION FOR SEQ ID NO:122:

(i) SEQUENCE CHARACTERISTICS:
        (A) LENGTH: 562 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: H622.seq (xi) SEQUENCE DESCRIPTION: SEQ ID NO:122:

```
GGAACGTCTG AGGTTATCAA TAAGCTCCTA GTCCAGACGC CATGGGTCAT TTCACAGAGG      60

AGGACAAGGC TACTATCACA AGCCTGTGGG GCAAGGTGAA TGTGGAAGAT GCTGGAGGAG     120

AAACCCTGGG AAGGCTCCTG GTTGTCTACC CATGGACCAG AGGTTCTTTG ACAGATTTGG     180

CAACCTGTCC TCTGCCTCTG CCATCATGGG TAACCCAAAG TCAAGGCACA TGGCAAGAGG     240

GTGCTGACTT CCTTGGGAGA TGCCATAAAG CACCTGGATG ATCTCAAGGG CACCTTTGCC     300

CAGCTGAGTG AACTGCGCTG TGACAACCTG CATGTGGATC CTGAGAACTT CAAGCTCCTG     360
```

```
GGAAATGTGC TGGTGGCCGT TTTGGCAATC CATTTCGGCA AGAATTCAC  CCCTGAGGTG      420

CAGTCTTCCT GGCAGAAGAT GGTGACTGGA GTGGCCAGTG CCCTGTCCTC CAGATACCAC      480

TGAGCTCACT GCCCATGATG CAGAGCTTTC AAGGATAGGC TTTATTCTGC AAGCAATCAA      540

ATAATAAATC TATTCTGCTA AG                                               562
```

(2) INFORMATION FOR SEQ ID NO:123:

(i) SEQUENCE CHARACTERISTICS:
        (A) LENGTH: 692 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: G61con.seq (xi) SEQUENCE DESCRIPTION: SEQ ID NO:123:

```
GTGGGAGGTA GCCACCTGTT CTGGGCTGTG TCTGTCCTGC TGCCTGCTGG AGAGGCCAGC       60

AATGAGTCCT GGGCCAGCCC AGATCTCACC TGTGTGTTGA ATACTAAACA AGGAGACAAG      120

TAAAATAAGT CCAGCATGAG TCAGATGCTA GGTCTTGGCT TGGGGAAGCA TGCCCTCAAG      180

TGCCATAAAC ACCTAGAGGA CAAATGGGAG CAGAGGATCA AGAGCTTCTG CCTGCCTGTA      240

CAGCACCTTT GGTGCAAAGT AGGAAGAAGT CTCACTCTGG GTGGATAACT TTCTTAAAGG      300

CACACCTCCC TCTAGGCTAA GGCAGCCCCA TGCCGCAGGG TCTAATCTTG TCAATCAAAA      360

TACCCACCCA TCAGTGACAA TATGAGTGGC TTCTGCAGCA TTCAGGGGAA TTTTGTCAGA      420

GATAGGGAGG CCAAGATCCA AGTGGAGGAA GCCTGACTAG CAGAGTCTGT GGAAGAACTG      480

CAATGGGGGA TGAGTCTTCA GGGTCTTGTG CCTGAGCAAT GTGGGTTGTG GGAGAGGATT      540

CTGGAGAAGG TTTTATTTGG ATGGTAGAGG ATCCCTCCAT TTAGCTGCTG AGTCAAGAGG      600

AAGAGAGTGG AGTCCAGGAG GGTAGTAGGA GGTCGTTATG ATGTTATGGA TAAGAATAGA      660

TGTGGTCCAA GGATGGCTTG AGTCATGGCT GG                                    692
```

(2) INFORMATION FOR SEQ ID NO:124:

(i) SEQUENCE CHARACTERISTICS:
        (A) LENGTH: 289 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: G45.seq (xi) SEQUENCE DESCRIPTION: SEQ ID NO:124:

```
CCCAAGATAG GCCGGGGCAG GGAGAAGTAG GGATGGATGG GATCCCCACA GTGTGACATA       60

GCATGGCTGT GAATGAGGTG GGTGGGCGAG GGTGAGCCCC AGAAGCCAGG ACATCTGGAC      120

TCCAGCTAAG GGTGTGGAAA CAGGCTATGA AGATCGCCA  GGAGAAGTGA CTCATAGTTG      180

TCCCCACCTG ACTACTCCGT TGACTACACT CCTGGTGCTG GGAAAGGCCT CCCTGCCATC      240
```

CAGTCTTTCT CTCCTCTCTC CACTCTGCAG GAACAACTCC AGCCTCTAC                289

(2) INFORMATION FOR SEQ ID NO:125:

(i) SEQUENCE CHARACTERISTICS:
        (A) LENGTH: 1200 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: G3con.seq (xi) SEQUENCE DESCRIPTION: SEQ ID NO:125:

ATGTATGTTT GGCTCTGCTT TTAACTTTAT AAATCCAGTG ACCTCTCTCT CTGGGACTTG     60
GTTTCCCCAA CTAAAATTTG AAGTAGTTGA ATGGGGTCTC AAAGTTTGAC AGGAACCTTA    120
AGTAATCATC TAAGTCAGTA CCCACCACCT TCTTCTCCTA CATATCCCTT CCAGATGGTC    180
ATCCAGACTC AGAGCTCTCT CTACAGAGAG GGAAATCTCC ACTGTTGCAC ACCCACCTTT    240
GGAAAGCTCT GACCACTTGA GGCCTGATCT GCCCATCGTG AAGAAGCCTG TAACACTCCT    300
CTGCGTCTAT CCTGTGTAGC ATACTGGCTT CACCATCAAT CCTGATTCCT CTCTAAGTGG    360
GCATTGCCAT GTGGAAGGCA AGCCAGGCTC ACTCACAGAG TCAAGGCCTG CTCCCTGTAG    420
GGTCCAACCA GACCTGGAAG AACAGGCCTC TCCATTTGCT CTTCAGATGC CACTTCTAAG    480
AAAAGCCTAA TCACAGTTTT TCCTGGAATT GCCAGCTGAC ATCTTGAATC CTTCCATTCC    540
ACACAGAATG CAACCAAGTC ACACGCTTTT GAATTATGCT TTGTAGAGTT TTGTCATTCA    600
GAGTCAGCCA GGACCATACC GGGTCTTGAT TCAGTCACAT GGCATGGTTT TGTGCCATCT    660
GTAGCTATAA TGAGCATGTT TGCCTAGACA GCTTTTCTCA ACTGGGTCCA GAAGAGAATT    720
AAGCCCTAAG GTCCTAAGGC ATCTATCTGT GCTAGGTTAA ATGGTTGGCC CCAAAGATAG    780
ACAGGTCCTG ATTTCTAGAA CCCGTGACTG TTACTTTATA CAGCAAAGGG AAACTTTGCA    840
GATGTGATTA AAGCTAAGGA CCTTAAGACA GAGTATCCTG GGGGTGGTGG TGGGGTGGGG    900
GGGGGTCCTA AATGTAATCA CGAGTAAGAT TAAGAGCAAA TCAATTCTAG TCATATATTA    960
AACATCCACA ATAACCAAGA TATTTTTATC CCAAGAATGC AAGATTTCAG AAAATGAAAA   1020
ATCTGTTGAT AAATCCATCA CTATAATAAA ACCGAAGGTG AAAAAAATTC TGAAAAAATT   1080
CTAGCAGCTA TATTTGATAA AATTCAACAT CTCCTAGCTT TAGCAAACTC ACAGTTTTGC   1140
AAATAATATT TTCTTAATGT TATCTGTTGC TAAATCAAAA TTAAACAGTC ATCTTAACTG   1200

(2) INFORMATION FOR SEQ ID NO:126:

(i) SEQUENCE CHARACTERISTICS:
        (A) LENGTH: 319 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:

(C) INDIVIDUAL ISOLATE: G30.seq (xi) SEQUENCE DESCRIPTION: SEQ ID NO:126:

| | |
|---|---|
| ACGTGGTATG AAGTGTAAAG TTCTACTTTT AATTTTTTGC ATATTTTATT AGGATAGGAT | 60 |
| GGGCTTTTTC TGTAGTAATA ATCCCTAAAT CTCAGGGGCT TAATATATAA AATTGTCTCA | 120 |
| TGCAAAAAAC CACTGGGTCT AGGGCAATTG CTATCTACTG CCGTCTAATC TCCCTCTAGT | 180 |
| GGCTTCCATT GGTAGACCCT AACAGGAAGC CAGCTGATAA GGGAATCTGG GAAATGTAGT | 240 |
| TTACAGAGTG GCAGCTACAG TAGAACAGTA GAGACTACAA GGATGAGCTT GCAGCTGAGA | 300 |
| ATAGAAACGT GACTGGCAC | 319 |

(2) INFORMATION FOR SEQ ID NO:127:

(i) SEQUENCE CHARACTERISTICS:
        (A) LENGTH: 383 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: G32.seq (xi) SEQUENCE DESCRIPTION: SEQ ID NO:127:

| | |
|---|---|
| CAGAACTTGA ATCTCTTCTG TTAATGGCAA CTCCATTATT CCAATTGCTC AGGCAAAAAT | 60 |
| TGGCATTAAC CTTGATTCTT TATCTTACAT CTTTATATCTA ATTCGCCAGT TTAATACTAT | 120 |
| GGGTTCAATT TTCAAAACAT CCGGAATCTG ACCATGCCTC ACCATTTAAA CCAGCAGTCC | 180 |
| CCAACCATTT TGGCACCAGA GACCGATTTA GTGGAAGACA ATTTTTCCAT GGACGGGTGG | 240 |
| GGTGAGGGGG ATGGTTTCGG GATGAAACTG TTCCACCTCA GATCATCAGG CATTAGTCAG | 300 |
| ATTCTCATAA GGAGCATGCA ACCTAGATCC CTCACGTGCA AATTCACAAT AGAGTTTGCA | 360 |
| TTCCCGTGAG AATCTAATGC CAC | 383 |

(2) INFORMATION FOR SEQ ID NO:128:

(i) SEQUENCE CHARACTERISTICS:
        (A) LENGTH: 407 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: G37.seq (xi) SEQUENCE DESCRIPTION: SEQ ID NO:128:

| | |
|---|---|
| GGATAATGCA AAGGAAGACG CTGCCTGGGA ATTCACCGTC TGTGGAAATG AGTCCCAGAG | 60 |
| AGGAATAAAG CAGCCCTCAC CTTGCTCTCC CCACCCGAAC CCACTTTCCC CACCCGCCTC | 120 |
| GGCCCCCACC CCAACACCAC CATCACTCCC TTCCCTCCCT CTACTGCAAT CAGCTATTTT | 180 |
| CCATCATTCT TACCTCCCTC TCTTACACCA TTCTTCATAG AACAGCCTAT TGTATTTTTT | 240 |
| AAGAGACTGT GTTCCTCCTC CACTTCTGTT CAATGGCTTC ATATTCACTT AAATTAAAAT | 300 |

```
TCAAACGTTT ACCACGGCTT TCAATGACCT GAATGATGTG CCTGCTGCCC TCCTTTCCAA      360

TCTCACTTCA GGACTCCTAC CCTCTGGCTA TTAGGAGGCT GCAGCTG                   407

(2) INFORMATION FOR SEQ ID NO:129:

(i) SEQUENCE CHARACTERISTICS:
        (A) LENGTH: 428 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: G39.seq (xi) SEQUENCE DESCRIPTION: SEQ ID NO:129:

GGGTGGGGTA GGGGGAAGAG GTGGACATCA AAAAGGACCT GACTCCAAGA TGATATGCAA       60

TAATTAACCA TTGGAGGGCA GAAAGAGACT AAACACTTTT TTTTTCTTTT TAATGAATAA      120

TTGCTAATAC TCTGGAGATG AAATACTTCT AACTCCAAAT CTATTTGTGC TTTACATTTT     180

ACGTTTGGGG TTAGCTTTGT AAGGTGACAA GCCACCTTAG GTATAAGAAA CAATGATTTT     240

CCCAAATGCT GACTTTATGA AAGGCCTATT ACTCCCCCAG AGTATTTATT GTTAGAAGTA     300

ATGGTTAAAA TATATGATTG CCTAGAAAGG AAGTAAAAAA TGAAAATCTG AAACCCGTGG     360

TGAAAAGAGT GAGGCAGCTG TAACCTATTC CTCAACTTCT GAGTGTTAAC AGGGCCCGTG     420

TGGGGTTG                                                            428

(2) INFORMATION FOR SEQ ID NO:130:

(i) SEQUENCE CHARACTERISTICS:
        (A) LENGTH: 435 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: G75.seq (xi) SEQUENCE DESCRIPTION: SEQ ID NO:130:

GAATTCTGGA TCCTCCCTCA GTGGGTCCCT CTCAAGAGGC CATTTAAAAA CCTGGACTGA      60

TAGAAACAGC CAGTACTTTG TGCCTCCTGC ATCCCATGTT GGAGACAATT GCCCTAACCA     120

CCCAGAGCAT TGCTCAGCCT ATAAACCCAT TTCCAAGGAT AGGGCCTGAC TTCTTTGAGG     180

ATCATGAGTA TGATTTCCAG GTCTTTTCTG ACCTCATTAA TGACCTTCCT GCTATGCACT     240

GGTCTCTAAA CCCCTTGGCC GTGATTGTGA TGTGGAAATA AATAGAAGGT GCTTTATTCT     300

TAAGCAGAGA TTCAGTGGCA GAGGGTTTGA TTTTGGAAAA GAGAAAGGGC GCAGGATCAA     360

GTGAGAATCT TGTAGAATTG TGAGGCCAGA GGAGCTTTCT CCTACCTTCA TGACCTTGTT     420

GAGGATCCAG AATTC                                                    435

(2) INFORMATION FOR SEQ ID NO:131:
```

(i) SEQUENCE CHARACTERISTICS:
    (A) LENGTH: 373 base pairs
    (B) TYPE: nucleic acid
    (C) STRANDEDNESS: double
    (D) TOPOLOGY: linear (ii) MOLECULE TYPE: cDNA to mRNA (iii) HYPOTHETICAL: NO (iv) ANTI-SENSE: NO (vi) ORIGINAL SOURCE:
    (C) INDIVIDUAL ISOLATE: H100.seq (xi) SEQUENCE DESCRIPTION: SEQ ID NO:131:

```
CCCCATCCTG CCCGCTGCTA CCAGCTACAC CTCCGTTGCC CAGGCCCTGG GATCAAACCC      60

TGCCCACCAG CTCCCCTCGT CCAACCAGCT GCCACGTCCT GTAACCAAAA GTGACCGGGA     120

TGAATGCCTG GCTCCCCCTC CTTTCCAGCC CTAGCTCAGG CCCATCGTCC CCAGCTGATG     180

TCGCCCTGTC TGCACGATGC CTGGGCACCT ACTCCACACT CCTCACTGGC CTCAGGCCCC     240

ACCAGCCCCT GCCTCGAGCT AGCCCCTCCA CCCGTCATCA CTCCTGCCAG ACTCCAGATG     300

TCCAAGGTGC TCCTTGGCTC CCACAAGCTC TCCTCCAGCA CCCCATCTTC CCCTGGTTGC     360

CCCTCGGTTC CCC                                                        373
```

(2) INFORMATION FOR SEQ ID NO:132:

(i) SEQUENCE CHARACTERISTICS:
        (A) LENGTH: 312 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: H414f.seq (xi) SEQUENCE DESCRIPTION: SEQ ID NO:132:

```
GATCCATATC TGGGGAAGA GGATTCTATG CTTGACTGAA TATGGGATGT GAAGGAGAAG       60

AAGTTGTGGC CTCAATCTAC CCAATTGGGA GACTGGTGCA TGGGCCATGG TAGTGCCAAA    120

ACATAGAGCT ATTAAGGTAA GGAATGCAGG AGGGAAGAGT AGGCATGGTG GAGAAGATAG    180

AGAAATCTAG TTGTACTTAG TAAGTTTGAG GTAGGCTGAA ATTCAGGTAA CAGTTTTCTT    240

AGTAGGCAAT TGGGGTGAGA GATTTTGGAA ATTTACCCTT TAGATCAATT TTTGGGGAGG    300

ATCCAAGAAT CT                                                        312
```

(2) INFORMATION FOR SEQ ID NO:133:

(i) SEQUENCE CHARACTERISTICS:
        (A) LENGTH: 503 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
    (C) INDIVIDUAL ISOLATE: H631.seq (xi) SEQUENCE DESCRIPTION: SEQ ID NO:133:

```
CAGAAATGAG CAAAGGCAAA GGGGAATACA GTGGGTCTGA GGCTGGCTCA CTGTCCCATT    60

CTGAGCAGAA TGCCACTGTT CCAGCTCCCA GGGTGCTGGA GTTTGACCAC TTGCCAGATC   120

CTCAGGAGGG CCCAGGGTCA GATACTGGAA CGCAGCAGGA AGGAGTCCTG AAGGATCTGA   180

GGACTGTGAT TCCATACCGG GAGTCTGAAA CACAAGCAGT CCCTCTTCCC CTTCCCAAGA   240

GGGTAGAAAT CATTGAATAT ACCCACATAG TTACATCACC CAATCACACT GGGCCAGGGA   300

GTGAAATAGC CACCAGTGAG AAGAGCGGAG AGCAAGGGCT GAGGAAAGTG AACATGGAAA   360

AATCTGTCAC TGTGCTCTGC ACACTGGATG AAAATCTAAA CAGGACTCTG GACCCCAACC   420

AGGTTTCTCT GCACCCCCAA GTGCTACCTC TGCCTCATTC TTCCTCCCCT GAGCACAACA   480

GACCCACTGA CCATCCAACC TCC                                          503
```

(2) INFORMATION FOR SEQ ID NO:134:

(i) SEQUENCE CHARACTERISTICS:
        (A) LENGTH: 398 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: G93.seq (xi) SEQUENCE DESCRIPTION: SEQ ID NO:134:

```
CCCTCCTATC TTCTTTCTCA TCCCTGCCTC CCTCCCATGC TGACTCCTGT GTCCCTCCCT    60

TCAGTCACTC TCCTGTCAAG TGGCTCACCT CTTGGGCCTC CCCAAGGATC CCATTCTGAA   120

AACCCCACCA AGGCAATCCA GTTGACGACC TTCCTGCTCC CTCCACAGCG CAGCCCCCGA   180

GGATCACAGT CTCTGTCCCA GAGGGGCTCT CTTCCCAGAA ACTGTCAACA CATGCCCCCT   240

TTAGACTCCT CTCATCCTCA GCCAGGACTC TGACTCCCAT TCCACAAAGG AGGCAGAAGC   300

CGTCAGAGGA CTCCCCGCAT CTTCCTGGCC TCCCAGACTC TTCTCTTACC CCTTCCTTCC   360

TAGCAGGGCC ATCTCCTCCC TGGTACTTGG AGACCTCC                           398
```

(2) INFORMATION FOR SEQ ID NO:135:

(i) SEQUENCE CHARACTERISTICS:
        (A) LENGTH: 629 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: G115a.seq (xi) SEQUENCE DESCRIPTION: SEQ ID NO:135:

```
CCTTTTTTTT TTTTAGGGGA AGCCAATTTG ATGATGTAGC TTGTGACTCC CAGGGTATTG    60
```

```
TCTACCCCAM CCTGGGGGAA AACATGGGGA AGTTTCTGGG ATCTAAGCTT CAATCGCAAG      120

CATCACAGGG GATTTTGAAA GTGATGCAGC ATCGTGAAAT GAGCATAGGG GATCGTTTGG      180

AGTCGAGCGC TTGTTATTTG AAGCTCCTCC TGTCTATGTG GTGACTCAAG GAGGGGAGAA      240

TTTCCCCTTT GTGAGCCAGC TGGACAAGTG TCAGCACTGC TGTCTTTGCA GGCTCTGGCA      300

CAGAGGCGCA GGGCCTGGAC TAAAGGGAGT CTCCAGGGTT TGGGGGTCAG ACCCAGCTTA      360

ACACACATGA AAAGGAGTGA TCTTTCTCTT AAGCCATTGA GCCAGGGTCC CCCTACAGCC      420

CACAGAGCCC TTTCCACCAC CTGGCGCAGC ATCTGAACCA AACAGAGGGC ATGTTTGTTG      480

CACTGCCTGG GGGTTCAGCT CCCATCCATA CCACAACACA GGACAAGGCC CGGGCTTTGC      540

ACAGCACAGT CAAGTGAGCA CACTCTCACG ATCTGATGCA GTCCTTCTCC CACACCCACC      600

ATCCAATTTT TTCCGAGGAT CCAGAATTC                                       629

(2) INFORMATION FOR SEQ ID NO:136:

(i) SEQUENCE CHARACTERISTICS:
        (A) LENGTH: 696 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
         (C) INDIVIDUAL ISOLATE: G115b.seq (xi) SEQUENCE DESCRIPTION: SEQ ID NO:136:

GTGGCACATG GAAAAAGTGG TGGTGAGGGG CAAGGAACAG GGACAAAAAA GGAACCTGGG       60

TCCTTAAGAG ATCACTTAGT TGTTTTACCC AAGACTTGGC RTACAAAAAA TATCAGAAAT      120

GAGTGTCTGC TGCCAAGTGG GGTCACTGCA CGTCCTAGAA AAAAGTATG CCTTCATCTG       180

CAGTGACACA CAGCCATGGT GTTGGGACTG GCACACTGCA TCTCTAAGCC GCCAAGAGCT      240

TGACCCTGGA TGGGAAGAAA ACTGCCCCAG AGATGCTGGA GCTGGCTTTA TGAACTGGCT      300

TTATGCTGGG GAGGTGGATG GCAGATCGCA TCCATCTGGT AGGTTGAGGT CCTCTTGGCA      360

AGCCTACTAC CATCACCTCC CAGCAGAAGA GGACTGCAAA CTATCCTTAA AGGGGACTCG      420

GTCCAGTGAG TCTTACCTTT TTTTGAGGTC ATACACCCCT TCCGGAATCT GATGGCACAC      480

ATAGACCCTT TCCCCAGGAA AATTCACAAA CATCCAGAGT TTCATATGCC ACTAGGGGAT      540

TTAAAAGACC CTGCATCAAC TGAACTCATA ACCTGGAGTC CAATTCTTAT GAGAGGGTGG      600

CACATGGAAA AAGTGGTGGT GAGGGCAAG GAACAGGGAC AAAAAAGGAA CCTGGGTCCT       660

TAAGAGATCA CTTAGTTGTT TTACCCAAGA CTTGGC                                696

(2) INFORMATION FOR SEQ ID NO:137:

(i) SEQUENCE CHARACTERISTICS:
        (A) LENGTH: 574 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO
```

(vi) ORIGINAL SOURCE:
                (C) INDIVIDUAL ISOLATE: G115c.seq (xi) SEQUENCE DESCRIPTION: SEQ ID NO:137:

GGAGGCCCCA GACTGCTACT CATACAGGCA GCTGTATCTT GTCTCCAGGA GAGAGCAGGG     60

ACCCAGKATG GAGCAGACAT AGGTCTTCTG GGGACTCAGC CCTTTCGGGA GGGAGTGTGT    120

GCCCTAGGCA CACCCTTCCC ATTTGACAAT CTGATATGAG GTGGAAACAG GGTCCTTGGG    180

CCCCTAAGTC ATGTTGGGAA TGTTTCCTTC TCTCAAGCCG GAAGAGCTGA GGTTTATCTG    240

AGAAATGCCT ATGTCTCTTT TGACACATCG TAGTCACTAA CCCCTTGTTC CTGCTCCAGG    300

AGCCTCTAAA AAGCCATCTA GACCAGAAAA ATTGGTCTTT TTTTAGTGAT GGGAGTGGCT    360

TTAATGTCAT TCTCCCCTAT TTAGTTATGA GCTGTACCTC AGTTTTGGTC ATTAGAAATA    420

TAATTTTAGG TCAGGTGCAG CGGCTCATGC CTATAATCCC ACACTTTGGG AGGCTGAGGG    480

TGGGCAGGTT ACTTGGAGGT CAGGAGGTTA AGACCAGCC TGGCAACATG GTGGAAACCC     540

TATCTCCACT TAAAATACAA AAATTAGTTG CATG                                574

(2) INFORMATION FOR SEQ ID NO:138:

(i) SEQUENCE CHARACTERISTICS:
            (A) LENGTH: 252 base pairs
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (vi) ORIGINAL SOURCE:
            (C) INDIVIDUAL ISOLATE: G122.seq (xi) SEQUENCE DESCRIPTION: SEQ ID NO:138:

GCTCTGACTA GCCAATGAGT CTTGCTCTGA TATGGCACCT GCAAAATCTC TTTCTGGGGT     60

CTTCCACTGC CTAACTTTAG CCCCAGTAAT TTACTAGGTT CTGGCACATG GCCCATGATC    120

CTGACACCAG GCCTGCCTTT GTTTCAGCTT CACTATTCTA ATCTTTGCAT TAATAGCTTG    180

TAATACCCTG GTGGCTATCA TTATATAGTG TATATGTGCA ATATCAGTAT GGCTGACCTA    240

GGTCAGTCCT GT                                                        252

(2) INFORMATION FOR SEQ ID NO:139:

(i) SEQUENCE CHARACTERISTICS:
            (A) LENGTH: 278 base pairs
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (vi) ORIGINAL SOURCE:
            (C) INDIVIDUAL ISOLATE: G329f.seq (xi) SEQUENCE DESCRIPTION: SEQ ID NO:139:

GTTGATCGGT GATGCCGCAA AGAATCAAGT TGCAATGAAC CCCACCAACA CAGTTTTTGA     60

TGCCAAACGT CTGATTGGAC GCAGATTTGA TGATGCTGTT GTCCAGTCTA ATATGAAACA    120

```
TTGGCCCTTT ATGGTGGTGA ATGATGCTGG CAGGCCCAAG GTCCAAGTAG AATACAAGGG      180

AGAGACCAAA AGCTTCTATC CAGAGGAGGT GTCTTCTATG GTTCTGACAA AGATGAAGGA      240

AATTGCAGAA GTCTACCTTG GGAAGACTGT TACCAATG                              278
```

(2) INFORMATION FOR SEQ ID NO:140:

(i) SEQUENCE CHARACTERISTICS:
        (A) LENGTH: 795 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: E67.seq (xi) SEQUENCE DESCRIPTION: SEQ ID NO:140:

```
GCGCGGGGTG GACTCTTTCT GGATGTTGTA GTCAGACAGG GTGCGTCCAT CTTCCAGCTG       60

TTTCCCAGCA AAGATCAACC TCTGCTGGTC AGGAGGGATG CCTTCCTTGN CTTGGGTCTT      120

TGNCTTGACA TTCTCAATGG TGTCACTCGG TTCCACTTCG AGAGTGATGG TCTTACCAGC      180

CAGGGTCTTC ACGAAGGATC TGCATCCCAC CTCTAAGACG GAGCACCAGG TGCAGGGTGG      240

GGACTCTTTT CTGGATGTTG TAGACAGACA GGGTGCGTCC ATCTTCCAGG TGTTTCCCAG      300

GAAAGGTCAA ACTCTGCTGA TCAAGAGGAT GCTCCTTGTC TGGATCTTTG CCTTGACATC      360

TCAATGGTGT CACTCGGCTC CACCTCGAGA GTGATGGTCT TACCAATCAG GTCTTCNCG       420

GAAGATCTNC ATCCCACCTC TGAGTCGGAG CACGCAGGTG CAAGGTGGAC TCTTTCTGGA      480

TGTTGTAGTC AGACAGGGTA CCGACCATCT TCCACCTGTT TTCCGGCAAA GATCAACCTC      540

TGCTGGTCAG GAGGGATCCC TTCCTTGTCT TGGAGCTTTG CCTTGACATT CTCAATGGTG      600

TCACTCGGCT CCACTTCGAG GGTGATGGTC TTACCANTNA GGGTCTTCAC GAAGAACTGC      660

ATACCCCCTC TGAGANGGAC CACCAGGTGC AGGGNAGACT CTTTCTGGAT GTTGTAGTCA      720

GANAGGGTGC GCCCATCTTC CAGCTGCTTT CCGGCAAAGA TCAACCTCTC CTGGTCAGGA      780

GGAATGCCTT CCTTG                                                      795
```

(2) INFORMATION FOR SEQ ID NO:141:

(i) SEQUENCE CHARACTERISTICS:
        (A) LENGTH: 565 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: E94.seq (xi) SEQUENCE DESCRIPTION: SEQ ID NO:141:

```
GTCACTGTAG AAGTATTTTA ATGTGTCAAA ACTTCCATCT GCATGTTTCT TTAATTTGCA       60

GAGGATTGAT TATTAGCTCT TTGTGCCAAA TAACTGTCAC TCATTTTAAA ATCTTTCCCA      120

AACACAGGTA CTATTTCTAT TCTACATAAT GGGAGAATGT GCCAGTAGGA GACTGCCTGG      180
```

-continued

```
CCAACTCTGA AAAAAATGCT TTAACAATAT GCCCCAGCTA AAATCACTTT TCCTTTATTT      240

CCACAAATCA AATTCAAAAT CAAAACTCAT TATGGTATAC CTTATATAAC TCGGATCATG      300

TTTATAAAAT TAGCATTCTT TGGATAGTAA AACACCAGTT AATACTTAAT TTGTTTACCC      360

ATGCACAAAA CTACCTCCCG AGATTAGACT AAGTCCCTTT AAGGATTTTA GGTCTCCATT      420

TTGAGNTGTT TTGATTTATA GAAGGATCTG AAAAAAAATC GAGGAGAAGT CGTTTTCCTC      480

CTTTGTAAAC CTTCTGCCCA GAGGCCGGCG ACGNATGCAC CAGCAAGGAC AAGCCCAGTC      540

TTTTCAAGCG ACACCTGTTC GCCTG                                            565
```

(2) INFORMATION FOR SEQ ID NO:142:

(i) SEQUENCE CHARACTERISTICS:
        (A) LENGTH: 420 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (vi) ORIGINAL SOURCE:
        (C) INDIVIDUAL ISOLATE: CDC.pep (xi) SEQUENCE DESCRIPTION: SEQ ID NO:142:

```
Met Ala Ala Thr Asp Leu Glu Arg Phe Ser Asn Ala Glu Pro Glu Pro
1               5                   10                  15

Arg Ser Leu Ser Leu Gly Gly His Val Gly Phe Asp Ser Leu Pro Asp
                20                  25                  30

Gln Leu Val Ser Lys Ser Val Thr Gln Gly Phe Ser Phe Asn Ile Leu
            35                  40                  45

Cys Val Gly Glu Thr Gly Ile Gly Lys Ser Thr Leu Met Asn Thr Leu
        50                  55                  60

Phe Asn Thr Thr Phe Glu Thr Glu Glu Ala Ser His His Glu Ala Cys
65                  70                  75                  80

Val Arg Leu Arg Pro Gln Thr Tyr Asp Leu Gln Glu Ser Asn Val Gln
                85                  90                  95

Leu Lys Leu Thr Ile Val Asp Ala Val Gly Phe Gly Asp Gln Ile Asn
            100                 105                 110

Lys Asp Glu Ser Tyr Arg Pro Ile Val Asp Tyr Ile Asp Ala Gln Phe
        115                 120                 125

Glu Asn Tyr Leu Gln Glu Glu Leu Lys Ile Arg Arg Ser Leu Phe Asp
    130                 135                 140

Tyr His Asp Thr Arg Ser Thr Val Trp Leu Tyr Phe Ile Thr Pro Thr
145                 150                 155                 160

Gly His Ser Leu Lys Ser Leu Asp Leu Val Ala Met Lys Lys Leu Asp
                165                 170                 175

Ser Lys Val Asn Ile Ile Pro Ile Ile Ala Lys Ala Asp Thr Ile Ser
            180                 185                 190

Lys Ser Glu Leu His Lys Phe Lys Ile Lys Ile Met Gly Glu Leu Val
        195                 200                 205

Ser Asn Gly Val Gln Ile Tyr Gln Phe Pro Thr Asp Asp Glu Ala Val
    210                 215                 220

Ala Glu Ile Asn Val Val Met Asn Ala His Leu Pro Phe Ala Val Val
225                 230                 235                 240
```

```
Gly Ser Thr Glu Glu Val Lys Val Gly Asn Lys Leu Val Arg Ala Arg
                245                 250                 255

Gln Tyr Pro Trp Gly Val Val Gln Val Glu Asn Glu Asn His Cys Asp
            260                 265                 270

Phe Val Lys Leu Arg Glu Met Leu Ile Arg Val Asn Met Glu Asp Leu
        275                 280                 285

Arg Glu Gln Thr His Ser Arg His Tyr Glu Leu Tyr Arg Arg Cys Lys
    290                 295                 300

Leu Glu Glu Met Gly Phe Gln Asp Ser Asp Gly Asp Ser Gln Pro Phe
305                 310                 315                 320

Ser Leu Gln Glu Thr Tyr Glu Ala Lys Arg Lys Glu Phe Leu Ser Glu
                325                 330                 335

Leu Gln Arg Lys Glu Glu Met Arg Gln Met Phe Val Asn Lys Val
                340                 345                 350

Lys Glu Thr Glu Leu Glu Leu Lys Glu Lys Glu Arg Glu Leu His Glu
                355                 360                 365

Lys Phe Glu His Leu Lys Arg Val His Gln Glu Lys Arg Lys Val
        370                 375                 380

Glu Glu Lys Arg Arg Glu Leu Glu Glu Thr Asn Ala Phe Asn Arg
385                 390                 395                 400

Arg Lys Ala Gly Trp Glu Ala Cys Ser Arg Pro Cys Thr Pro Pro
                405                 410                 415

Arg Ser Ser Pro
            420

(2) INFORMATION FOR SEQ ID NO:143:

(i) SEQUENCE CHARACTERISTICS:
        (A) LENGTH: 321 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (vi) ORIGINAL SOURCE:
        (C) INDIVIDUAL ISOLATE: Septin-2.pep (xi) SEQUENCE DESCRIPTION: SEQ ID NO:143:

Met Ala Ala Thr Asp Leu Glu Arg Phe Ser Asn Ala Glu Pro Glu Pro
1               5                   10                  15

Arg Ser Leu Ser Leu Gly Gly His Val Gly Phe Asp Ser Leu Pro Asp
                20                  25                  30

Gln Leu Val Ser Lys Ser Val Thr Gln Gly Phe Ser Phe Asn Ile Leu
            35                  40                  45

Cys Val Gly Glu Thr Gly Ile Gly Lys Ser Thr Leu Met Asn Thr Leu
        50                  55                  60

Phe Asn Thr Thr Phe Glu Thr Glu Glu Ala Ser His His Glu Ala Cys
65                  70                  75                  80

Val Arg Leu Arg Pro Gln Thr Tyr Asp Leu Gln Glu Ser Asn Val Gln
                85                  90                  95

Leu Lys Leu Thr Ile Val Asp Ala Val Gly Phe Gly Asp Gln Ile Asn
            100                 105                 110

Lys Asp Glu Ser Tyr Arg Pro Ile Val Asp Tyr Ile Asp Ala Gln Phe
```

```
                115                 120                   125
Glu Asn Tyr Leu Gln Glu Leu Lys Ile Arg Arg Ser Leu Phe Asp
    130                 135                 140

Tyr His Asp Thr Arg Ser Thr Val Trp Leu Tyr Phe Ile Thr Pro Thr
145                 150                 155                 160

Gly His Ser Leu Lys Ser Leu Asp Leu Val Ala Met Lys Lys Leu Asp
                165                 170                 175

Ser Lys Val Asn Ile Ile Pro Ile Ala Lys Ala Asp Thr Ile Ser
            180                 185                 190

Lys Ser Glu Leu His Lys Phe Lys Ile Lys Ile Met Gly Glu Leu Val
        195                 200                 205

Ser Asn Gly Val Gln Ile Tyr Gln Phe Pro Thr Asp Asp Glu Ala Val
    210                 215                 220

Ala Glu Ile Asn Val Val Met Asn Ala His Leu Pro Phe Ala Val Val
225                 230                 235                 240

Gly Ser Thr Glu Glu Val Lys Val Gly Asn Lys Leu Val Arg Ala Arg
                245                 250                 255

Gln Tyr Pro Trp Gly Val Val Gln Val Glu Asn Glu Asn His Cys Asp
                260                 265                 270

Phe Val Lys Leu Arg Glu Met Leu Ile Arg Val Asn Met Glu Asp Leu
            275                 280                 285

Arg Glu Gln Thr His Ser Arg His Tyr Glu Leu Tyr Arg Arg Cys Lys
    290                 295                 300

Leu Glu Glu Met Gly Phe Gln Asp Ser Asp Gly Asp Ser Gln Pro Phe
305                 310                 315                 320

Arg (2) INFORMATION FOR SEQ ID NO:144:

(i) SEQUENCE CHARACTERISTICS:
        (A) LENGTH: 645 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (vi) ORIGINAL SOURCE:
         (C) INDIVIDUAL ISOLATE: G18.pep (xi) SEQUENCE DESCRIPTION: SEQ ID NO:144:

Met Ser Arg Ile Glu Lys Met Ser Ile Leu Gly Val Arg Ser Phe Gly
1               5                   10                  15

Ile Glu Asp Lys Asp Lys Gln Ile Ile Thr Phe Phe Ser Pro Leu Thr
                20                  25                  30

Ile Leu Val Gly Pro Asn Gly Ala Gly Lys Thr Thr Ile Ile Glu Cys
            35                  40                  45

Leu Lys Tyr Ile Cys Thr Gly Asp Phe Pro Pro Gly Thr Lys Gly Asn
    50                  55                  60

Thr Phe Val Asn Asp Pro Lys Val Ala Gln Glu Thr Asp Val Arg Ala
65                  70                  75                  80

Gln Ile Arg Leu Gln Phe Arg Asp Val Asn Gly Glu Leu Ile Ala Val
                85                  90                  95

Gln Arg Ser Met Val Cys Thr Gln Lys Ser Lys Lys Thr Glu Phe Lys
```

-continued

```
                100                 105                 110
Thr Leu Glu Gly Val Ile Thr Arg Thr Lys His Gly Glu Lys Val Ser
            115                 120                 125
Leu Ser Ser Lys Cys Ala Glu Ile Asp Arg Glu Met Ile Ser Ser Leu
            130                 135                 140
Gly Val Ser Lys Ala Val Leu Asn Asn Val Ile Phe Cys His Gln Glu
145                 150                 155                 160
Asp Ser Asn Trp Pro Leu Ser Glu Gly Lys Ala Leu Lys Gln Lys Phe
                165                 170                 175
Asp Glu Ile Phe Ser Ala Thr Arg Tyr Ile Lys Ala Leu Glu Thr Leu
                180                 185                 190
Arg Gln Val Arg Gln Thr Gln Gly Gln Lys Val Lys Glu Tyr Gln Met
            195                 200                 205
Glu Leu Lys Tyr Leu Lys Gln Tyr Lys Glu Lys Ala Cys Glu Ile Arg
            210                 215                 220
Asp Gln Ile Thr Ser Lys Glu Ala Gln Leu Thr Ser Ser Lys Glu Ile
225                 230                 235                 240
Val Lys Ser Tyr Glu Asn Glu Leu Asp Pro Leu Lys Asn Arg Leu Lys
                245                 250                 255
Glu Ile Glu His Asn Leu Ser Lys Ile Met Lys Leu Asp Asn Glu Ile
            260                 265                 270
Lys Ala Leu Asp Ser Arg Lys Lys Gln Met Glu Lys Asp Asn Ser Glu
            275                 280                 285
Leu Glu Glu Lys Met Glu Lys Val Phe Gln Gly Thr Asp Glu Gln Leu
            290                 295                 300
Asn Asp Leu Tyr His Asn His Gln Arg Thr Val Arg Glu Lys Glu Arg
305                 310                 315                 320
Lys Leu Val Asp Cys His Arg Glu Leu Glu Lys Leu Asn Lys Glu Ser
                325                 330                 335
Arg Leu Leu Asn Gln Glu Lys Ser Glu Leu Leu Val Glu Gln Gly Arg
                340                 345                 350
Leu Gln Leu Gln Ala Asp Arg His Gln Glu His Ile Arg Ala Arg Asp
            355                 360                 365
Ser Leu Ile Gln Ser Leu Ala Thr Gln Leu Glu Leu Asp Gly Phe Glu
            370                 375                 380
Arg Gly Pro Phe Ser Glu Arg Gln Ile Lys Asn Phe His Lys Leu Val
385                 390                 395                 400
Arg Glu Arg Gln Glu Gly Glu Ala Lys Thr Ala Asn Gln Leu Met Asn
                405                 410                 415
Asp Phe Ala Glu Lys Glu Thr Leu Lys Gln Lys Gln Ile Asp Glu Ile
                420                 425                 430
Arg Asp Lys Lys Thr Gly Leu Gly Arg Ile Ile Glu Leu Lys Ser Glu
            435                 440                 445
Ile Leu Ser Lys Lys Gln Asn Glu Leu Lys Asn Val Lys Tyr Glu Leu
            450                 455                 460
Gln Gln Leu Glu Gly Ser Ser Asp Arg Ile Leu Glu Leu Asp Gln Glu
465                 470                 475                 480
Leu Ile Lys Ala Glu Arg Glu Leu Ser Lys Ala Glu Lys Asn Ser Asn
                485                 490                 495
Val Glu Thr Leu Lys Met Glu Val Ile Ser Leu Gln Asn Glu Lys Ala
                500                 505                 510
Asp Leu Asp Arg Thr Leu Arg Lys Leu Asp Gln Glu Met Glu Gln Leu
            515                 520                 525
```

-continued

```
Asn His His Thr Thr Thr Arg Thr Gln Met Glu Met Leu Thr Lys Asp
        530                 535                 540
Lys Ala Asp Lys Asp Glu Gln Ile Arg Lys Ile Lys Ser Arg His Ser
545                 550                 555                 560
Asp Glu Leu Thr Ser Leu Leu Gly Tyr Phe Pro Asn Lys Lys Gln Leu
                565                 570                 575
Glu Asp Trp Leu His Ser Lys Ser Lys Glu Ile Asn Gln Thr Arg Asp
                580                 585                 590
Arg Leu Ala Lys Leu Lys Ile Val Leu Lys Pro His Ser Ile Thr
                595                 600                 605
Ser Cys Tyr Asn Ser Leu Lys Lys Cys Phe Arg Asn Leu Ile Pro Leu
        610                 615                 620
Ile Glu Glu Val Leu Leu Leu Ser Ala Ala Asp Leu Glu Ala Val Ile
625                 630                 635                 640
Trp Ala Ser Ile Lys
                645

(2) INFORMATION FOR SEQ ID NO:145:

(i) SEQUENCE CHARACTERISTICS:
        (A) LENGTH: 527 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (vi) ORIGINAL SOURCE:
        (C) INDIVIDUAL ISOLATE: G65.pep (xi) SEQUENCE DESCRIPTION: SEQ ID NO:145:

Met Lys Leu Trp Val Ser Ala Leu Leu Met Ala Trp Phe Gly Val Leu
1               5                   10                  15
Ser Cys Val Gln Ala Glu Phe Phe Thr Ser Ile Gly His Met Thr Asp
                20                  25                  30
Leu Ile Tyr Ala Glu Lys Glu Leu Val Gln Ser Leu Lys Glu Tyr Ile
            35                  40                  45
Leu Val Glu Glu Ala Lys Leu Ser Lys Ile Lys Ser Trp Ala Asn Lys
50                  55                  60
Met Glu Ala Leu Thr Ser Lys Ser Ala Ala Asp Ala Glu Gly Tyr Leu
65                  70                  75                  80
Ala His Pro Val Asn Ala Tyr Lys Leu Val Lys Arg Leu Asn Thr Asp
                85                  90                  95
Trp Pro Ala Leu Glu Asp Leu Val Leu Gln Asp Ser Ala Ala Gly Phe
                100                 105                 110
Ile Ala Asn Leu Ser Val Gln Arg Gln Phe Phe Pro Thr Asp Glu Asp
                115                 120                 125
Glu Ile Gly Ala Ala Lys Ala Leu Met Arg Leu Gln Asp Thr Tyr Arg
    130                 135                 140
Leu Asp Pro Gly Thr Ile Ser Arg Gly Glu Leu Pro Gly Thr Lys Tyr
145                 150                 155                 160
Gln Ala Met Leu Ser Val Asp Asp Cys Phe Gly Met Gly Arg Ser Ala
                165                 170                 175
Tyr Asn Glu Gly Asp Tyr Tyr His Thr Val Leu Trp Met Glu Gln Val
```

-continued

```
                180              185              190
Leu Lys Gln Leu Asp Ala Gly Glu Glu Ala Thr Thr Thr Lys Ser Gln
                195              200              205
Val Leu Asp Tyr Leu Ser Tyr Ala Val Phe Gln Leu Gly Asp Leu His
210              215              220
Arg Ala Leu Glu Leu Thr Arg Arg Leu Leu Ser Leu Asp Pro Ser His
225              230              235              240
Glu Arg Ala Gly Gly Asn Leu Arg Tyr Phe Glu Gln Leu Leu Glu Glu
                245              250              255
Glu Arg Glu Lys Thr Leu Thr Asn Gln Thr Glu Ala Glu Leu Ala Thr
                260              265              270
Pro Glu Gly Ile Tyr Glu Arg Pro Val Asp Tyr Leu Pro Glu Arg Asp
                275              280              285
Val Tyr Glu Ser Leu Cys Arg Gly Gly Val Lys Leu Thr Pro Arg
290              295              300
Arg Gln Lys Arg Leu Phe Cys Arg Tyr His His Gly Asn Arg Ala Pro
305              310              315              320
Gln Leu Leu Ile Ala Pro Phe Lys Glu Glu Asp Glu Trp Asp Ser Pro
                325              330              335
His Ile Val Arg Tyr Tyr Asp Val Met Ser Asp Glu Glu Ile Glu Arg
                340              345              350
Ile Lys Glu Ile Ala Lys Pro Lys Leu Ala Arg Ala Thr Val Arg Asp
                355              360              365
Pro Lys Thr Gly Val Leu Thr Val Ala Ser Tyr Arg Val Ser Lys Ser
                370              375              380
Ser Trp Leu Glu Glu Asp Asp Pro Val Val Ala Arg Val Asn Arg
385              390              395              400
Arg Met Gln His Ile Thr Gly Leu Thr Val Lys Thr Ala Glu Leu Leu
                405              410              415
Gln Val Ala Asn Tyr Gly Val Gly Gln Tyr Glu Pro His Phe Asp
                420              425              430
Phe Ser Arg Arg Pro Phe Asp Ser Gly Leu Pro Thr Leu Gly Gln Arg
                435              440              445
Gly Ile Val Leu Ala Thr Phe Leu Asn Tyr Met Ser Asp Val Glu Ala
450              455              460
Gly Gly Ala Thr Val Phe Pro Asp Leu Gly Ala Ala Ile Trp Pro Lys
465              470              475              480
Lys Gly Thr Lys Leu Cys Ser Gly Thr Thr Ser Cys Gly Ala Gly Lys
                485              490              495
Val Thr Thr Glu Gln Asp Met Leu Pro Ala Leu Cys Leu Trp Ala Ala
                500              505              510
Ser Gly Ser Pro Ile Ser Gly Ser Met Asn Glu Asp Arg Ser Ser
                515              520              525
```

(2) INFORMATION FOR SEQ ID NO:146:

(i) SEQUENCE CHARACTERISTICS:
        (A) LENGTH: 727 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
      (C) INDIVIDUAL ISOLATE: TcA - N-terminal fragment (xi) SEQUENCE DESCRIPTION: SEQ ID NO:146:

| | | | | | |
|---|---|---|---|---|---|
| GTTGGTGTCA | GCGGGCAACA | GCCCACAGGA | GTGTGCACCT | CCTAGGACAG | AGTTTGTCCT | 60 |
| CTCACTTCTG | GAGAAGATGC | AGACACAGGA | GATCCTGAGG | ATACTGCGAC | TGCCTGAGCT | 120 |
| AGGTGACTTG | GGACAGTTTT | TCCGCAGCCT | CTCGGCCACC | ACCCTCGTGA | GTATGGGTGC | 180 |
| CCTGGCTGCC | ATCCTTGCCT | ACTGGTTCAC | TCACCGGCCA | AAGGCCTTGC | AGCCGCCATG | 240 |
| CAACCTCCTG | ATGCAGTCAG | AAGAAGTAGA | GGACAGTGGC | GGGGCACGGC | GATCTGTGAT | 300 |
| TGGGTCTGGC | CCTCAGCTAC | TTACCCACTA | CTATGATGAT | GCCCGGACCA | TGTACCAGGT | 360 |
| GTTCCGCCGT | GGGCTTAGCA | TCTCAGGGAA | TGGGCCCTGT | CTTGGTTTCA | GGAAGCCTAA | 420 |
| GCAGCCTTAC | CAGTGGCTGT | CCTACCAGGA | GGTGGCCGAC | AGGGCTGAAT | TCTGGGGTC | 480 |
| CGGACTTCTC | CAGCACAATT | GTAAAGCATG | CACTGATCAG | TTTATTGGTG | TTTTTGCACA | 540 |
| AAATCGGCCA | GAGTGGATCA | TTGTGGAGCT | GGCCTGCTAC | ACATATTCCA | TGGTGGTGGT | 600 |
| CCCGCTCTAT | GACACCCTGG | GCCCTGGGGC | TATCCGCTAC | ATCATCAATA | CAGCGGACAT | 660 |
| CAGCACCGTG | ATTGTGGACA | AACCTCAGAA | GGCTGTGCTT | CTGCTAGAGC | ATGTGGAGAG | 720 |
| GAAGGAG | | | | | | 727 |

(2) INFORMATION FOR SEQ ID NO:147:

(i) SEQUENCE CHARACTERISTICS:
      (A) LENGTH: 874 base pairs
      (B) TYPE: nucleic acid
      (C) STRANDEDNESS: double
      (D) TOPOLOGY: linear (ii) MOLECULE TYPE: cDNA to mRNA (iii) HYPOTHETICAL: NO (iv) ANTI-SENSE: NO (vi) ORIGINAL SOURCE:
      (C) INDIVIDUAL ISOLATE: TcA - C-terminal fragment (xi) SEQUENCE DESCRIPTION: SEQ ID NO:147:

| | | | | | |
|---|---|---|---|---|---|
| GTGTGAGAGG | ACCAAATGTG | TTCAAAGGCT | ACTTGAAAGA | TCCAGACAGG | ACGAAGGAGG | 60 |
| CCCTGGACAG | CGATGGCTGG | CTTCACACTG | GAGACATCGG | AAAATGGCTG | CCGGCAGGAA | 120 |
| CTCTTAAAAT | TATTGATCGG | AAAAAGCATA | TATTTAAACT | TGCTCAGGGA | GAATATGTTG | 180 |
| CACCCGAGAA | GATTGAGAAC | ATCTACATCC | GGAGCCAACC | TGTGGCGCAA | ATCTATGTCC | 240 |
| ATGGGGACAG | CTTAAAGGCC | TTTTTGGTAG | GCATTGTTGT | GCCTGACCCT | GAAGTTATGC | 300 |
| CCTCCTGGGC | CCAGAAGAGA | GGAATTGAAG | GAACATATGC | AGATCTCTGC | ACAAATAAGG | 360 |
| ATCTGAAGAA | AGCCATTTTG | GAAGATATGG | TGAGGTTAGG | AAAAGAAAGT | GGACTCCATT | 420 |
| CTTTTGAGCA | GGTTAAAGCC | ATTCACATCC | ATTCTGACAT | GTTCTCAGTT | CAAAATGGCT | 480 |
| TGCTGACACC | AACACTAAAA | GCTAAGAGAC | CTGAGCTGAG | AGAGTACTTC | AAAAAACAAA | 540 |
| TAGAAGAGCT | TTACTCAATC | TCCATGTGAA | GTTCAAGGAA | AGTTCTTCTC | AGTGTAATGA | 600 |
| ACTGTCTAGC | AATATTATAG | TTATTCTTGA | AAGTAATGAG | TCAAAATGAC | ACAGCTGAAA | 660 |
| ATGAATAAGC | ATCTGATTTT | ATGACTGAGC | CTTTTCCTGT | CCCAAGAGGT | CTTTAACAAT | 720 |
| ATTTTCTCTA | TCATCAATGA | GTATATTTTA | TTTTTATTAT | AAAAATGATA | TTGTGGTGGA | 780 |
| CTGCTAAAAA | TATCACAAAT | GGCAATGTAA | AAATCAAGAC | ATTTTCTCAA | GAACTGTGTA | 840 |

```
CCACTAAAAG TAATATATTG TCAATGTTCA CAGG                                              874
```

(2) INFORMATION FOR SEQ ID NO:148:

(i) SEQUENCE CHARACTERISTICS:
        (A) LENGTH: 1312 amino acids
        (B) TYPE: amino acid
        (D) TOPOLOGY: linear (ii) MOLECULE TYPE: protein (iii) HYPOTHETICAL: NO (vi) ORIGINAL SOURCE:
        (C) INDIVIDUAL ISOLATE: Rad50.pro-translation of SEQ ID NO:54

(xi) SEQUENCE DESCRIPTION: SEQ ID NO:148:

```
Met Ser Arg Ile Glu Lys Met Ser Ile Leu Gly Val Arg Ser Phe Gly
  1               5                  10                  15

Ile Glu Asp Lys Asp Lys Gln Ile Ile Thr Phe Phe Ser Pro Leu Thr
                 20                  25                  30

Ile Leu Val Gly Pro Asn Gly Ala Gly Lys Thr Thr Ile Ile Glu Cys
             35                  40                  45

Leu Lys Tyr Ile Cys Thr Gly Asp Phe Pro Pro Gly Thr Lys Gly Asn
         50                  55                  60

Thr Phe Val His Asp Pro Lys Val Ala Gln Glu Thr Asp Val Arg Ala
 65                  70                  75                  80

Gln Ile Arg Leu Gln Phe Arg Asp Val Asn Gly Glu Leu Ile Ala Val
                 85                  90                  95

Gln Arg Ser Met Val Cys Thr Gln Lys Ser Lys Lys Thr Glu Phe Lys
                100                 105                 110

Thr Leu Glu Gly Val Ile Thr Arg Thr Lys His Gly Glu Lys Val Ser
            115                 120                 125

Leu Ser Ser Lys Cys Ala Glu Ile Asp Arg Glu Met Ile Ser Ser Leu
        130                 135                 140

Gly Val Ser Lys Ala Val Leu Asn Asn Val Ile Phe Cys His Gln Glu
145                 150                 155                 160

Asp Ser Asn Trp Pro Leu Ser Glu Gly Lys Ala Leu Lys Gln Lys Phe
                165                 170                 175

Asp Glu Ile Phe Ser Ala Thr Arg Tyr Ile Lys Ala Leu Glu Thr Leu
            180                 185                 190

Arg Gln Val Arg Gln Thr Gln Gly Gln Lys Val Lys Glu Tyr Gln Met
        195                 200                 205

Glu Leu Lys Tyr Leu Lys Gln Tyr Lys Glu Lys Ala Cys Glu Ile Arg
    210                 215                 220

Asp Gln Ile Thr Ser Lys Glu Ala Gln Leu Thr Ser Ser Lys Glu Ile
225                 230                 235                 240

Val Lys Ser Tyr Glu Asn Glu Leu Asp Pro Leu Lys Asn Arg Leu Lys
                245                 250                 255

Glu Ile Glu His Asn Leu Ser Lys Ile Met Lys Leu Asp Asn Glu Ile
            260                 265                 270

Lys Ala Leu Asp Ser Arg Lys Lys Gln Met Glu Lys Asp Asn Ser Glu
        275                 280                 285

Leu Glu Glu Lys Met Glu Lys Val Phe Gln Gly Thr Asp Glu Gln Leu
    290                 295                 300

Asn Asp Leu Tyr His Asn His Gln Arg Thr Val Arg Glu Lys Glu Arg
305                 310                 315                 320
```

-continued

```
Lys Leu Val Asp Cys His Arg Glu Leu Glu Lys Leu Asn Lys Glu Ser
                325                 330                 335

Arg Leu Leu Asn Gln Glu Lys Ser Glu Leu Leu Val Glu Gln Gly Arg
            340                 345                 350

Leu Gln Leu Gln Ala Asp Arg His Gln Glu His Ile Arg Ala Arg Asp
                355                 360                 365

Ser Leu Ile Gln Ser Leu Ala Thr Gln Leu Glu Leu Asp Gly Phe Glu
        370                 375                 380

Arg Gly Pro Phe Ser Glu Arg Gln Ile Lys Asn Phe His Lys Leu Val
385                 390                 395                 400

Arg Glu Arg Gln Glu Gly Glu Ala Lys Thr Ala Asn Gln Leu Met Asn
                405                 410                 415

Asp Phe Ala Glu Lys Glu Thr Leu Lys Gln Lys Gln Ile Asp Glu Ile
                420                 425                 430

Arg Asp Lys Lys Thr Gly Leu Gly Arg Ile Ile Glu Leu Lys Ser Glu
            435                 440                 445

Ile Leu Ser Lys Lys Gln Asn Glu Leu Lys Asn Val Lys Tyr Glu Leu
        450                 455                 460

Gln Gln Leu Glu Gly Ser Ser Asp Arg Ile Leu Glu Leu Asp Gln Glu
465                 470                 475                 480

Leu Ile Lys Ala Glu Arg Glu Leu Ser Lys Ala Glu Lys Asn Ser Asn
                485                 490                 495

Val Glu Thr Leu Lys Met Glu Val Ile Ser Leu Gln Asn Glu Lys Ala
                500                 505                 510

Asp Leu Asp Arg Thr Leu Arg Lys Leu Asp Gln Glu Met Glu Gln Leu
            515                 520                 525

Asn His His Thr Thr Arg Thr Gln Met Glu Met Leu Thr Lys Asp
        530                 535                 540

Lys Ala Asp Lys Asp Glu Gln Ile Arg Lys Ile Lys Ser Arg His Ser
545                 550                 555                 560

Asp Glu Leu Thr Ser Leu Leu Gly Tyr Phe Pro Asn Lys Lys Gln Leu
                565                 570                 575

Glu Asp Trp Leu His Ser Lys Ser Lys Glu Ile Asn Gln Thr Arg Asp
            580                 585                 590

Arg Leu Ala Lys Leu Asn Lys Glu Leu Ala Ser Ser Glu Gln Asn Lys
        595                 600                 605

Asn His Ile Asn Asn Glu Leu Lys Arg Glu Glu Gln Leu Ser Ser
        610                 615                 620

Tyr Glu Asp Lys Leu Phe Asp Val Cys Gly Ser Gln Asp Phe Glu Ser
625                 630                 635                 640

Asp Leu Asp Arg Leu Lys Glu Ile Glu Lys Ser Ser Lys Gln Arg
                645                 650                 655

Ala Met Leu Ala Gly Ala Thr Ala Val Tyr Ser Gln Phe Ile Thr Gln
                660                 665                 670

Leu Thr Asp Glu Asn Gln Ser Cys Cys Pro Val Cys Gln Arg Val Phe
            675                 680                 685

Gln Thr Glu Ala Glu Leu Gln Glu Val Ile Ser Asp Leu Gln Ser Lys
        690                 695                 700

Leu Arg Leu Ala Pro Asp Lys Leu Lys Ser Thr Glu Ser Glu Leu Lys
705                 710                 715                 720

Lys Lys Glu Lys Arg Arg Asp Glu Met Leu Gly Leu Val Pro Met Arg
                725                 730                 735
```

```
Gln Ser Ile Ile Asp Leu Lys Glu Lys Glu Ile Pro Glu Leu Arg Asn
            740                 745                 750
Lys Leu Gln Asn Val Asn Arg Asp Ile Gln Arg Leu Lys Asn Asp Ile
        755                 760                 765
Glu Glu Gln Glu Thr Leu Leu Gly Thr Ile Met Pro Glu Glu Glu Ser
    770                 775                 780
Ala Lys Val Cys Leu Thr Asp Val Thr Ile Met Glu Arg Phe Gln Met
785                 790                 795                 800
Glu Leu Lys Asp Val Glu Arg Lys Ile Ala Gln Gln Ala Ala Lys Leu
                805                 810                 815
Gln Gly Ile Asp Leu Asp Arg Thr Val Gln Val Asn Gln Glu Lys
            820                 825                 830
Gln Glu Lys Gln His Lys Leu Asp Thr Val Ser Ser Lys Ile Glu Leu
        835                 840                 845
Asn Arg Lys Leu Ile Gln Asp Gln Gln Glu Gln Ile Gln His Leu Lys
    850                 855                 860
Ser Thr Thr Asn Glu Leu Lys Ser Glu Lys Leu Gln Ile Ser Thr Asn
865                 870                 875                 880
Leu Gln Arg Arg Gln Gln Leu Glu Glu Gln Thr Val Glu Leu Ser Thr
                885                 890                 895
Glu Val Gln Ser Leu Tyr Arg Glu Ile Lys Asp Ala Lys Glu Gln Val
            900                 905                 910
Ser Pro Leu Glu Thr Thr Leu Glu Lys Phe Gln Gln Glu Lys Glu Glu
        915                 920                 925
Leu Ile Asn Lys Lys Asn Thr Ser Asn Lys Ile Ala Gln Asp Lys Leu
    930                 935                 940
Asn Asp Ile Lys Glu Lys Val Lys Asn Ile His Gly Tyr Met Lys Asp
945                 950                 955                 960
Ile Glu Asn Tyr Ile Gln Asp Gly Lys Asp Tyr Lys Lys Gln Lys
                965                 970                 975
Glu Thr Glu Leu Asn Lys Val Ile Ala Gln Leu Ser Glu Cys Glu Lys
            980                 985                 990
His Lys Glu Lys Ile Asn Glu Asp Met Arg Leu Met Arg Gln Asp Ile
        995                 1000                1005
Asp Thr Gln Lys Ile Gln Glu Arg Trp Leu Gln Asp Asn Leu Thr Leu
    1010                1015                1020
Arg Lys Arg Asn Glu Glu Leu Lys Glu Val Glu Glu Arg Lys Gln
1025                1030                1035                1040
His Leu Lys Glu Met Gly Gln Met Gln Val Leu Gln Met Lys Ser Glu
                1045                1050                1055
His Gln Lys Leu Glu Glu Asn Ile Asp Asn Ile Lys Arg Asn His Asn
            1060                1065                1070
Leu Ala Leu Gly Arg Gln Lys Gly Tyr Glu Glu Ile Ile His Phe
        1075                1080                1085
Lys Lys Glu Leu Arg Glu Pro Gln Phe Arg Asp Ala Glu Glu Lys Tyr
    1090                1095                1100
Arg Glu Met Met Ile Val Met Arg Thr Thr Glu Leu Val Asn Lys Asp
1105                1110                1115                1120
Leu Asp Ile Tyr Tyr Lys Thr Leu Asp Gln Ala Ile Met Lys Phe His
                1125                1130                1135
Ser Met Lys Met Glu Glu Ile Asn Lys Ile Ile Arg Asp Leu Trp Arg
            1140                1145                1150
Ser Thr Tyr Arg Gly Gln Asp Ile Glu Tyr Ile Glu Ile Arg Ser Asp
```

```
            1155                1160                1165

Ala Asp Glu Asn Val Ser Ala Ser Asp Lys Arg Arg Asn Tyr Asn Tyr
    1170                1175                1180

Arg Val Val Met Leu Lys Gly Asp Thr Ala Leu Asp Met Arg Gly Arg
1185                1190                1195                1200

Cys Ser Ala Gly Gln Lys Val Leu Ala Ser Leu Ile Ile Arg Leu Ala
                1205                1210                1215

Leu Ala Glu Thr Phe Cys Leu Asn Cys Gly Ile Ile Ala Leu Asp Glu
            1220                1225                1230

Pro Thr Thr Asn Leu Asp Arg Glu Asn Ile Glu Ser Leu Ala His Ala
            1235                1240                1245

Leu Val Glu Ile Ile Lys Ser Arg Ser Gln Gln Arg Asn Phe Gln Leu
    1250                1255                1260

Leu Val Ile Thr His Asp Glu Asp Phe Val Glu Leu Leu Gly Arg Ser
1265                1270                1275                1280

Glu Tyr Val Glu Lys Phe Tyr Arg Ile Lys Lys Asn Ile Asp Gln Cys
                1285                1290                1295

Ser Glu Ile Val Lys Cys Ser Val Ser Ser Leu Gly Phe Asn Val His
            1300                1305                1310
```

(2) INFORMATION FOR SEQ ID NO:149:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: Primer A116-2

(xi) SEQUENCE DESCRIPTION: SEQ ID NO:149:

GGACCAGTAC TTCCTGAGCT TG                            22

(2) INFORMATION FOR SEQ ID NO:150:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (C) INDIVIDUAL ISOLATE: A116-1

(xi) SEQUENCE DESCRIPTION: SEQ ID NO:150:

TTGGTGCTGA ATACCAGCCC TG                            22

(2) INFORMATION FOR SEQ ID NO:151:

(i) SEQUENCE CHARACTERISTICS:
        (A) LENGTH: 650 base pairs
        (B) TYPE: nucleic acid -continued

```
        (C) STRANDEDNESS: unknown
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: a94g6ds-116f.seq (xi) SEQUENCE DESCRIPTION: SEQ ID NO:151:

GCCACTCACA CAGCATCTCC AAGATCAGGG ACCAGTACTT CCTGAGCTTG ACAGAGAATG    60

AATGTGTCAG ACTGACCTCT GCCCATTTTG TAGTTTTCTC ATCATTTTCT CACTCAGTCT   120

TCCCTTTTCA AGGGCCCACA CTCTTCCCGA GGGCTGGGCC TAGTGAGCGG GGTCACAGTA   180

CATATGGTTT CTGGGACTGA GAAGGTGGAA GATGTGTCCA TAGAGCTTTT GTTTCCTAAG   240

CAACGTATTA CTGCCATGAT TCCATTCCCT AGATGATGCT GGTGATGCAA GCTGGCTTCT   300

CTTGGCCAGC CTACCCTACT GCTGGGTAGT GTTTATGCCC CATGGCCAGA CACTGAAGAG   360

GGAGACAGGA AAAGCACATA TCCACACCTT CCACCCTCAG ACATTCCTGT AACTTGAGCT   420

TATCTAAGGG GGCATTGTCA TATGTCAGGG GTTCCCAAAC TACGGTCTTC AGAAACACTG   480

TTTACCCTCC ATAGAGGTTG TGTGCATCAG CCCAGGCAGA ATCCTGCTTC ATGAAGGTGT   540

TTTCCTAATG CATGTGTGCA TGGACCTGTC TCATGCTACA CTGCAGGGCT GGTATTCAGC   600

ACCAATAGTT ATTGTTGGCT GCTAAAATAG CAAACTAGCC AAAATGGCAG              650
```